(12) United States Patent
Zhao et al.

(10) Patent No.: US 12,280,072 B2
(45) Date of Patent: *Apr. 22, 2025

(54) OLIGOSACCHARIDE COMPOUND FOR INHIBITING INTRINSIC COAGULATION FACTOR X-ENZYME COMPLEX, AND PREPARATION METHOD THEREFOR AND USES THEREOF

(71) Applicants: Jiuzhitang Co., Ltd., Changsha (CN); Mudanjiang YouBo Pharmaceutical Co., Ltd., Heilongjiang (CN)

(72) Inventors: Jinhua Zhao, Kunming (CN); Zhenguo Li, Changsha (CN); Na Gao, Kunming (CN); Mingyi Wu, Kunming (CN); Yanming Chen, Mudanjiang (CN); Longyan Zhao, Kunming (CN); Yongsheng Wu, Mudanjiang (CN); Zi Li, Kunming (CN); Chuang Xiao, Kunming (CN); Shunliang Zheng, Mudanjiang (CN); Zhiyuan Nan, Mudanjiang City (CN); Jianbo Zhou, Mudanjiang (CN); Jianping Xu, Kunming (CN); Lutan Zhou, Kunming (CN); Yafang Guo, Mudanjiang (CN); Hongbo Qin, Kunming (CN); Jikai Liu, Kunming (CN)

(73) Assignees: Jiuzhitang Co., Ltd. (CN); Mudanjiang YouBo Pharmaceutical Co., Ltd (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/374,543

(22) Filed: Sep. 28, 2023

(65) Prior Publication Data
US 2024/0041918 A1 Feb. 8, 2024

Related U.S. Application Data

(62) Division of application No. 16/476,720, filed as application No. PCT/CN2017/070716 on Jan. 10, 2017.

(51) Int. Cl.
| | | |
|---|---|---|
| A61K 31/727 | (2006.01) | |
| A61K 9/00 | (2006.01) | |
| A61P 7/02 | (2006.01) | |

(52) U.S. Cl.
CPC .......... *A61K 31/727* (2013.01); *A61K 9/0019* (2013.01); *A61P 7/02* (2018.01)

(58) Field of Classification Search
CPC .......... C07H 1/00; C07H 11/00; C08B 37/00; C08B 37/0063; A61P 7/02; A61P 9/10
See application file for complete search history.

(56) References Cited

U.S. PATENT DOCUMENTS 9,896,517 B2 * 2/2018 Zhao ................... C08B 37/0063

FOREIGN PATENT DOCUMENTS

| CN | 101724086 | 6/2010 |
|---|---|---|
| CN | 101735336 | 6/2010 |
| CN | 102558389 | 7/2012 |
| CN | 103214591 | 7/2013 |
| CN | 104370980 | 2/2015 |
| EP | 2 980 103 A1 | 2/2016 |
| EP | 3 093 296 A1 | 11/2016 |

* cited by examiner

*Primary Examiner* — Pancham Bakshi
(74) *Attorney, Agent, or Firm* — Thorpe North & Western, LLP.

(57) ABSTRACT

A purified oligosaccharide compound having antithrombotic activity or a mixture of a homologous compound thereof and a pharmaceutically acceptable salt thereof, a preparation method for the mixture, a pharmaceutical composition containing the mixture, and uses thereof serving as an intrinsic factor X-enzyme (Xase) inhibitor in the preparation of drugs for preventing and/or treating thrombotic diseases.

7 Claims, 15 Drawing Sheets

OLIGOSACCHARIDE COMPOUND FOR INHIBITING INTRINSIC COAGULATION FACTOR X-ENZYME COMPLEX, AND PREPARATION METHOD THEREFOR AND USES THEREOF

RELATED APPLICATIONS

The present application is a divisional of U.S. patent application Ser. No. 16/476,720, filed Jul. 9, 2019, which is a 371 nationalization of PCT/CN2017/070716 filed Jan. 10, 2017, the entire specifications of which are hereby incorporated by reference in their entirety for all purposes.

FIELD OF THE INVENTION

The present invention belongs to the technical field of medicine, and in particular relates to a purified oligosaccharide compound having antithrombotic activity or a mixture of homologous compounds thereof, and a pharmaceutically acceptable salt thereof, a preparation method and uses thereof.

BACKGROUND OF THE INVENTION

Thromboembolic diseases including ischemic stroke, coronary heart disease, venous thromboembolism are the major lethal causes of human beings. Anti-thrombotic drugs such as fibrinolytic, anticoagulant and antiplatelet drugs are the basic means for clinical drug prevention and treatment of thrombotic diseases, but existing antithrombotic drugs have common defects: bleeding tendency and serious bleeding risk. Reducing bleeding tendency and bleeding risk is the core goal of the development of new antithrombotic drugs. Researches in recent years have found that intrinsic coagulation pathways are closely related to pathological thrombosis, and may not be necessary for hemostasis. Therefore, intrinsic coagulation factor inhibitors have become the focus of research on antithrombotic drugs with low bleeding tendency. Among them, preclinical and clinical trial studies on coagulation factor XIIa, XIa and IXa inhibitors have been carried out in succession. The intrinsic factor tenase complex (Xase) is the final and rate-limiting enzyme of the intrinsic coagulation pathway, and its selective inhibitor has important potential clinical application value.

Fucosylated glycosaminoglycan (FG) is a glycosaminoglycan with unique chemical structures and pharmacological activities found up to now exclusively in echinoderms, which has a chondroitin sulfate-like backbone, and sulphated fucosyl (Fuc)-substituted side chains (Yoshida et. al, *Tetrahedron Lett*, 1992, 33: 4959-62; Mourio et. al, *J Biol Chem*, 1996, 271: 23973-84). Studies have shown that native FG has potent anticoagulant activity, and its anticoagulant mechanism is mainly related to inhibition of intrinsic Xase activity (*Thromb Haemost*, 2008, 100: 420-8; *J. Biol. Chem.*, 1996, 271: 23973-84). However, native FG has extensive and contradictory pharmacological effects, including induction of platelet aggregation and induced decrease in circulating platelet count, activation of XII and such a side effect may cause hypotension, and so on (*Thromb Haemost*, 1988, 59: 432-4; *Thromb Haemost*, 2010, 103: 994-1004). Thus the application value of FG under systemic administration is limited. Properly depolymerized FG can reduce the activity of induction of platelet aggregation (*Thromb Haemost*, 1991, 65: 369-73), thereby increasing its selectivity for inhibition of the intrinsic factor Xase.

The present inventors have previously systematically studied the chemical depolymerization of native FG and the chemical and pharmacological properties of the depolymerized product. For example, the Chinese invention patent CN 101724086 B discloses a peroxidative depolymerization method of FG, and the obtained depolymerized product can inhibit thrombus formation and the bleeding tendency is significantly reduced, however, the product obtained by the method is difficult to be further isolated and purified due to the complicated terminal structure.

It has been found now that the native FG obtained by extracting from the body wall of echinoderms by a conventional method usually also contains glucan, fucan and/or hexosamine-containing polysaccharide compounds, which have a molecular weight distribution like that of native FG. These polysaccharides in native FG are difficult to be removed completely by gel chromatography, ultrafiltration or even ion exchange chromatography. A comparative study conducted by the present inventors has shown that using the technical methods described in the above literatures, the natural FG extracted from the echinoderms usually contains other polysaccharide compositions in a mass ratio of about 10%~20%. Since all of these polysaccharide compositions could be depolymerized by peroxidation, the oligosaccharide compositions of the peroxidative depolymerization product of natural FG are quite complicated.

Chinese invention patent CN 103214591A discloses a deacetylation-deaminative depolymerization method of FG, which can selectively cleave D-acetylgalactosamine (Gal-NAc)-($\beta$1→4)-D-glucuronic acid (D-GlcA) glycosidic bond, obtaining a depolymerized product containing 2,5-anhydro-D-talose (anTal) at the reducing terminal. The oligosaccharide homologues in the obtained depolymerized product are composed of 3m monosaccharide residues (m is a natural number, hereinafter the same). The deacetylation-deaminative depolymerization method cannot depolymerize glucan and fucan mixed in natural FG, and after the deacylative-deaminative depolymerization treatment, these undepolymerized polysaccharide impurities can be easily removed by gel chromatography or ultrafiltration method. The deacylative-deaminative depolymerization product of natural FG has more regular structural features, and the oligosaccharide contained therein may be further isolated and purified (CN 104370980A). Studies have shown that among the homologous oligosaccharide compounds obtained by deacylative-deaminative depolymerization of natural FG, nonasaccharide (NSac) is the the minimum fragment with potent inhibitory activity against Xase (*Proc Natl Acad Sci USA*. 2015; 112(27): 8284-9).

The present inventors' granted patent CN 201310099800 discloses a $\beta$-eliminative depolymerization method of native FG. The method comprises treating FG carboxylate with a base in a non-aqueous solvent to selectively cleave D-GalNAc-($\beta$1→4)-D-GlcA glycosidic bond, thereby obtaining a depolymerized product containing unsaturated $\Delta^{4,5}$-hexuronic acid group ($\Delta$UA) at the non-reducing terminal, and the depolymerized product is a mixture of a series of oligosaccharide compounds. Similarly, since the $\beta$-elimination depolymerization method has an excellent glycosidic bond selectivity, it cannot depolymerize other types of polysaccharides contained in the native FG extract, thereby facilitating the removal of non-FG polysaccharide impurities from the FG extract.

However, unlike the depolymerized product obtained by the deacetylative-deaminative depolymerization method described in the patent application CN 103214591 A, although the non-reducing terminals of the $\beta$-elimination depolymerization product described in CN 201310099800 are relatively regular, its reducing terminal compositions are relatively complicated: the reducing terminal residues include both "-D-GalNAc" and L-Fuc-(α1→3) substituted "-4-D-GlcA". Since the structure of the reducing terminal is relatively complicated, it is technically difficult to isolate and obtain the purified oligosaccharide from the depolymerized product, and therefore it is generally preferred to directly use the depolymerized product in the form of a mixture.

It is easy for those skilled in the pharmacy to understand that the purified oligosaccharide has a pure chemical structure and a higher quality control level, and thus may have higher application value. Obviously, for the depolymerized product of natural FG, the degree of regularity of the terminal structure may significantly affect the technical feasibility of preparation of purified oligosaccharide compounds.

Theoretically, the β-eliminative depolymerization method can selectively cleave the "-D-GalNAc-(β1→4)-D-GlcA-" glycosidic bond, and the reducing terminal of the resulting depolymerized product should be "-D-GalNAc" residue, and the oligosaccharide homologue in the resulting depolymerized product should generally be composed of 3m monosaccharide residues. A certain amount of oligosaccharide compound having "-[L-Fuc-(α1→3)]-D-GlcA-" at the reducing terminal is present in the β-elimination depolymerization product of natural FG disclosed in the patent application CN 201310099800, which indicates that during the β-elimination reaction under such conditions, there should be some side reactions, and in particular, the residue at the reducing terminal of the depolymerized product is damaged to some extent.

By further study of the β-elimination reaction conditions of natural FG, the present inventors have found that using a reducing agent could reduce the reducing terminal residue of natural FG to its corresponding alditol, and the carboxylic acid esterification product thereof can be subjected to β-elimination reaction in a basic non-aqueous solvent described in patent ZL 201310099800, however, the depolymerized product also contains some oligosaccharide compounds having "-D-GlcA-" residue at the reducing terminal. According to HPGPC analysis of the depolymerized product and calculation by area normalization method, the oligosaccharide compound having -D-GlcA at the reducing terminal may account for about 10%~30% of the total amount of the oligosaccharide compounds, and the result is similar to that of the depolymerized product of natural FG containing hemiacetal structure at the reducing terminal under the same conditions. Studies have shown that the reduction of the reducing terminal residue of natural FG to an alditol group does not affect the progress of the β-elimination reaction of the FG carboxyl ester, and does not reduce the destruction of the reducing terminal residue of the depolymerized product, either.

When a reducing agent (for example, sodium borohydride) is directly added to the basic non-aqueous solvent described in the β-elimination reaction of the patent application CN 201310099800, it is found that the β-elimination reaction of the natural FG carboxyl ester may proceed normally. Unexpectedly, the reducing terminal of the obtained product is substantially acetylaminogalactitol group (-3-D-GalNAc-ol); while the content of the oligosaccharide compound having "-3-D-GlcA (-ol)" residue at the reducing terminal is significantly reduced, and the content may be less than about 5% or even lower than the HPGPC detection limit, according to the HPGPC area normalization method. Thus, the homologous oligosaccharide compounds in the resulting depolymerized product may have a more regular terminal chemical structural feature: all the homologous oligosaccharide compounds are composed of 3m monosaccharide residues; the glycosyl at the non-reducing terminal is "L-Fuc-(α1-3)-ΔUA-1-" and the glycosyl group at the reducing terminal is "-3-D-GalNAc-ol".

By the β-elimination reaction in a basic non-aqueous organic solvent in the presence of a reducing agent and chromatographic separation technique, the inventors first isolated and purified a series of purified oligosaccharide compounds with novel chemical structures from the β-elimination depolymerization product of FG. The purified oligosaccharide compounds have a common chemical structural feature: the purified oligosaccharides are composed of 3m monosaccharide residues, and the non-reducing terminal structure is "L-Fuc-(α1-3)-ΔUA-1-", and the reducing terminal glycosyl group is "-3-D-GalNAc-ol".

The inventors have further studied and found that an oligosaccharide containing 3m monosaccharide residues can lose a monosaccharide residue through a "peeling reaction" at the reducing terminal, thereby producing an oligosaccharide "containing (3m−1) monosaccharide residues", and the reducing terminals of such oligosaccharides are all "-D-GlcA". Through intensive studies on the β-elimination reaction conditions of FG carboxyl esters, the inventors have also surprisingly found:

When a small amount of aqueous solution of a strong base (for example, NaOH) is added to the non-aqueous basic reaction solution described above, the FG oligosaccharide containing 3m monosaccharide residues and having "-3-D-GalNAc" at the reducing end is highly susceptible to the "peeling reaction" and lose the terminal "-D-GalNAc" glycosyl group. Unexpectedly, the oligosaccharide compound (which contains (3m−1) monosaccharide residues) having "-D-GlcA" at the reducing terminal produced by the "peeling reaction" is "unexpectedly" difficult to have a further "peeling reaction". Therefore, by improving the basic treatment conditions of the FG carboxyl ester in a non-aqueous solvent, after the β-elimination method cleaves the D-GalNAc-(β1→4)-D-GlcA glycosidic bond, the terminal "-3-D-GalNAc" glycosyl group of the depolymerized product can be further removed by the "peeling reaction" of the reducing terminal, thereby obtaining the oligosaccharide homologues with novel and regular chemical structural features.

HPGPC chromatographic analysis and NMR structural analysis show that in an anhydrous organic solvent, treating FG carboxyl ester with a strong base causes "β-elimination depolymerization", and then adding a small amount of strong basic aqueous solution to the reaction solution to further subject the depolymerized product of the β-elimination depolymerization to "peeling reaction", and the homologous oligosaccharide compounds contained in the depolymerized product may have a very regular chemical structure, that is, the homologous oligosaccharide compounds are composed of (3m−1) monosaccharide residues; the non-reducing terminal glycosyl group of the homologous oligosaccharide compounds is "L-Fuc-(α1-3)-ΔUA-1-", and the reducing terminal glycosyl group is "-4-D-GlcA" substituted by L-Fuc at the C3 position.

The oligosaccharide homologue obtained by the "β-elimination" and "peeling reaction" treatment of natural FG carboxyl ester have more regular chemical structural features, and thus is easily isolated and purified to obtain a series of purified oligosaccharide compounds. The common structural feature of the series of purified oligosaccharide compounds is that all the oligosaccharide compounds contain (3m−1) monosaccharide residues; the non-reducing terminal is "L-Fuc-(α1-3)-ΔUA-1-"; and the reducing terminal is "-4-[Fuc-(α1-3)]-D-GlcA".

It can be seen from the above that by further improving the β-elimination conditions of the natural FG carboxyl esters, the present invention can obtain a depolymerized product of FG having a more regular structure (especially a reducing terminal glycosyl structure): one is a depolymerized product having "-D-GalNAc-ol" at the reducing terminal, and the other is a depolymerized product having "-D-GlcA" at the reducing terminal. Since the terminal structure of the depolymerized product is more regular, the present invention first discloses a series of purified oligosaccharide compound derived from natural FG, which is isolated from such depolymerized products. The present invention further discloses various series of derivatives of the FG oligosaccharide compounds by structural modifications of specific chemical groups of such purified oligosaccharides.

Furthermore, by studying the structure-activity relationship on anti-coagulant activity of FG oligosaccharide compounds, inhibitory activity against intrinsic factor Xase, and activity of heparin cofactor II (HC-II)-dependent antithrombin (i.e., active coagulation factor IIa), the present inventors also found that:

For FG oligosaccharide homologue with a reducing terminal of "-D-GalNAc-ol" and containing 3m monosaccharide residues, the minimum structural fragment with potent inhibition against intrinsic factor Xase is nonasaccharide (NSac); for the FG oligosaccharide homologue with a reducing terminal of "-D-GlcA" and containing (3m−1) monosaccharide residues, the minimum structural fragment with potent inhibition against intrinsic factor Xase is octasaccharide (OSac); all the purified oligosaccharide compounds also have different intensity of HC-II dependent antithrombin activity and in vitro anticoagulant activity, and have pharmacological activity of inhibiting arteriovenous thrombosis in pathological models of experimental animals.

Since the purified oligosaccharide compounds of the present invention and the oligosaccharide derivatives obtained by the structural modification thereof have coagulation factor inhibitory activity as well as significant anticoagulant and antithrombotic activity, these oligosaccharide compounds have potential application value of prevention and/or treatment for thrombotic diseases.

In general, the present invention first discloses a technical method of obtaining natural FG depolymerized product with more regular chemical structure by "β-elimination depolymerization" or "β-elimination depolymerization and terminal peeling reaction" and a FG oligosaccharide homologue with a homogenous structure obtained by such method. The present invention also first discloses a purified FG oligosaccharide compound having unsaturated hexuronic acid residue structure at the non-reducing terminal, a structurally modified derivative thereof, and a mixture thereof. Since the oligosaccharide compound has anticoagulant and antithrombotic activity, the present invention also discloses the use of the oligosaccharide compound and a mixture thereof for the preparation of a medicament for the prevention and/or treatment of thrombotic diseases.

SUMMARY OF THE INVENTION

It is an object of the present invention to provide a purified oligosaccharide compound having anticoagulant and antithrombotic activity, a method for preparing the same, a pharmaceutical composition comprising the purified oligosaccharide compound or an oligosaccharide mixture and a pharmaceutically acceptable salt thereof, and use of the oligosaccharide compound, the oligosaccharide mixture and the pharmaceutical composition thereof for the preparation of a medicament for the prevention and/or treatment of thrombotic diseases.

The present invention first provides an oligosaccharide compound having antithrombotic activity, particularly an activity of inhibiting intrinsic coagulation factor Xase, and a pharmaceutically acceptable salt thereof. The oligosaccharide compound has a general structure represented by Formula (I):

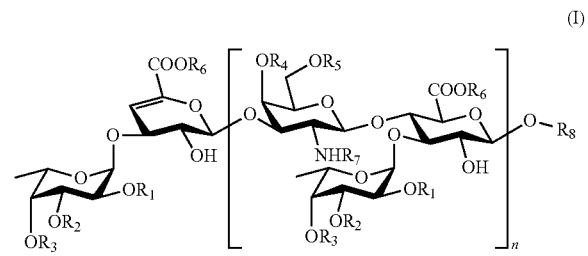

in Formula (I), $R_1$, $R_2$, $R_3$, $R_4$, $R_5$ are optionally and independently —H or —SO$_3$H;

$R_6$ is optionally —H, a substituted or unsubstituted C1-C6 hydrocarbon group or a C7-C12 aryl group;

$R_7$ is optionally —H, —SO$_3$, $C_2$-$C_5$ acyl;

$R_8$ is optionally a group represented by Formula (II), Formula (III) or Formula (IV):

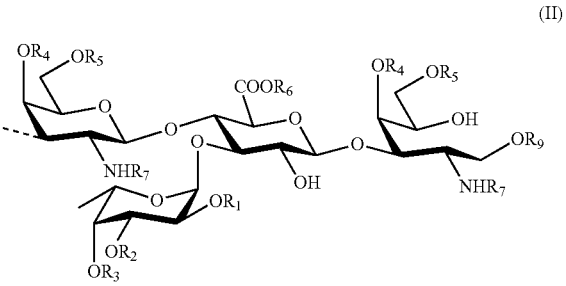

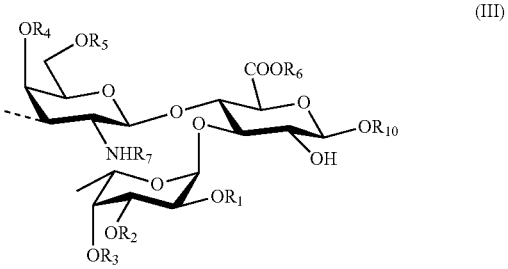

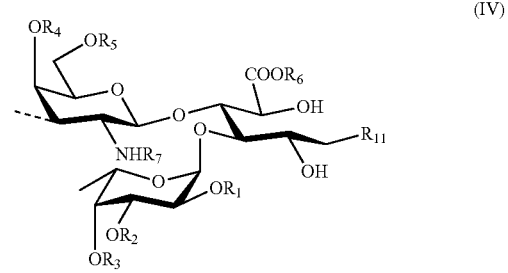

in Formula (II), Formula (III) and Formula (IV), $R_1$, $R_2$, $R_3$, $R_4$, $R_5$, $R_6$ and $R_7$ are all defined as above;

$R_9$ and $R_{10}$ are optionally —H, a substituted or unsubstituted C1-C6 hydrocarbon group or a C7-C12 aryl group;

$R_{11}$ is optionally —$NHR_{12}$ or —$OR_{13}$, wherein, $R_{12}$ and $R_{13}$ are optionally —H, a substituted or unsubstituted C1-C6 hydrocarbon group or a C7-C12 aryl group;

n is optionally 0 or a natural number of 1-8.

The oligosaccharide compound having the general structure represented by Formula (I) according to the present invention means a "purified oligosaccharide compound". In general, the "purified oligosaccharide compound" has a purity of no less than 95%. For example, by analyzing with analytical high-performance gel chromatography (HPGPC), such as Agilent high performance liquid chromatography and gel column, and detecting with a universal differential detector (RID), the purified oligosaccharide compound generally has a purity of no less than 95%, which is calculated according to the area normalization method.

Among the oligosaccharide compounds of the structure of Formula (I) of the present invention, a preferred oligosaccharide compound is the compound in which $R_8$ is a group represented by Formula (II), that is, the oligosaccharide compound has the general structure represented by Formula (V):

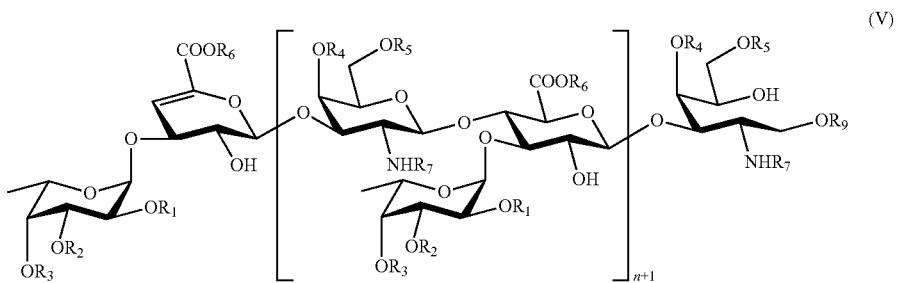

in Formula (V), $R_1$, $R_2$, $R_3$, $R_4$, $R_5$ are optionally and independently —H or —$SO_3H$;

$R_6$ is optionally —H, a substituted or unsubstituted C1-C6 hydrocarbon group or a C7-C12 aryl group;

$R_7$ is optionally —H, —$SO_3H$, C2-C5 acyl;

$R_9$ is optionally —H, a substituted or unsubstituted C1-C6 hydrocarbon group or a C7-C12 aryl group;

n is optionally 0 or a natural number of 1~8.

In a more preferred compound of Formula (V), $R_1$=—H, $R_2$=$R_3$=$R_4$=$R_5$=—$SO_3H$;

In another more preferred compound of Formula (V), $R_1$=$R_3$=$R_4$=$R_5$=—$SO_3H$; $R_2$=—H.

Among the oligosaccharide compounds of Formula (I) of the present invention, another preferred oligosaccharide compound is the compound in which $R_8$ is a group represented by Formula (III), that is, the oligosaccharide compound has the general structure represented by Formula (VI):

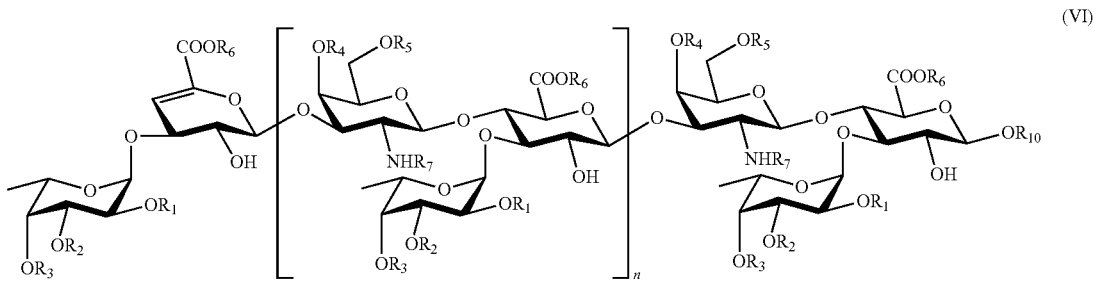

in Formula (VI), $R_1$, $R_2$, $R_3$, $R_4$, $R_5$ are optionally and independently —H or —$SO_3H$;

$R_6$ is optionally —H, a substituted or unsubstituted C1-C6 hydrocarbon group or a C7-C12 aryl group;

$R_7$ is optionally —H, —$SO_3H$, C2-C5 acyl;

$R_{10}$ is optionally —H, a substituted or unsubstituted C1-C6 hydrocarbon group or a C7-C12 aryl group; and n is optionally 0 or a natural number of 1-8.

Similarly, in a more preferred compound of Formula (VI), $R_1$=—H; $R_2$=$R_3$=$R_4R_5$=—$SO_3H$;

In another more preferred compound of Formula (VI), $R_1$=$R_3$=$R_4$=$R_5$=—$SO_3H$; $R_2$=—H.

In the oligosaccharide compound of Formula (I) of the present invention, another preferred oligosaccharide compound is the compound in which $R_8$ is a group represented by Formula (VII), that is, the oligosaccharide compound has the general structure represented by Formula (VII):

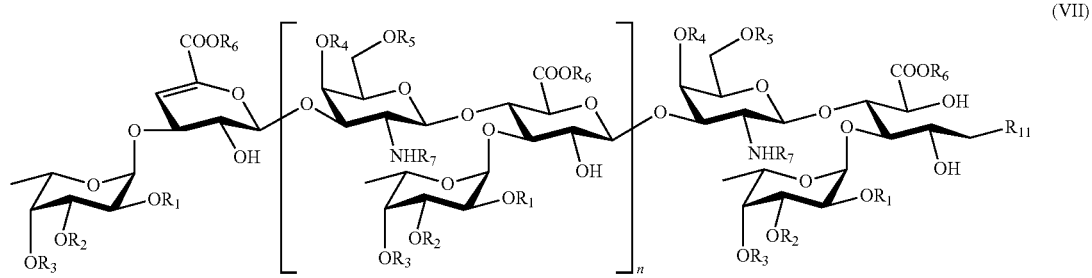

in Formula (VII), $R_1$, $R_2$, $R_3$, $R_4$, $R_5$ are optionally and independently —H or —$SO_3H$;

$R_6$ is optionally —H, a substituted or unsubstituted C1-C6 hydrocarbon group or a C7-C12 aryl group;

$R_7$ is optionally —H, —$SO_3H$, C2-C5 aryl group;

$R_{11}$ is optionally —$NHR_{12}$ or —$OR_{13}$, wherein, $R_{12}$ and $R_{13}$ are optionally —H, a substituted or unsubstituted C1-C6 hydrocarbon group or a C7-C12 aryl group; and n is optionally 0 or a natural number of 1~8.

Similarly, in a more preferred compound of Formula (VII), $R_1$=—H; $R_2$=$R_3$=$R_4$=$R_5$=—$SO_3H$;

In another more preferred compound of Formula (VII), $R_1$=$R_3$=$R_4$=$R_5$=—$SO_3H$; $R_2$=—H.

It will be readily understood by those skilled in the art that the technical difficulty in isolating and purifying the oligosaccharide compound of the present invention may increase as the degree of polymerization of the oligosaccharide increases. Therefore, among the oligosaccharide compounds of the structure represented by the above Formula (I), (V), (VI) or (VII) of the present invention, preferred oligosaccharide compounds are those in which n is optionally 1, 2, 3 or 4.

The purified oligosaccharide compound of the present invention has sulfate substituents and/or free carboxyl groups, and thus can be combined with a pharmaceutically acceptable inorganic and/or organic ion to form a salt. In general, the pharmaceutically acceptable salt of the oligosaccharide compound of the present invention may be optionally an alkali metal salt, an alkaline earth metal salt or an organic ammonium salt.

Preferred pharmaceutically acceptable salt of the oligosaccharide compound of the present invention is a sodium salt, a potassium salt or a calcium salt.

It will be readily understood by those skilled in the art that when the purified oligosaccharide compounds of the present invention in the form of homologues, such as homologues of the compound of Formula (V), or homologues of the compound of Formula (VI) or homologues of the compound of Formula (VII) described above, are mixed, a mixture of homologous oligosaccharide compounds having a specific structure type may be obtained. In particular, according to the preparation method of the compound of the present invention described later in the specification, the present invention may also obtain a FG oligosaccharide mixture in the form of homologues having more regular chemical structure (especially a reducing terminal glycosyl structure type) by a specific technical method.

Thus, the present invention also provides an oligosaccharide mixture having antithrombotic activity, particularly an activity of inhibiting intrinsic factor tenase, and a pharmaceutically acceptable salt thereof. The oligosaccharide mixture is composed of homologues of the above oligosaccharide compound of Formula (I); and $R_8$ of the oligosaccharide compound of Formula (I) in the oligosaccharide mixture is a group represented by Formula (II), or a group represented by (III), or a group represented by Formula (IV). Specifically, based on the molar ratio, the oligosaccharide compound in which $R_8$ is the group represented by Formula (II) accounts for not less than 95% in the mixture, or the oligosaccharide compound in which $R_8$ is the group represented by Formula (III) accounts for not less than 95% in the mixture; or the oligosaccharide compound in which $R_8$ is the group represented by Formula (IV) accounts for not less than 95% in the mixture.

In the oligosaccharide mixture of the present invention, a preferred oligosaccharide mixture is a mixture of homologous oligosaccharide compounds having the general structure represented by the above Formula (V). A more preferred oligosaccharide mixture of the present invention is a mixture of homologous oligosaccharide compounds of the structure represented by Formula (V), in which $R_1$=—H; $R_2$=$R_3$=$R_4$=$R_5$=—$SO_3H$; in another more preferred mixture of homologous oligosaccharide compounds of the structure represented by Formula (V), $R_1$=$R_3$=$R_4$=$R_5$=—$SO_3H$; $R_2$=—H.

In the oligosaccharide mixture of the present invention, another preferred oligosaccharide mixture is a mixture of homologous oligosaccharide compounds having the general structure represented by Formula (VI). Similarly, in more preferred mixture of homologous oligosaccharide compounds of the structure represented by Formula (VI), $R_1$=—H; $R_2$=$R_3$=$R_4$=$R_5$=—$SO_3H$; in another more preferred mixture of homologous oligosaccharide compounds of the structure represented by Formula (VI), $R_1$=$R_3$=$R_4$=$R_5$=—$SO_3H$; $R_2$=—H.

In the oligosaccharide mixture of the present invention, another preferred oligosaccharide mixture is a mixture of homologous oligosaccharide compounds having the general structure represented by Formula (VII). Similarly, in a more preferred mixture of homologous oligosaccharide compounds of the structure represented by Formula (VII), $R_1$=—H; $R_2$=$R_3$=$R_4$=$R_5$=—$SO_3H$; and in another more preferred mixture of homologous oligosaccharide compounds of the structure represented by Formula (VII), $R_1$=$R_3$=$R_4$=$R_5$=—$SO_3H$; $R_2$=—H.

For the oligosaccharide compound and the oligosaccharide mixture of the present invention described above, the present invention still further provides a method for preparing the compound and the mixture.

First, the present invention provides a preparation method of the oligosaccharide compound of the structure represented by Formula (I) and a pharmaceutically acceptable salt thereof. In the preparation method, fucosylated glycosaminoglycan (FG) derived from an echinoderm is used as a starting material of the reaction, and optionally is depolymerized by the following method:

Esterifying the FG carboxyl group and subjecting the FG carboxylate to "β-elimination reaction" and depolymerization in an anhydrous organic solvent in the presence of a strong base and a reducing agent, and reducing the -D-acetylaminogalactosyl (-D-GalNac) at the reducing terminal of the depolymerized product to an alditol (-D-GalNAc-ol), thereby obtaining a mixture of homologous oligosaccharide compounds;

Esterifying the FG carboxyl group and subjecting the FG carboxylate to "β-elimination reaction" and depolymerization in an anhydrous organic solvent in the presence of a strong base, followed by subjecting the depolymerized product to terminal "peeling reaction" by adding a basic aqueous solution to lose the -D-GalNAc at the reducing terminal, and obtain a mixture of homologous oligosaccharide compounds having -D-glucuronic acid (-D-GlcA) at the reducing terminal.

The mixture of homologous oligosaccharide compounds obtained by the "β-elimination depolymerization and terminal reduction" or "β-elimination depolymerization and peeling reaction" is isolated and purified and optionally structurally modified to obtain the desired purified oligosaccharide compound.

In particular, the method for preparing an oligosaccharide compound of the present invention is that for preparing an oligosaccharide compound having the structure represented by Formula (I) and having $R_8$ as the group represented by the above Formula (II). The named "oligosaccharide compound having the structure represented by Formula (I) and having $R_8$ as the group represented by Formula (II)" is substantially equivalent to the oligosaccharide compound of the structure represented by Formula (V) defined above.

The preparation method of the oligosaccharide compound of the structure represented by Formula (V) is a "β-elimination depolymerization+terminal reduction" method. The method comprises: in the presence of a strong base and a reducing agent in an anhydrous organic solvent, subjecting the carboxylated FG to a "β-elimination reaction" to cleave its "D-GalNAc-(β1→4)-GlcA" glycosidic bond, and reducing the reducing terminal D-GalNAc of the depolymerized product with a reducing agent to -D-GalNAc-ol, thereby obtaining a mixture of homologous oligosaccharide compounds with relatively regular terminal structure, followed by isolating and purifying, and optional structural modifying the specific substituent to obtain the desired purified oligosaccharide compound. The specific steps comprise:

(a) converting natural FG into a quaternary ammonium salt form, and completely or partially converting the carboxyl groups on D-GlcA in the FG quaternary ammonium salt into a carboxyl ester in an organic solvent;

(b) in an organic solvent having a reducing agent, treating the carboxylated FG quaternary ammonium salt of the step (a) with a strong base to cause β-elimination depolymerization, and reducing the -D-GalNAc at the reducing terminal of the depolymerized product to -D-GalNAc-ol, thereby obtaining a mixture of homologous oligosaccharide compounds with a relatively regular terminal structure;

(c) converting the mixture of homologous oligosaccharide compounds obtained in the step (b) into an alkali metal salt form, and in an aqueous solution, subjecting the carboxylate of the homologous oligosaccharide compound to basic hydrolysis, to obtain a mixture of homologous oligosaccharide compounds containing a free carboxyl group;

(d) isolating and purifying the homologous oligosaccharide compound by chromatography from the oligosaccharide mixture obtained in the step (c);

(e) optionally subjecting the purified oligosaccharide compound obtained in the step (d) to a further structural modification.

The steps (a)~(e) are as shown in the route scheme 1.

Scheme 1

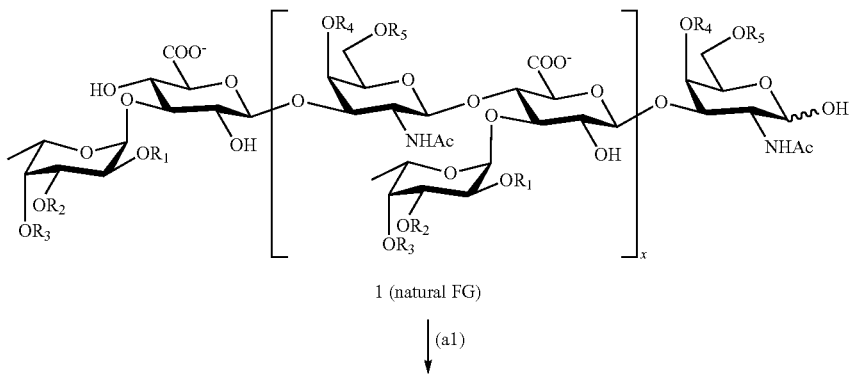

1 (natural FG)

↓ (a1)

-continued
2 (FG ammonium salt)
↓ (a2)
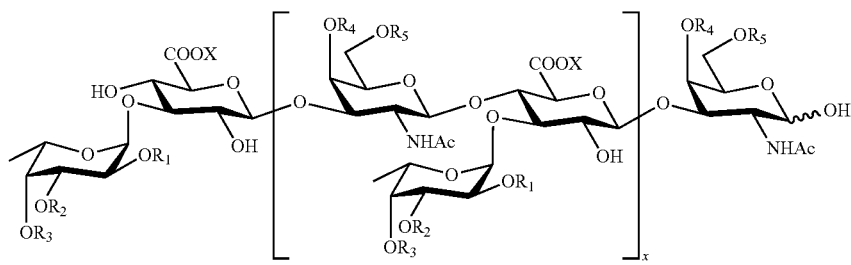
3 (FG ester ammonium salt)
↓ (b1)
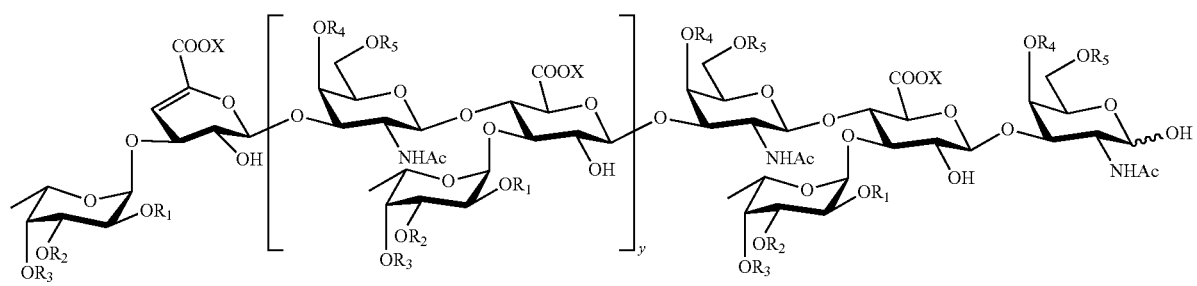
4 (dFG ester ammonium salt)
↓ (b2)
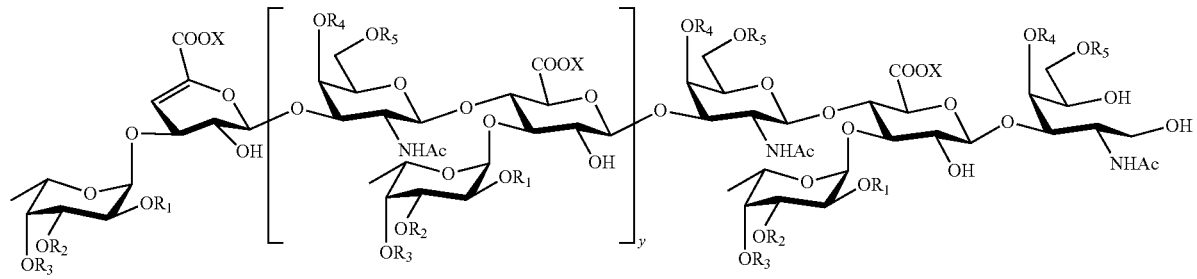
5 (reduced dFG ester ammonium salt)
↓ (c)
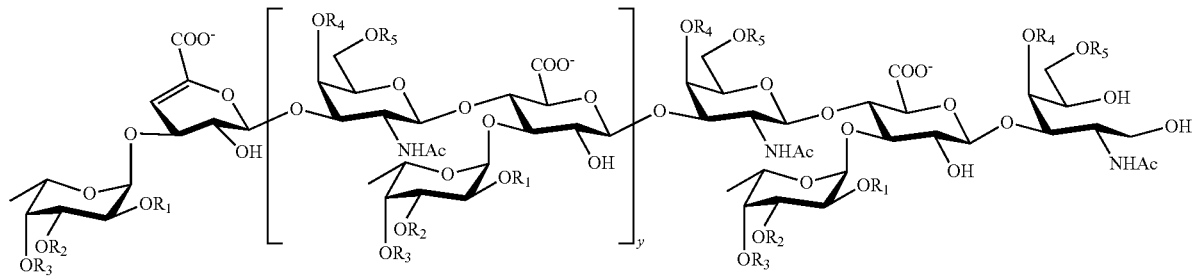
6 (reduced dFG)
↓ (d)

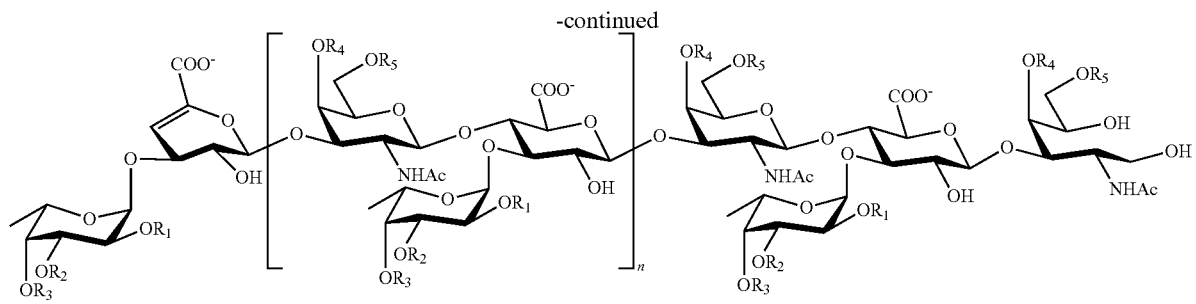

7 (purified oligosaccharide)

↓ (f)

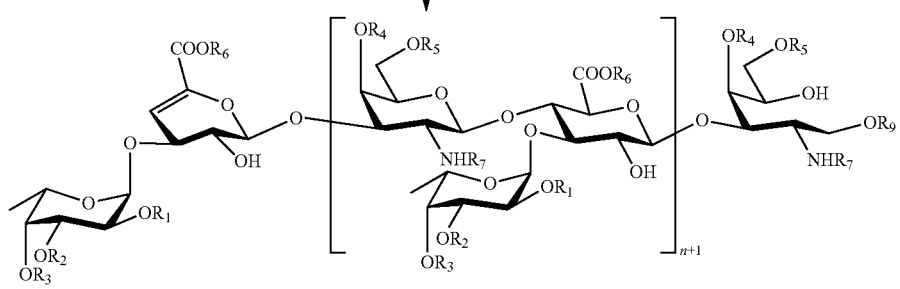

8

In Scheme 1:

Natural FG 1 is a natural FG derived from an echinoderm, which is a mixture of series of homologous polysaccharides;

FG ammonium salt 2 is a FG in the form of a quaternary ammonium salt;

FG ester ammonium salt 3 is a product in which part of or all the carboxyl groups on D-GlcA in the FG are esterified, which is present in the form of a quaternary ammonium salt;

dFG ester ammonium salt 4 is a depolymerized product formed by β-elimination reaction of the FG carboxylate, and the reducing terminal glycosyl-D-GalNAc could be reduced by the reducing agent present in the reaction solution to form a reduced dFG ester ammonium salt 5;

Reduced dFG 6 is a carboxylate hydrolyzate of 5 as an alkali metal salt; depolymerized products 4, 5 and 6 are all a mixture of homologous oligosaccharide compounds;

Purified oligosaccharide 7 is a purified oligosaccharide obtained by isolating from the depolymerized product 6; and the purified oligosaccharide 8 is a purified oligosaccharide obtained by optionally subjecting 7 to a substituent structural modification;

In the chemical structure of Scheme 1, $R_1$, $R_2$, $R_3$, $R_4$, $R_5$, $R_6$, $R_7$, $R_9$ and n are all defined as in the above Formula (I); x is a natural number having a mean value in the range of about 40~80; y is a natural number in the range of about 0~15; —COOX is a carboxylate or a quaternary ammonium salt of a carboxylic acid.

In Scheme 1, it can be seen from the chemical structure of natural FG that it has a chondroitin sulfate-like backbone structure and has sulfated L-Fuc side chain substituents. In general, natural FG can be understood as a polysaccharide compound formed by sequential linkage of the "trisaccharide structural units" {-4)-[L-FucS-(α1-3)]-D-GcA-(β1-3)-D-GalNAcS-(β1-}(wherein, FucS and GalNAcS represent sul-
fated Fuc and sulfated GalNAc, respectively). In general, natural FG typically contains a mean of about 40 to 80 of such trisaccharide structural units (approximately, the mean value of x is in the range of about 40~80).

The form in which the natural FG salt is present depends on the route of its extraction and purification. In general, the FG is present in the form of an alkali metal or alkaline earth metal salt (such as a sodium salt, a potassium salt or a calcium salt thereof). In order to achieve the chemical reaction in the organic solvent in the subsequent steps, natural FG is converted into a quaternary ammonium salt form in the step (a) (2 in Scheme 1).

The conversion of natural FG into a quaternary ammonium salt can optionally be carried out using techniques well known in the art. For example, the conversion into quaternary ammonium salt can be performed by quaternary ammonium salt precipitation method, which comprises adding an excess of an organic ammonium salt compound to an aqueous solution of an alkali metal or alkaline earth metal salt of FG, thereby forming a water-insoluble FG quaternary ammonium salt that can be easily precipitated from the aqueous solution; in addition, an alkali metal salt or an alkaline earth metal salt of FG can also be exchanged into an H-form FG using an ion exchange resin, followed by neutralization of the H-form FG with a basic organic ammonium to obtain a FG quaternary ammonium salt.

As shown in Scheme 1, the step (a2) comprises convering all or part of carboxyl groups on the D-GlcA residue in the FG quaternary ammonium salt (2) into a carboxylate (3). The purpose of the carboxyl esterification reaction of FG is to make it susceptible to the β-elimination reaction. The GlcA in the form of a carboxyl group is less likely to undergo a β-elimination depolymerization reaction, and its carboxylate is susceptible to the β-elimination reaction due to the electronic effect of the ester group.

Generally, the carboxyl esterification reaction of GlcA in the FG comprises: in an organic solvent such as dimethylformamide (DMF) or a mixed solvent of DMF and a lower alcohol, a ketone and/or an ether, reacting the carboxyl group on GlcA in the FG with a stoichiometric amount of a halogenated hydrocarbon, to easily obtain a desired FG carboxylate with different degrees of esterification. The degree of esterification of the FG carboxylate means the ratio of the number of moles of the carboxylate group formed after the esterification reaction to the number of moles of the free carboxyl group before the esterification reaction; the halogenated hydrocarbon may optionally be and is not limited to: a C1-C6 linear or branched, saturated or unsaturated, substituted or unsubstituted aliphatic hydrocarbon group; or a substituted or unsubstituted C7-C12 aromatic hydrocarbon group and so on. The present applicant discloses a method for the preparation of a FG carboxylate derivative in another invention patent application CN 201110318704.X, which is incorporated herein by reference in its entirety.

The step (b) shown in Scheme 1 comprises subjecting the FG carboxylate to β-elimination depolymerization (b1) to obtain the depolymerized product 4, and reducing the reducing terminal D-GalNAc of the depolymerized product 4 by a reducing agent to -D-GalNAc-ol (b2), and to obtain the depolymerized product 5.

As described above, CN 201310099800 discloses a β-elimination depolymerization method of natural FG. The method can obtain a depolymerized product having unsaturated ΔUA at the non-reducing terminal, but the structural type at the reducing terminal of the depolymerized product is relatively complicated: the glycosyl group at the reducing terminal includes both "-D-GalNAc" and L-Fuc substituted "-D-GlcA". Since the structure of the reducing terminal is complicated, it is difficult to isolate and obtain a purified oligosaccharide from the depolymerized product, and therefore it is generally preferred to directly use the depolymerized product in the form of a mixture. Theoretically, the β-elimination depolymerization method can selectively cleave the "D-GalNAc-(β1→4)-D-GlcA" glycosidic bond, and the resulting depolymerized product has a "-D-GalNAc" residue at the reducing terminal. Some amount of oligosaccharide compound having "-D-GlcA" at the reducing terminal is present in the depolymerized product of natural FG prepared by the β-elimination depolymerization method described in CN 201310099800, indicating that there are still some side reactions under the reaction conditions. In particular, the glycosyl group at the reducing terminal of some amount of depolymerized product is destroyed. The patent application CN 201310099800 is incorporated herein by reference in its entirety.

It will be readily understood by those skilled in the art that the purified oligosaccharide has a pure structure and a higher level of quality control, and thus may have higher application value. Through further studies on the β-elimination reaction conditions of natural FG, the present inventors have surprisingly found that:

The glycosyl group at the reducing terminal of the natural FG is reduced to an alditol by a reducing agent such as sodium borohydride, and the carboxylated product can undergo a β-elimination reaction in a basic non-aqueous solvent, but according to the HPGPC spectrum analysis of the depolymerized product, the oligosaccharide compound having -D-GlcA at the reducing terminal may account for about 10%~30% of the total amount of the oligosaccharide compound (area normalization method), and the result is similar to that of the depolymerized product of natural FG having unreduced reducing terminal under the same conditions. This result indicates that the terminal reduction does not affect the progress of the β-elimination reaction of the FG carboxylate.

Further studies have shown that when a reducing agent (such as sodium borohydride) is directly added to the basic non-aqueous solvent, and the β-elimination reaction of the natural FG carboxylate may also be carried out normally. Unexpectedly, the reducing terminal of the obtained product is substantially -3-D-GalNAc-ol, while the content of the oligosaccharide compound having -3-D-GlcA-ol at the reducing terminal is very small (the content may be less than about 5%, even below the HPGPC detection limit). This result indicates that the terminal reduction of the depolymerized product can effectively avoid the destruction of the reducing terminal glycosyl group caused under basic conditions, thereby achieving the relatively regular structure of the reducing terminal of the depolymerized product.

It will be readily understood by those skilled in the art that due to the presence of a reducing agent (such as sodium borohydride) in the reaction solution, the terminal glycosyl group of the depolymerized product obtained from the β-elimination depolymerization can be rapidly reduced to an alditol. On the one hand, the reduction of the reducing terminal glycosyl group to the alditol does not affect the further -elimination reaction of the hexuronic acid ester; on the other hand, after the terminal glycosyl group in the depolymerized product is reduced to the alditol, the destruction and degradation of the reducing terminal glycosyl group under basic conditions can be effectively avoided. Therefore, the β-elimination depolymerization of the FG carboxylate in the presence of a reducing agent can obtain a depolymerized product with a more regular chemical structure.

The "more regular chemical structure" means that: (1) the homologous oligosaccharide compound contained in the depolymerized product is composed of 3m monosaccharide residues; (2) the non-reducing terminal glycosyl group of the homologous oligosaccharide compound is "L-Fuc-(α1-3)-ΔUA-1-", and the reducing terminal glycosyl group is "-3-D-GalNAc-ol".

Thus, the technical feature of the step (b) is that the β-elimination depolymerization reaction is carried out in the presence of a reducing agent, and the β-elimination reaction condition means that the FG carboxylate is treated in a non-aqueous solvent with a strong base. Since the reaction solution for the FG carboxylic acid esterification in the step (a) is a non-aqueous solvent, after the carboxylic acid esterification reaction is completed, the reaction solution will be directly used for the β-elimination depolymerization reaction of the step (b) without further treatment.

In the step (b), the reducing agents are those that can reduce the reducing terminal glycosyl group to an alditol, such as sodium borohydride; the amount of the reducing agent is related to the amount of the depolymerized product formed. Those skilled in the art will appreciate that in order to ensure the yield and structural uniformity of the depolymerized product, a stoichiometric excess of reducing agent should generally be employed in the reaction. On the other hand, the strong base in the step (b) may be optionally a lower sodium alkoxide, a diazabicyclo ring or the like.

The step (c) shown in Scheme 1 comprises converting the homologous oligosaccharide mixture 5 obtained by β-elimination depolymerization of FG to an alkali metal salt, which comprises optionally adding a saturated aqueous solution of an inorganic salt (such as sodium chloride) to the reaction solution. The basic hydrolysis of the carboxylate of the homologous oligosaccharide compound may be generally carried out by treatment with an aqueous solution of an inorganic base (for example, 0.05 M~1 M NaOH or KOH), thereby obtaining a homologous oligosaccharide mixture 6 containing a free carboxyl group.

The step (d) shown in Scheme 1 comprises isolating and purifying the oligosaccharide mixture to obtain a series of purified oligosaccharide compounds 7. In general, the isolation and purification of the oligosaccharide compound by chromatography as described in the step (d) means that the oligosaccharide compound is purified by gel chromatography and/or ion exchange chromatography, and the gel chromatography and/or ion exchange chromatography is a method well known to those skilled in the art. In addition, the gel chromatography and/or ion exchange chromatography may optionally be combined with a technical method such as ultrafiltration or salting out method to increase the efficiency of the isolation and purification.

The step (e) shown in Scheme 1 comprises optionally subjecting the oligosaccharide compound 7 obtained in the step (d) to a further structural modification, thereby obtaining the oligosaccharide compound 8. The compound 8 is a oligosaccharide compound of Formula (I) in which $R_8$ is a group represented by Formula (II), which is equivalent to the oligosaccharide compound represented by the above Formula (V). Wherein:

The oligosaccharide compound 7 is subjected to quaternary ammonium salt conversion, and then reacted with a halogenated hydrocarbon in an organic solvent by a conventional method in the art, to easily obtain an oligosaccharide compound of Formula (V) in which $R_6$ is a C1-C6 aliphatic hydrocarbon group or a C7-C12 aryl group.

By the hydrazinolysis method described in CN 103214591 A and related literature (*Proc Natl Acad Sci USA.* 2015; 112(27): 8284-9), the acetyl group on D-GalNAc in oligosaccharide compound 7 can be removed, to obtain a deacetylated oligosaccharide compound, namely, an oligosaccharide compound of Formula (V) in which $R_7$ is —H. The deacetylated oligosaccharide compound can be reacted with an acid anhydride or $Et_3N·SO_3$ to obtain an N-reacylated or resulfated oligosaccharide compound, namely, an oligosaccharide of Formula (V) in which $R_7$ is a C2-C5 acyl group or —$SO_3H$.

Further, the alcoholic hydroxyl at the C1 position of -D-GalNAc-ol at the reducing terminal of the oligosaccharide compound 7 may optionally be reacted with an alcohol compound under acidic conditions to form a terminal alkylation product. It will be readily understood by those skilled in the art that a compound of Formula (V) in which $R_9$ is a substituted or unsubstituted C1-C6 aliphatic hydrocarbon group or a C7-C12 aryl group can be obtained by the alkylation reaction.

Obviously, by using the above structural modification method in combination, the oligosaccharide compound represented by Formula (V) with various specific structures defined by the present invention can be obtained.

For the preparation method shown in Scheme 1, a preferred embodiment is:

In the step (a), the FG quaternary ammonium salt is N,N-dimethyl-N-[2-[2-[4(1,1,3,3-tetramethylbutyl)phenoxy]ethoxy]ethyl benzammonium salt, namely benzethonium salt; the organic solvent is DMF or a DMF-ethanol mixture; the carboxylate is a benzyl ester; and the "complete or partially conversion into carboxylate" means that the degree of carboxyl esterification of the mixture 3 is in the range from about 30% to about 100%.

In the step (b), the organic solvent is DMF or a DMF-ethanol mixture; the reducing agent is sodium borohydride; and the strong base is sodium ethoxide.

In the step (c), the conversion of the quaternary ammonium salt mixture into an alkali metal salt comprises adding a saturated aqueous solution of sodium chloride to the reaction solution to convert the obtained oligosaccharide homologue 5 into a sodium salt form; the basic hydrolysis in the aqueous solution means that the carboxylate of oligosaccharide compound is hydrolyzed in NaOH aqueous solution with a concentration of 0.05 M~1 M.

In the step (d), the chromatography includes, but is not limited to, gel chromatography and/or ion exchange chromatography;

In the step (e), the further structural modification includes, but is not limited to, carboxyl esterification of D-glucuronic acid group (GlcA) and unsaturated hexuronic acid group (ΔUA) in the oligosaccharide compound; deacetylation and optional reacylation or resulfation of D-acetylgalactosamine group (D-GalNAc); alkylation of alditol at the reducing terminal (D-GalNAc-ol).

It is known that there may be differences in the sulfated form of natural FG from different species sources. Among them, the reported sulfated forms of the FG side chain L-Fuc include 2,4-disulfate (L-$Fuc_{2S4S}$), 3,4-disulfate (L-$Fuc_{3S4S}$), 3-sulfate (L-$Fuc_{3S}$) and 4-sulfate (L-$Fuc_4S$) and no sulfate group substitution; the reported sulfated forms of D-GalNAc in the backbone include 4,6-disulfate (D-$GalNAc_{4S6S}$), 4-sulfate (D-$GalNAc_{4S}$), 6-sulfate (D-$GalNAc_{6S}$) and no sulfate group substitution. Also, some natural FGs may have different sulfated forms of L-FucS and/or D-GalNAcS, while other natural FGs contain a relatively regular and single sulphated form of L-FucS and/or D-GalNAcS (refer to: Pomin V H. *Mar Drugs.* 2014, 12, 232-54).

It can be seen from the preparation method of the oligosaccharide compound of Formula (V) that all the steps do not affect the stability of the sulfate group on the glycosyl group, and thus the sulfated form of the obtained oligosaccharide compound depends on the sulfated form of the natural FG. Obviously, for the natural FG having a relatively regular sulfated form, the type of the oligosaccharide compound in its β-elimination depolymerization product is relatively small, and the oligosaccharide compounds having the same polymerization degree have the same chemical structure, and thus the purified oligosaccharide compound of the present invention can be easily prepared.

For example, in the purified natural FG extracted from the body wall of echinoderms such as *Stichopus variegatus, Bohadschia argus,* and *Stichopus monotuberculatus,* the side chain fucosyl group is mainly L-$Fuc_{2S4S}$, and the hexosamine in its main chain is mainly D-$GalNAc_{4S6S}$. Therefore, these natural FGs are suitable for the preparation of the oligosaccharide compound of Formula (VIII) and a pharmaceutically acceptable salt thereof, and the compound is substantially an oligosaccharide compound of Formula (V) in which $R_1=R_3=R_4=R=-SO_3H$, and $R_2=-H$.

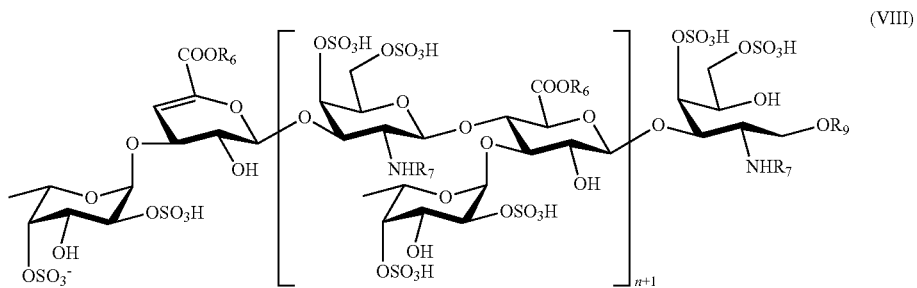

(VIII)

In Formula (VIII), $R_6$, $R_7$ and $R_9$ are as defined above.

In the natural FG extracted from the body wall of echinoderms such as *Holothuria scabra, Holothuria fuscopunctata, Stichopus horrens*, and *Pearsonotheia graeffei*, the side chain fucosyl group is mainly L-Fuc$_{3S4S}$, and the hexosamine in its main chain is mainly D-GalNAc$_{4S6S}$. Therefore, these natural FGs are suitable for the preparation of the oligosaccharide compound of Formula (IX) and a pharmaceutically acceptable salt thereof, and the compound is substantially an oligosaccharide compound of Formula (V) in which $R_1$=—H, and $R_2$=$R_3$=$R_4$=R=—SO$_3$H.

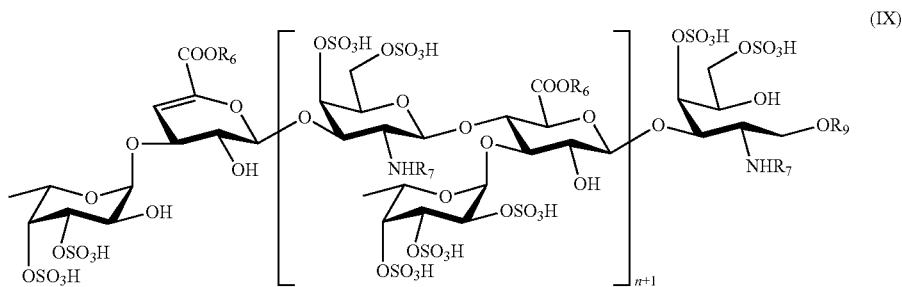

(IX)

In Formula (IX), $R_6$, $R_7$ and $R_9$ are as defined above.

Another preparation method of the oligosaccharide compound of the present invention is a method of the preparation of an oligosaccharide compound having the structure represented by Formula (I) and having $R_8$ as a group represented by the above Formula (III) or (IV). The named "oligosaccharide compound having the structure represented by Formula (I) and having $R_8$ as a group represented by the above Formula (III) or (IV)" is substantially equivalent to an oligosaccharide compound of Formula (VI) or Formula (VII) as defined above. The preparation method comprises "β-elimination depolymerization+peeling reaction": subjecting the carboxylated natural FG to β-elimination depolymerization in an organic solvent in the absence of reducing agent, followed by peeling reaction to make the FG depolymerized product lose the reducing terminal D-GalNAc residue, thereby obtaining a mixture of homologous oligosaccharide compounds having -D-GlcA at the reducing terminal. The method comprise the specific steps of:

(a) converting natural FG into a quaternary ammonium salt form, followed by completely or partially converting the carboxyl group on D-GlcA in the FG quaternary ammonium salt into a carboxylate in an organic solvent;

(b) in an anhydrous organic solvent, treating the FG carboxylate with a strong base to cause β-elimination depolymerization, and then by adding a small amount of aqueous solution of a strong base, subjecting the FG depolymerized product to further "peeling reaction" to lose the -D-GalNAc residue at the reducing terminal, thereby obtaining a mixture of homologous oligosaccharide compounds having -D-GlcA at the reducing terminal;

(c) converting the oligosaccharide mixture obtained in the step (b) into an alkali metal salt, followed by subjecting the carboxylate of the homologous oligosaccharide compounds to basic hydrolysis in an aqueous solution, to obtain a mixture of the homologous oligosaccharide compounds containing a free carboxyl group;

(d) isolating and purifying the oligosaccharide compound in the oligosaccharide mixture of the step (c) by chromatography;

(e) optionally, subjecting a further structural modification to the purified oligosaccharide compound obtained in the step (d).

The products treated in the steps (a) to (e) of the method are as shown in Scheme 2:
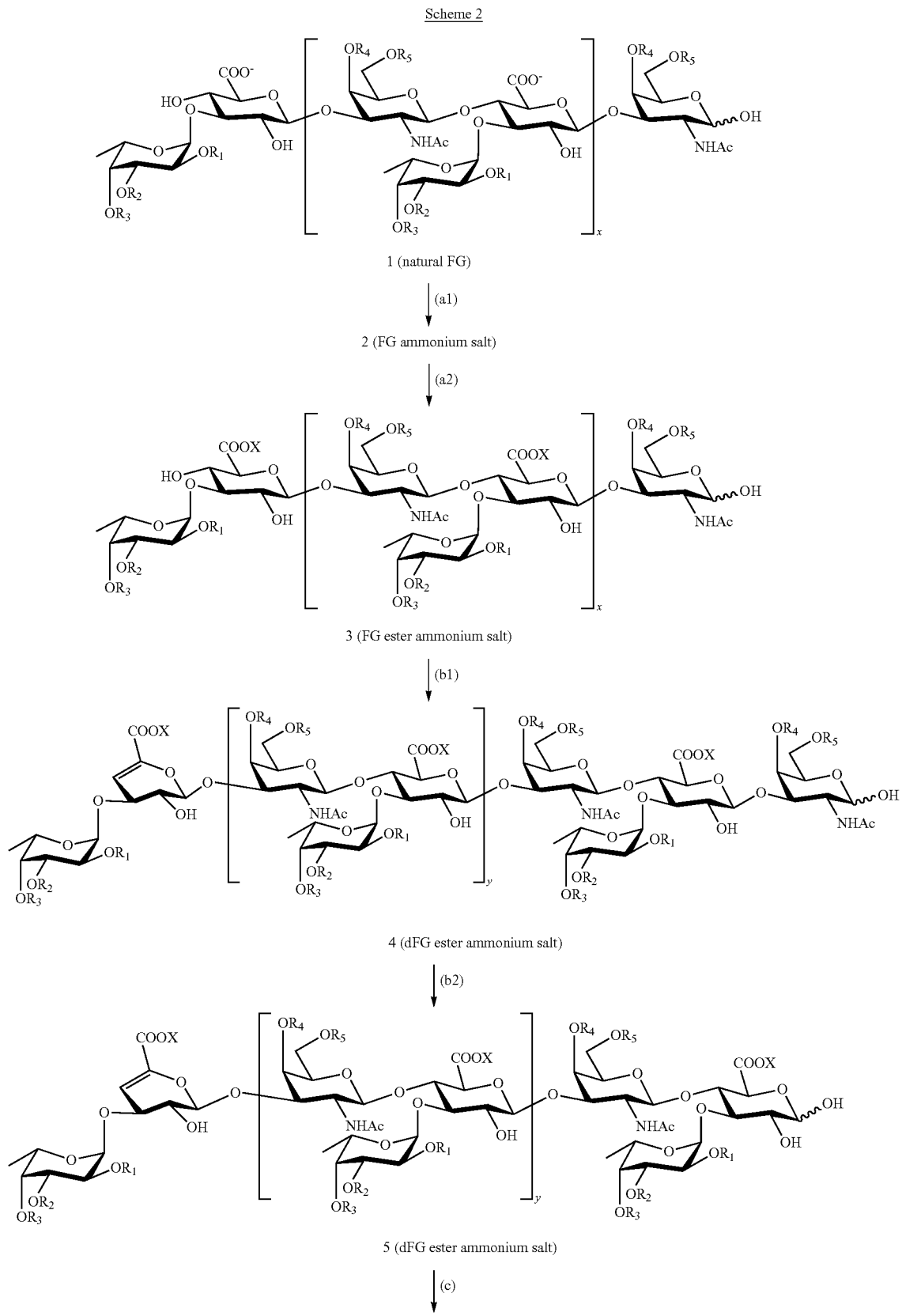
Scheme 2

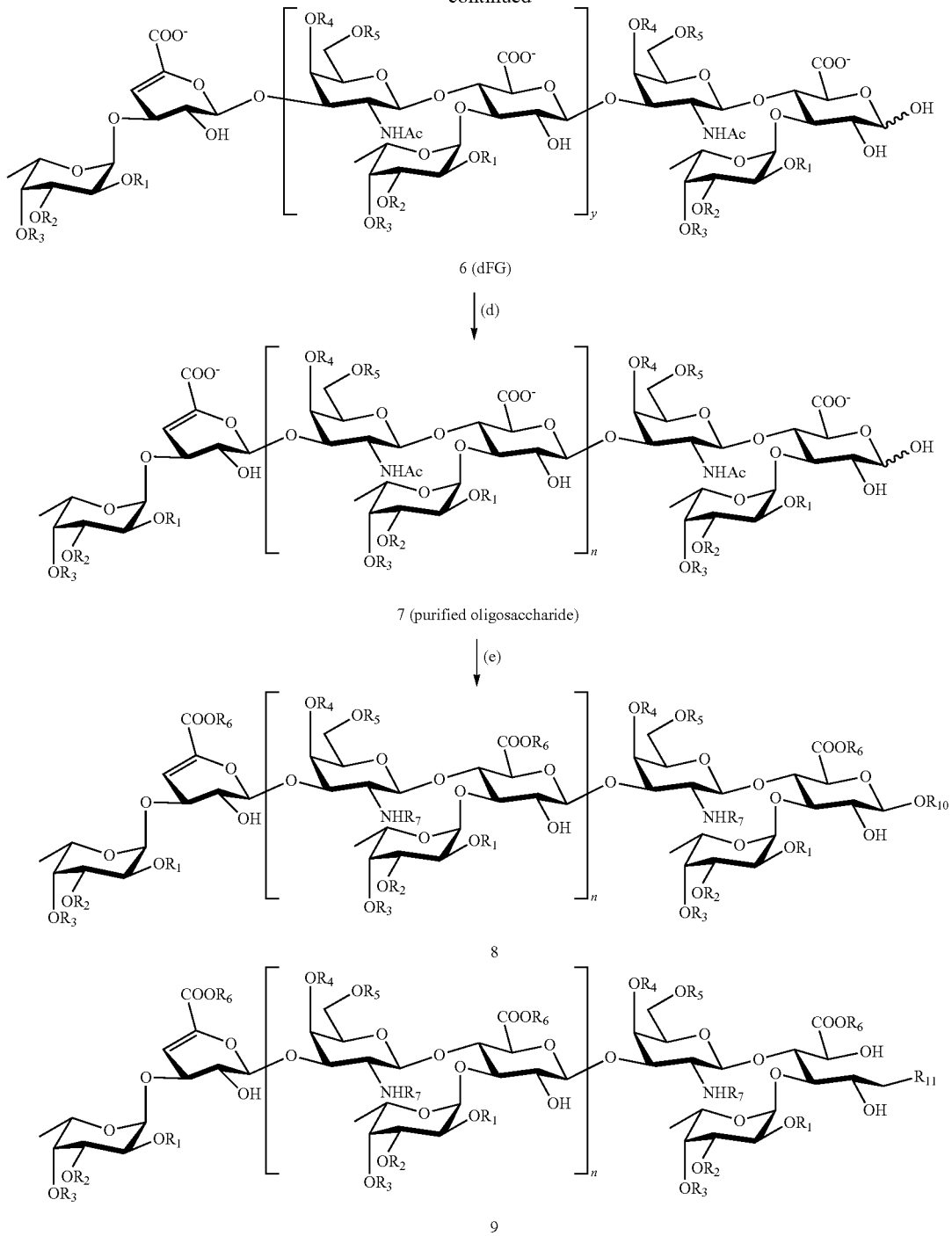

In Scheme 2:

Natural FG 1, FG ammonium salt 2, FG ester ammonium salt 3 and dFG ester ammonium salt 4 are all defined as in Scheme 1;

dFG ester ammonium salt 5 is a depolymerized product having -D-GlcA at the reducing terminal, which is formed by subjecting the depolymerized product 4 to "peeling reaction" to lose the terminal -D-GalNAc. dFG 6 is a hydrolyzate of carboxylate group of 5, which is present in the form of an alkali metal salt. Depolymerized products 4, 5 and 6 are all a mixture of homologous oligosaccharide compounds;

Purified oligosaccharide 7 is a purified oligosaccharide obtained by isolation from the depolymerized product 6; and purified oligosaccharides 8 and 9 are purified oligosaccharides obtained by subjecting 7 to an optional substituent structural modification.

In the chemical structure described in Scheme 2, $R_1$, $R_2$, $R_3$, $R_4$, $R_5$, $R_6$, $R_7$, $R_{10}$, $R_{11}$ and n are defined as in Formula (I) above; x, y and —COOX are defined as in Scheme 1.

The quaternary ammonium salt conversion of the natural FG and the carboxyl esterification of the FG shown in the step (a) of Scheme 2 are the same as the method described in above-mentioned Scheme 1.

The step (b) shown in Scheme 2 comprises subjecting the FG carboxylate to β-elimination depolymerization (b1) to form the depolymerized product 4 (containing a small amount of product 5), followed by "peeling reaction" to remove the D-GalNAc residue (b2) at the reducing terminal and obtain the depolymerized product 5.

As described above, in the β-elimination depolymerization product of the natural FG disclosed in CN 201310099800, both oligosaccharide compound having D-GalNAc at the reducing terminal and some amount of oligosaccharide compound having "-D-GlcA-" at the reducing terminal are present, which may be related to the destruction of the reducing terminal glycosyl group of the β-elimination depolymerization product. Since the structure of the reducing terminal is relatively complicated, it is difficult to isolate and purify an oligosaccharide from the depolymerized product.

It is known to those skilled in the art that a "peeling reaction" under strong base conditions can cause some polysaccharide compounds (such as cellulose) to lose the monosaccharide residues at the reducing terminal one by one (Whistler R L, et al. Alkaline Degradation of Polysaccharides. *Advances in Carbohydrate Chemistry*. 1958, 13: 289-329). In fact, the present inventors have found that when natural FG is depolymerized under the conditions described in CN 201310099800, the resulting product has some amount of by-products containing unsaturated small molecule compounds that are similar to the reported products of the destruction of reducing terminal glycosyl group in the peeling reaction. In view of the fact that the β-elimination reaction of natural FG disclosed in CN 201310099800 is carried out under strong base conditions, it can be inferred that the formation of an oligosaccharide compound having "-D-GlcA-" at the reducing terminal in the depolymerized product may be related to the "peeling reaction" of the depolymerized product.

It will be understood by those skilled in the art that the reduction of the terminal of the depolymerized product into an alditol by addition of a reducing agent to the reaction solution of β-elimination depolymerization is helpful to avoid the occurrence of "peeling reaction"; on the other hand, it is possible to obtain a series of FG oligosaccharides having "-D-GlcA" at the reducing terminal by "peeling reaction" of β-elimination depolymerization product of FG under controlled conditions. Accordingly, the present inventors have surprisingly found through further studies on the β-elimination reaction conditions of the FG carboxylate:

(1) when a small amount of aqueous solution of a strong base (such as NaOH) is added to the basic non-aqueous solution mentioned above, the FG oligosaccharide having "-D-GalNAc" at the reducing terminal is highly susceptible to "peeling reaction" and loses the glycosyl group at the reducing terminal; unexpectedly, the FG oligosaccharide compound having "-D-GlcA" at the reducing terminal is difficult to undergo the similar "peeling reaction".

(2) HPGPC analysis and NMR structural analysis show that when the FG carboxylate is treated with a strong base in an anhydrous organic solvent to cause "β-elimination depolymerization", and then a small amount of aqueous solution of a strong base is added to the reaction solution to further cause "peeling reaction" of the β-elimination depolymerization product, the "homologous oligosaccharide compound" contained in the depolymerized product have a very regular chemical structure, that is, the homologous oligosaccharide compound is composed of (3m−1) monosaccharide residues; the non-reducing glycosyl group of the homologous oligosaccharide compound is "L-Fuc-(α1-3)-ΔUA-1-", and the reducing terminal glycosyl group is "-4-D-GlcA" substituted by L-FucS at the C3 position.

(3) The oligosaccharide homologues obtained by β-elimination depolymerization and peeling reaction of the natural FG carboxylate can be further isolated and purified to obtain a series of "purified oligosaccharide compounds". These purified oligosaccharide compounds have a common chemical structural feature: the oligosaccharide compounds contain (3m−1) monosaccharide residues; the non-reducing terminal is "L-Fuc-(α1-3)-ΔUA-1-", and the reducing terminal is "-4-[L-Fuc-(α1-3)]-D-GlcA".

Therefore, the step (b) first comprises treating the FG carboxylate with a strong base in a non-aqueous solvent in absence of a reducing agent to cause β-elimination depolymerization (b1 of Scheme 2) to obtain the depolymerized product 4 (which may contain a small amount of oligosaccharide 5). Similarly, since the reaction solvent of the FG carboxyl esterification is a non-aqueous solvent, the reaction solution is directly used for the β-elimination depolymerization described in the step (b) without further treatment. In general, the strong base in the step (b) may be optionally a lower sodium alkoxide, a diazabicyclo ring or the like.

The step (b) shown in Scheme 2 further comprises converting the depolymerized product 4 into a depolymerized product 5 by further "peeling reaction" (b2 of Scheme 2), which is performed by adding a small amount of aqueous solution of a strong base to the β-elimination reaction solution. Generally, the aqueous solution of the strong base may be optionally 0.25 M~2 M NaOH, KOH or a saturated $Ca(OH)_2$ aqueous solution; the "small amount" of aqueous solution of a strong base means that the aqueous solution of the strong base is equivalent to about ⅕~ 1/10 of the total volume of the reaction solution.

The step (c) shown in Scheme 2 comprises converting the depolymerized product 5 into an alkali metal salt and hydrolyze the carboxylate, the technical method of which is the same as the method described in Scheme 1;

Similarly, as shown in the step (d) of Scheme 2, a mixture of oligosaccharide compounds 6 is isolated and purified to obtain a series of purified oligosaccharide compounds 7. In general, the purification method refers to gel chromatography and/or ion exchange chromatography, and may optionally be combined with technical methods such as ultrafiltration, salting out method to improve the efficiency of isolation and purification.

Similarly, the step (e) comprises optionally subjecting a further structural modification to the oligosaccharide compound 7 obtained in the step (d), thereby obtaining a purified oligosaccharide compound 8 or 9. Wherein:

The oligosaccharide compound 8 is substantially equivalent to the oligosaccharide compound of Formula (VI) described above, and the compound 9 is substantially equivalent to the oligosaccharide compound of Formula (VII) described above.

The oligosaccharide compound 7 is subjected to quaternary ammonium salt conversion, and followed by reaction with a halogenated hydrocarbon in an organic solvent by a conventional method in the art to obtain an oligosaccharide compound in which $R_6$ is a substituted or unsubstituted C1-C6 hydrocarbon group or a C7-C12 aryl group.

The acetyl group on D-GalNAc in the oligosaccharide compound 7 can be removed by a hydrazinolysis method to obtain a deacetylated oligosaccharide compound. The deacetylated oligosaccharide compound can in turn be reacted with an acid anhydride or $Et_3N·SO_3$ to obtain an N-reacylated or resulfated oligosaccharide compound, namely, an oligosaccharide compound of Formula (VI) or Formula (VII) in which $R_7$ is a C2-C5 acyl or —$SO_3H$.

The reducing terminal -D-GlcA of the oligosaccharide compound 7 can be optionally reacted with an alcohol compound under acidic conditions to form a terminal alkylation product, thereby obtaining the compound of Formula (VI) in which $R_{10}$ is optionally a substituted or unsubstituted C1-C6 hydrocarbon group or C7-C12 aryl group.

The aldehyde group at the C1 position of the -D-GlcA at the reducing terminal of the oligosaccharide compound 7 can be reductively aminated in the presence of an organic amine. The reaction comprises reacting an organic amine with the aldehyde group at the C1 position of the terminal glycosyl group to form a Schiff base, which is reduced to a secondary amine in the presence of a reducing agent, thereby obtaining a compound (9) of Formula (VII) in which $R_{11}$ is —$NHR_{12}$.

The aldehyde group at the C1 position of the -D-GlcA at the reducing terminal of the oligosaccharide compound 7 may be optionally reduced to an alditol -D-GlcA-ol using a reducing agent such as sodium borohydride, and the -D-GlcA-ol may further optionally be reacted with an alcohol compound under acidic conditions to form a terminal alkylation product, thereby obtaining the compound of Formula (VII) (9) in which $R_{11}$ is —$OR_{13}$, and $R_{13}$ is optionally —H, a substituted or unsubstituted C1-C6 hydrocarbon group or a C7-C12 aryl group.

Obviously, the oligosaccharide compound represented by Formula (VI) or Formula (VII) having various specific structures defined by the present invention may be obtained by using the above structural modification method in combination.

For the preparation method shown in Scheme 2, a preferred embodiment is:
in the step (a), the FG quaternary ammonium salt is benzethonium salt; the organic solvent is DMF or a DMF-ethanol mixture; the carboxylate is a benzyl ester, and "converting all or part to carboxylate" means that the degree of carboxyl esterification of Compound 3 is in the range of from about 30% to about 100% in the step (b), the organic solvent is DMF or a DMF-ethanol mixture, and the strong base is sodium ethoxide.

in the step (c), the conversion of the quaternary ammonium salt mixture to the alkali metal salt means that a saturated aqueous solution of sodium chloride is added to the reaction solution, thereby converting the obtained oligosaccharide homologues into a sodium salt form; the basic hydrolysis in the aqueous solution means that the carboxylate of the homologous oligosaccharide compound is hydrolyzed in NaOH aqueous solution with a concentration of 0.05 M to 1 M.

in the step (d), the chromatography includes, but is not limited to, gel chromatography and/or ion exchange chromatography.

in the step (e), the further structural modification includes, but is not limited to, carboxyl esterification of D-GlcA and ΔUA in the oligosaccharide compound; deacetylation and optionally reacylation or resulfation of D-GalNAc; alkylation, reduction, reductive amination or reductive alkylation of the hemiacetal at the C1 position of the reducing terminal -D-GlcA.

Similarly, in the preparation method of the oligosaccharide compound described in Scheme 2, the sulfated form of the obtained oligosaccharide compound also depends on the sulfated form of the natural FG.

Therefore, natural FG derived from echinoderma such as *Stichopus variegatus, Stichopus horrens*, and *Stichopus monotuberculatus* is suitable for the preparation of the oligosaccharide compound of Formula (X) and Formula (XI) and a pharmaceutically acceptable salt thereof, and the compound is substantially an oligosaccharide compound of Formula (VI) and Formula (VII) in which $R_1=R_3=R_4=R_5=$—$SO_3H$, and $R_2=$—H.

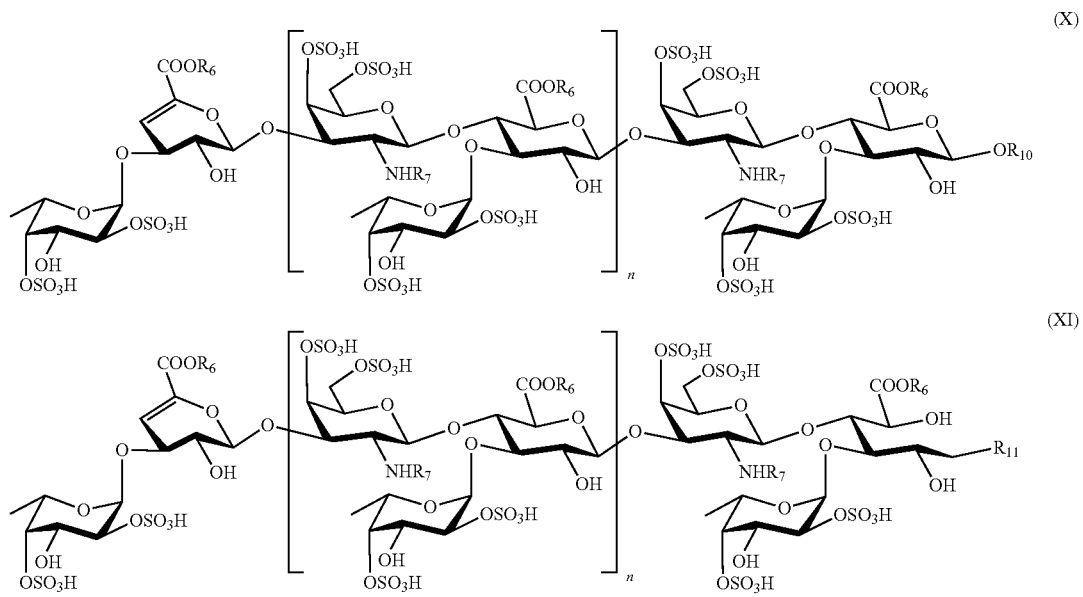

In Formula (X) and Formula (XI), $R_6$, $R_7$, $R_{10}$ and $R_{11}$ are defined as above.

However, natural FG from echinoderms such as *Holothuria scabra*, *Holothuria fuscopunctata* and *Pearsonotheia graeffei* is suitable for the preparation of the oligosaccharide compound of Formula (XII) and Formula (XIII), and the compound is substantially an oligosaccharide compound of Formula (VI) and Formula (VII) in which $R_1$=—H, and $R_2$=$R_3$=$R_4$=$R_5$=—$SO_3^-$.

distribution is obtained by post-treatment and optional further substituent structure modifications.

As described above, by treating natural product FG according to the steps (a) to (c) shown in Scheme 1, a homologous oligosaccharide mixture having L-FucS-(α1-3)-ΔUA-1- at the non-reducing terminal and -D-GalNAcS at the reducing terminal can be obtained. Similarly, in the preparation method of the oligosaccharide mixture of the present invention, one of the methods is that: FG carboxylate

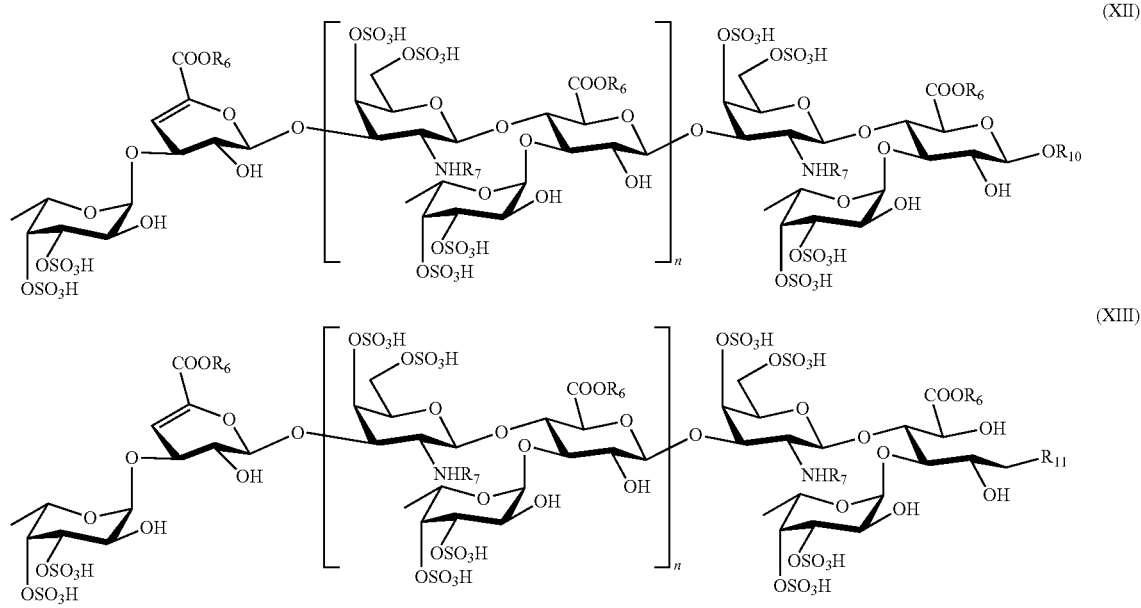

In Formula (XII) and Formula (XIII), $R_6$, $R_7$, $R_{10}$ and $R_{11}$ are defined as above.

Obviously, the β-elimination reaction of natural FG under the technical conditions of the present invention can also be used to prepare a mixture of FG oligosaccharide compounds with more regular chemical structure.

Therefore, the present invention further provides a method for the preparation of the oligosaccharide mixture of the present invention and a pharmaceutically acceptable salt thereof. Wherein, (1) the mixture is composed of a homologue of the oligosaccharide compound having the structure represented by Formula (I) defined in the specification, and in the homologous oligosaccharide compounds of the structure of Formula (I), $R_8$ is the group simultaneously represented by Formula (II), simultaneously represented by Formula (III) or simultaneously represented by Formula (IV). Specifically, in the molar ratio, the ratio of the oligosaccharide compound of Formula (I) in which $R_8$ is the group simultaneously represented by Formula (II), or simultaneously represented by Formula (III) or simultaneously represented by Formula (IV) accounts for no less than 95% in the mixture. In the preparation method, natural FG is used as the starting material, and optionally, FG carboxylate is subjected to β-elimination depolymerization and terminal "reduction reaction" in the presence of a strong base and a reducing agent to obtain a mixture of homologous oligosaccharide compounds; or FG carboxylate is subjected to "β-elimination depolymerization" and terminal "peeling reaction" in the presence of a strong base to obtain a mixture of homologous oligosaccharide compounds. Then, the oligosaccharide mixture with the desired molecular weight is subjected to β-elimination depolymerization and terminal "reduction reaction" in the presence of a strong base and a reducing agent to obtain a mixture of homologous oligosaccharide compounds; the homologous oligosaccharide compound contained in the obtained oligosaccharide mixture has the general structure represented by Formula (I) defined above, and wherein $R_8$ is a group represented by Formula (II) defined above. The method comprises the specific steps of:

(a) converting the natural FG into a quaternary ammonium salt form, and in an organic solvent, completely or partially converting the carboxyl group on hexuronic acid residue in the obtained FG into a carboxylate;

(b) in an organic solvent, subjecting the FG carboxylate to β-elimination depolymerization and terminal reduction reaction in the presence of a reducing agent and a strong base, thereby obtaining a mixture of homologous oligosaccharide compound having -D-GalNAc-ol at the reducing terminal;

(c) converting the oligosaccharide mixture obtained in the step (b) into an alkali metal salt, and subjecting the carboxylate of the homologous oligosaccharide compound to basic hydrolysis in an aqueous solution, to obtain a mixture of the homologous oligosaccharide compound containing a free carboxyl group, and performing appropriate post-treatment;

(d) optionally subjecting the oligosaccharide mixture obtained in the step (d) to a further substituent structural modification.

In a preferred embodiment:

In the step (a), the quaternary ammonium salt is benzethonium salt; the organic solvent is DMF or a DMF-ethanol mixture; the carboxylate is a benzyl ester; and the "complete or partial conversion into carboxylate" means that the degree of carboxyl esterification in FG is in the range from about 30% to about 100%.

In the step (b), the organic solvent is DMF or a DMF-ethanol mixture; the reducing agent is sodium borohydride; and the strong base is sodium ethoxide.

In the step (c), the conversion of the quaternary ammonium salt mixture to the alkali metal salt comprises adding a saturated aqueous solution of sodium chloride to the reaction solution to convert the obtained oligosaccharide homologue into a sodium salt form; the basic hydrolysis in the aqueous solution comprises hydrolyzing the carboxylate of oligosaccharide compounds in NaOH aqueous solution with a concentration of 0.05 M~1 M.

As described above, the natural FG prepared according to the methods in the prior art also typically contains some amount of fucan, glycogen, and hexosamine-containing polysaccharide, which have a molecular weight distribution similar to FG. These polysaccharide compositions have a small change in molecular weight after being treated by the above steps (a) and (b). Therefore, in the post-treatment step described in the step (c), these polysaccharide impurities can be easily removed by ultrafiltration method, dialysis method or gel chromatography.

As shown in the above Scheme 1, the depolymerized product obtained by β-elimination depolymerization and terminal reduction treatment may also have a broader molecular weight distribution (in the oligosaccharide mixture 6 shown in Scheme 1, n may be an integer of about 0-15). Therefore, in the post-treatment step of the step (c), ultrafiltration method, dialysis method or gel chromatography treatment may be selected to remove the oligosaccharide with a higher degree of polymerization and the small molecule compounds, thereby obtaining an oligosaccharide mixture with desired molecular weight distribution.

In the step (d), the further substituent structural modification includes, but is not limited to, carboxyl esterification of D-GlcA and unsaturated ΔUA in the oligosaccharide compounds; deacetylation and optional further reacylation or resulfation of D-GalNAc; hydroxyalkylation at the C1 position of the reducing terminal D-GalNAc-ol.

Obviously, compared with the oligosaccharide mixture described in the invention patent ZL 201310099800, the homologous oligosaccharide mixture in which $R_8$ is a group of Formula (II) according to the present invention has a more regular chemical structure. In the oligosaccharide compound contained in the former, about 10% to 30% of the oligosaccharide compounds have D-GlcA (or a derivative thereof) at the reducing terminal, and the remaining oligosaccharide compounds have D-GalNAc (or a derivative thereof) at the reducing terminal, however, the oligosaccharide compounds contained in the oligosaccharide mixture of the present invention have D-GalNAc (or a derivative thereof) at the reducing terminal, and there is no or only a trace amount of oligosaccharide compound having D-GlcA (or a derivative thereof) at the reducing terminal.

Further, as can be seen from the above, by treating the natural product FG according to the steps (a)~(c) shown in Scheme 2, a homologous oligosaccharide mixture having L-FucS-(α1-3)-ΔUA-1- at the non-reducing terminal and the -D-GlcA at the reducing terminal can be obtained. Therefore, in the preparation method of the oligosaccharide mixture of the present invention, another method comprises: subjecting the FG carboxylate to "β-elimination depolymerization" and terminal "peeling reaction" in the presence of a strong base to obtain a mixture of homologous oligosaccharide compounds; the homologous oligosaccharide compounds contained in the obtained oligosaccharide mixture have a general structure represented by Formula (I) as defined in the specification of the present invention, and $R_8$ is a group represented by Formula (III) or Formula (IV) defined above. The method comprises the specific steps of:

(a) converting the natural FG into a quaternary ammonium salt form, and in an organic solvent, converting all or part of the carboxyl group on the hexuronic acid residue in the obtained FG into a carboxylate;

(b) in an anhydrous organic solvent, treating the FG carboxylate with a strong base to cause β-elimination depolymerization, followed by adding a small amount of aqueous solution of a strong base, subjecting the FG depolymerized product to further "peeling reaction" to lose the -D-GalNAc residue at the reducing terminal, thereby obtaining a mixture of homologous oligosaccharide compounds having -D-GlcA at the reducing terminal.

(c) converting the oligosaccharide mixture obtained in the step (b) into an alkali metal salt, and subjecting the carboxylate of the homologous oligosaccharide mixture in an aqueous solution to basic hydrolysis, to obtain a mixture of the homologous oligosaccharide compounds containing a free carboxyl group, and performing appropriate post-treatment;

(d) optionally subjecting the oligosaccharide mixture obtained in the step (c) to a further substituent structural modification.

In a preferred embodiment:

In the step (a), the quaternary ammonium salt is a benzethonium salt; the organic solvent is DMF or a DMF-ethanol mixture; the carboxylate is a benzyl ester; and the degree of carboxyl esterification of the FG carboxylate is in the range from about 30% to about 100%.

In the step (b), the organic solvent is DMF or a DMF-ethanol mixture; and the strong base is sodium ethoxide; the small amount of aqueous solution of a strong base refers to a 1 M~2 M NaOH aqueous solution that is equivalent to about 1/5 to 1/10 of the total volume of the reaction solution.

In the step (c), the conversion of the quaternary ammonium salt mixture to the alkali metal salt comprises adding a saturated aqueous solution of sodium chloride to the reaction solution to convert the obtained oligosaccharide homologue into a sodium salt form; the basic hydrolysis in the aqueous solution means that the carboxylate of the oligosaccharide compounds is hydrolyzed in NaOH aqueous solution with a concentration of 0.05 M~1 M. Similarly, in the post-treatment, gel chromatography, ultrafiltration and/or dialysis may be optionally used to remove the undepolymerized macromolecular polysaccharide impurities and remove the highly polymerized oligosaccharide compounds and small molecular impurities, and thus obtain an oligosaccharide mixture of the desired molecular weight range.

In the step (d), the further substituent structural modification includes, but is not limited to, carboxyl esterification of D-GlcA and ΔUA in the oligosaccharide compounds; deacetylation and optional further reacylation or resulfation of D-GalNAc; alkylation, reduction, reductive amination or reductive alkylation of the hemiacetal at the C1 position of the reducing terminal -D-GlcA.

Similarly, compared with the oligosaccharide mixture described in the invention patent ZL 201310099800, the homologous oligosaccharide mixture in which $R_8$ is a group of Formula (III) or Formula (IV) according to the present invention has a more regular chemical structure. In the oligosaccharide compounds contained in the former, about 10% to 30% of the oligosaccharide compounds have D-GlcA (or a derivative thereof) at the reducing terminal, and the remaining oligosaccharide compounds have D-GalNAc (or a derivative thereof) at the reducing terminal; however, the oligosaccharide compounds contained in the oligosaccharide mixture of the present invention have D-GlcA (or a derivative thereof) at the reducing terminal, and have no or only a trace amount of oligosaccharide compounds having D-GalNAc (or a derivative thereof) at the reducing terminal.

Obviously, using the natural FG derived from an echinoderma such as *S. variegatus, S. horrens* and *S. monotuberculatus* as a starting material, according to the preparation method of the oligosaccharide mixture described in present invention, the mixture of homologous oligosaccharide compounds of Formula (VIII), Formula (X) and Formula (XI) described above can be prepared. Using the natural FG derived from echinoderma such as *H. Scabra, H. Fuscopunctata* and *P. graeffei* as a starting material, according to the preparation method of the oligosaccharide mixture described in present invention, the mixture of homologous oligosaccharide compounds of Formula (IX), Formula (XII) and Formula (XIII) described above can be prepared.

The available data show that in a homologous oligosaccharide compound obtained by deacylated-deaminated depolymerization of the natural FG containing a L-Fuc$_{2S4S}$ side chain substituent, nonasaccharide (NSac) is the smallest structural fragment with potent inhibitory activity of factor Xase (Zhao L Y et al., *PNAS*, 2015, 112: 8284-8289.). The present inventors have conducted a structure-activity relationship study on the activity of the intrinsic factor Xase (factor Xase derived from human and experimental animals) of the purified oligosaccharide of the present invention and found that:

(1) The oligosaccharide compounds of the present invention have a selective activity of inhibiting intrinsic factor Xase. In general, using an in vitro enzyme activity assay, the IC$_{50}$ value of the oligosaccharide compounds inhibiting Factor Xase of the present invention may be in the range of about 5 to 200 ng/ml. The selective inhibition of the activity of the intrinsic factor Xase means that in the presence or absence of antithrombin (AT), these oligosaccharide compounds, at a concentration of significantly inhibiting Xase, have no significant effect on the activity of coagulation factors and platelets, but may have a certain intensity of heparin cofactor II (HC-II)-dependent IIa inhibitory activity.

(2) For a series of oligosaccharide compounds containing 3m monosaccharide groups and having ΔUA at the non-reducing terminal and -D-GalNAc-ol at the reducing terminal, the minimum structural fragment that potently inhibits Xase activity is also nonasaccharide (NSac). The results show that the glycosyl structure changes at the non-reducing terminal and the reducing terminal has little effect on the inhibitory activity of factor Xase.

(3) For a series of oligosaccharide compounds containing (3m−1) monosaccharide residues and having -D-GlcA (-ol) at the reducing terminal, the minimum structural fragment for potent inhibitory activity of factor Xase is octasaccharide (OSac). The results suggest that the reducing terminal -D-GalNAc-ol in the above NSac may not be an essential structure for its potent inhibitory activity of factor Xase.

(4) In general, the oligosaccharide compounds of the present invention having a degree of polymerization of not less than OSac have potent intrinsic factor Xase inhibitory activity (IC$_{50}$ values are less than about 100 ng/ml); the oligosaccharides having a higher degree of polymerization have a slightly enhanced activity.

(5) In the oligosaccharide compounds of the present invention, hexasaccharide or pentasaccharide at a higher concentration may have a certain inhibitory activity against intrinsic Xase, although the activity intensity thereof is relatively weak; further, hexasaccharide and pentasaccharide also have a certain intensity of heparin cofactor II (HC-II)-dependent IIa inhibitory activity.

(6) In the oligosaccharide compounds of the present invention, the substituent structural modification can significantly affect the physicochemical properties of the oligosaccharide compounds, such as water solubility and oil-water partition coefficient, but generally have a small effect on its coagulation factor inhibitory activity and anticoagulant and antithrombotic activity.

(7) The oligosaccharide compounds of the present invention may have significant anticoagulant activity for inhibiting intrinsic coagulation pathway, based on prolonging the activated partial thromboplastin time (APTT) of human normal plasma, the concentration of the drug required for multiplying APTT is generally in the range of about 2~18 μg/mL. And the oligosaccharide compounds of the present invention have no significant effect on extrinsic coagulation.

(8) In the pathological model of the experimental animals, the oligosaccharide compounds of the present invention can significantly inhibit arteriovenous thrombosis. For example, the inventors' researches show that in various experimental animal models, based on the weight of the thrombus, when a compound of the present invention (such as nonasaccharide or octasaccharide) is administered subcutaneously (sc) or intravenously (iv) at a dose of about 2 mg/kg~20 mg/kg, the inhibition rate on experimental venous thrombosis (for example, caused by inferior vena cava ligation) may reach 70%~100%. And at an equivalent antithrombotic dose, the effect of the oligosaccharide compound on bleeding time and bleeding volume may be significantly lower than that of low molecular weight heparin drugs used clinically.

(9) The oligosaccharide mixture of the present invention has an inhibitory activity against intrinsic factor Xase and an anticoagulant and antithrombotic activity, which is similar to a purified oligosaccharide compound.

In summary, the oligosaccharide compounds of the present invention and mixtures thereof have significant anticoagulant and antithrombotic activity, and when the degree of oligosaccharide polymerization is not lower than that of octasaccharide, both the oligosaccharide compounds of the present invention and the mixture thereof are an intrinsic factor Xase inhibitor with good selectivity. Existing research data show that intrinsic coagulation pathway is closely related to pathological thrombosis, and may not be necessary for physiological hemostasis. Selective intrinsic coagulation pathway inhibitors may inhibit pathological thrombosis, and bleeding tendency may be effectively reduced. Since factor Xase is the terminal and rate-limiting enzyme active site of the intrinsic coagulation pathway, intrinsic factor Xase has become a drug target for the development of anticoagulant and antithrombotic drugs with low bleeding tendency.

In view of the significant anticoagulant and antithrombotic activity of the oligosaccharide and the oligosaccharide mixture of the present invention, these oligosaccharide and oligosaccharide mixture should have clinical application value of prevention and/or treatment of thrombotic diseases. Therefore, the present invention further provides a pharmaceutical composition comprising the oligosaccharide or the oligosaccharide mixture.

First, the present invention provides a pharmaceutical composition having antithrombotic activity. The pharmaceutical composition comprises an effective antithrombotic dose of the oligosaccharide compound of the present invention or a pharmaceutically acceptable salt thereof, and a pharmaceutically acceptable excipient. Wherein, the oligosaccharide compound refers to a compound having the structure represented by Formula (I) as defined in the present invention.

In view of the physicochemical properties of the oligosaccharide compounds of the present invention, the pharmaceutical composition of the present invention is preferably prepared into a parenteral dosage form, such as an aqueous solution for injection or a lyophilized preparation formulated as an aqueous solution for injection before use, and may also be a spray administered by the respiratory tract, or a transdermal patch, a paste or a gel for transdermal administration, and so on.

The oligosaccharide compounds of the present invention generally have good water solubility and are easily formulated into aqueous solutions; since the active ingredients have low molecular weights, pathogenic microorganisms and pyrogens may be removed by ultrafiltration; the optional pharmaceutical excipients for the aqueous solution and/or lyophilized preparation may include inorganic salts such as sodium chloride, buffer salts for adjusting the osmotic pressure and/or pH of the solution, and preferably include no co-solvent and/or surfactant. For the lyophilized powder formulated into liquid injection before use, besides the inorganic salt and/or buffer salt, a pharmaceutically acceptable excipient which facilitates formulation of the preparation such as mannose may be selected.

In general, the oral bioavailability of the oligosaccharide compounds is relatively limited, but the oligosaccharide compounds of the present invention (especially the oligosaccharides obtained by substituent structural modifications) may still have certain pharmacodynamic activity when administered by the gastrointestinal tract. Thus, the pharmaceutical compositions of the present invention may also be formulated into gastrointestinal dosage forms well known to those skilled in the art, such as a tablet, a capsule.

Those skilled in the art will appreciate that for the pharmaceutical composition in a particular formulation form, the effective antithrombotic dose of the oligosaccharide compound and its pharmaceutically acceptable salt is related to the factors such as the dosage form, the route of administration, and the weight and physiological state of the patient. In general, in the unit preparation form of the pharmaceutical composition of the present invention, the content of the oligosaccharide active ingredient is in the range of about 5 mg~100 mg; in the unit preparation form of the preferred pharmaceutical composition, the content of the oligosaccharide as an active ingredient may be in the range of about 20 mg~80 mg.

Similarly, the present invention also provides a pharmaceutical composition having antithrombotic activity. The pharmaceutical composition comprises a potent antithrombotic dose of the oligosaccharide mixture of the present invention or a pharmaceutically acceptable salt thereof, and a pharmaceutically acceptable excipient.

For the pharmaceutical composition comprising the oligosaccharide mixture of the present invention, the preparation form and dosage selection associated with the administration route are similar to that of the oligosaccharide-containing pharmaceutical composition mentioned above. For example, a preferred administration route is parenteral administration, especially subcutaneous injection administration or intravenous injection administration; a preferred preparation form is aqueous solution for injection or a lyophilized powder for injection; in a unit dosage form of a preferred pharmaceutical composition, the oligosaccharide as an active ingredient may be present in an amount ranging from about 20~100 mg.

The oligosaccharide compound, the oligosaccharide mixture and the pharmaceutically acceptable salt thereof of the present invention have potent anticoagulant and antithrombotic activity and may be used for the prevention and treatment of thrombotic diseases, such as thrombotic cardiovascular diseases, thrombotic cerebrovascular disease, pulmonary vein thrombosis, peripheral venous thrombosis, deep vein thrombosis, peripheral arterial thrombosis. Therefore, the present invention also provides the use of the oligosaccharide compound and/or oligosaccharide mixture and a pharmaceutically acceptable salt thereof in the preparation of a medicament for the treatment and/or prevention of thrombotic diseases. The thrombotic diseases include, but are not limited to, venous thrombosis, arterial thrombosis and/or ischemic cardiovascular and cerebrovascular diseases.

Similarly, the present invention further provides the use of the pharmaceutical composition comprising the oligosaccharide compound and/or oligosaccharide mixture and a pharmaceutically acceptable salt thereof for the preparation of a medicament for treating and/or preventing thrombotic diseases. The thrombotic diseases include, but are not limited to, venous thrombosis, arterial thrombosis, and/or ischemic cardiovascular and cerebrovascular diseases.

Abbreviations

| | | |
|---|---|---|
| FG | Fucosylated glycosaminoglycan | Fucosylated glycosaminoglycan |
| L-Fuc (F) | L-fucose | L-fucose |
| L-FucS | Sulfated fucose | L-fucose sulfate |
| L-Fuc2S4S | L-2,4-bis-O-sulfo-fucose | L-fucose-2,4-disulfate |
| L-Fuc3S4S | L-3,4-bis-O-sulfo-fucose | L-fucose-3,4-disulfate |
| D-GalNAc (A) | β-D-N-acetyl-2-deoxy-2-amino-galactose (D-N-acetylgalactosamine) | D-N-acetyl-2-deoxy-2-amino-galactose (D-acetylgalactosamine) |
| D-GalNAc-ol | β-D-N-acetyl-2-deoxy-2-amino-galactitol | D-N-acetyl-2-deoxy-2-amino-galactitol |
| D-GalNAcS | D-GalNAc sulfate | D-acetylgalactosamine sulfate |
| D-GalNAc4S6S | D-acetylgalactosamine-4,6-disulfate | D-acetylgalactosamine-4,6-disulfate |
| D-GlcA (U) | D-glucuronic acid | D-glucuronic acid |

| | | |
|---|---|---|
| ΔUA (ΔU) | L-4-deoxy-threo-hex-4-enopyranosyluronic acid (4,5-unsaturated hexenuronic acid) | 4-deoxy-L-threo-hex-4-enopyranosyluronic acid (unsaturated hexenuronic acid) |
| Xase | tenase complex | Factor X enzyme complex |
| HC-II | heparin cofactor II | heparin cofactor II |
| APTT | activated partial thromboplastin time | activated partial thromboplastin time |
| PT | prothrombin time | prothrombin time |
| TT | thrombin time | thrombin time |
| NSac | nonasaccharide | nonasaccharide |
| OSac | octasaccharide | octasaccharide |
| DMSO | dimethyl sulfoxide | dimethyl sulfoxide |
| DMF | N,N-Dimethylformamide | N,N-Dimethylformamide |

DESCRIPTION OF THE DRAWINGS

FIG. 14. Effect of A2 and D1 on thrombosis of the inferior vena cava in

DETAILED DESCRIPTION OF THE INVENTION

Figure 1:
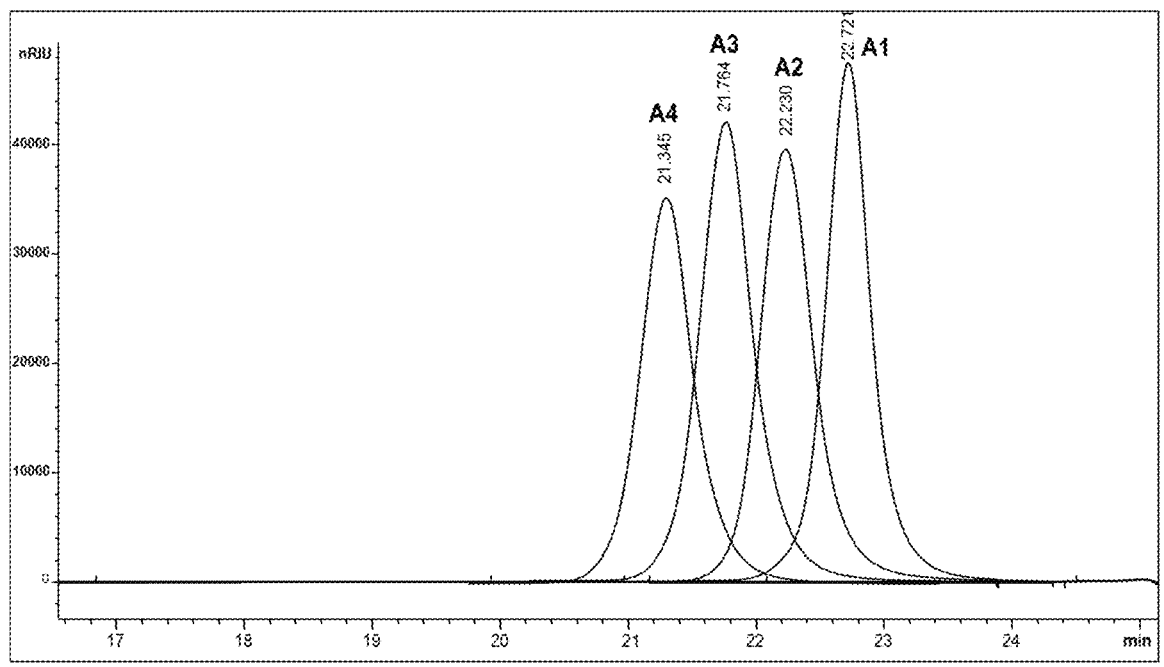
FIG. 1. HPGPC profiles of Compounds A1~A4

The following examples are intended to describe the contents of the present invention in detail, but do not limit the scope of the present invention.

Example 1

Preparation of Compounds A1, A2, A3, A4 and A5

L-2,4-disulfated fucosyl-($\alpha$1→3)-L-4-deoxy-threo-hex-4-enepyranosyluronic acid-($\alpha$1→3)-{-D-N-acetyl-2-deoxy-2-amino-4,6-disulfated galactosyl-($\beta$1→4)-[L-2,4-disulfated fucosyl-($\alpha$1→3)]-D-glucuronyl-($\beta$1→3)}$_{(n+1)}$-D-N-acetyl-2-deoxy-2-amino-4,6-disulfated galactitol (n=0, 1, 2, 3 and 4; hexasaccharide, nonasaccharide, dodecasaccharide, pentadecasaccharide and octadecasaccharide)

1.1 Materials

SvFG, Natural FG (sodium salt) from *Stichopus variegatus*, which was prepared according to the literature method (Zhao L Y et al., *PNAS*, 2015, 112: 8284-8289), with a purity of 98% (HPGPC, area normalization method) and a weight average molecular weight (Mw) of about 70 kDa.

The reagents used such as benzethonium chloride, benzyl chloride, DMF, sodium hydroxide, sodium chloride, and ethanol were all commercially available analytical reagents.

Sephadex G10, medium (50-100 μm), GE Healthcare; Bio-Gel P-6/P-2 gel, fine (45-90 μm), Bio-Rad; Bio-Gel P-10 gel, medium (90-180 μm), Bio-Rad; HPLC Chromatograph, Agilent 1200/1260 Series Chromatograph.

1.2 Methods (1) Quaternary ammonium salt conversion of SvFG: 2.0 g of SvFG was dissolved in 30 mL of deionized water; and 5.0 g of benzethonium chloride was dissolved in another 80 mL of deionized water. The SvFG solution was titrated with the benzethonium chloride solution with stirring to give a white precipitate. The obtained precipitate was washed three times with 55 mL of deionized water and dried under vacuum to give 5.34 g of SvFG quaternary ammonium salt.

(2) Carboxyl esterification of SvFG: The SvFG quaternary ammonium salt obtained in the step (1) was placed in a round bottom flask, dissolved in 26 mL of DMF, then added with 0.769 mL of benzyl chloride, reacted at 35° C. for 24 h with stirring; and allowed to stand and let the solution cool to room temperature (25° C.). The product sample was taken for $^1$H NMR detection and the degree of carboxyl esterification of the FG was calculated to be about 41%.

(3) β-elimination depolymerization in the presence of a reducing agent: a freshly prepared 8.9 mL of 0.08 M sodium ethoxide-ethanol solution (containing 0.4 M NaBH$_4$) was added to the reaction solution of the step (2), and stirred for 30 min.

(4) Sodium salt conversion and carboxyl ester hydrolysis of the depolymerized product: 35 mL of a saturated NaCl solution and 284 mL of absolute ethanol were added to the reaction solution of the step (3), centrifuged at 4000 rpm×10 min to obtain a precipitate. The obtained precipitate was dissolved in 90 mL of water, added with 1.5 mL of 6 M NaOH solution, and stirred at room temperature for 30 min, and then dropwise added with 6 M HCl to neutralize the reaction solution (pH~7.0). The reaction solution was filtered through a 0.45 μm filter, and the obtained filtrate was desalted by a G10 gel column chromatography and lyophilized to obtain a total of 1.059 g of depolymerized product dSvFG (depolymerized SvFG) (yield 53%).

(5) Isolation and purification of Compounds A1~A5: 1 g of dSvFG was dissolved in 10 mL of 0.2 M NaCl, loaded on a Bio-Gel P-10 gel column (Ø2 cm, 1 200 cm), eluted with 0.2 M NaCl solution at a flow rate 10 mL/h, and the eluate fractions of 2.5 mL/tube were collected. The eluate fractions were monitored and the elution profiles were plotted by the cysteine-sulfuric acid method, and the eluate fractions having the same compositions were combined. Purity was determined by HPGPC method (TSK gel G2000SW XL, Ø 7.8 mm×1 300 mm column). Unpurified samples were further purified on a Bio-Gel P-10 gel column. Purified oligosaccharides were desalted on a Sephadex G-10 or Bio-Gel P-2 gel column and then lyophilized.

(6) Spectral analysis: $^1$H—/$^{13}$C— and 2D-NMR were detected using Bruker DRX 800 MHz NMR spectrometer with a spectral width of 16025.6 Hz, an acquisition time of 2.0447 s, a pulse width of 9.5 s, a relaxation time of 1 s, and a scan of 32 times. The sample had a concentration of (10-15) g/L, and was repeatedly lyophilized three times with heavy water before the test; ESI-Q-TOF MS was analyzed by micrOTOF-QII ESI-MS (Bruker, Germany) mass spectrometer. The mass spectrometry conditions were: capillary voltage 2500 V, nebulizer voltage 0.6 bar, dry gas flow rate 4.0 L/min, dry gas temperature +180° C., m/z scan range 50~3000. Data were analyzed using Bruker Compass Data-Analysis 4.0 (Bruker-Daltonics, Germany) software.

1.3 Results (1) Compound A1 35 mg, A2 45 mg, A3 55 mg, A4 35 mg, and A5 20 mg were obtained by the method described, and the purity was determined to be about 99% by HPGPC method. The HPGPC patterns of oligosaccharide compounds A1~A5 are shown in FIG. 1.

Figure 2:
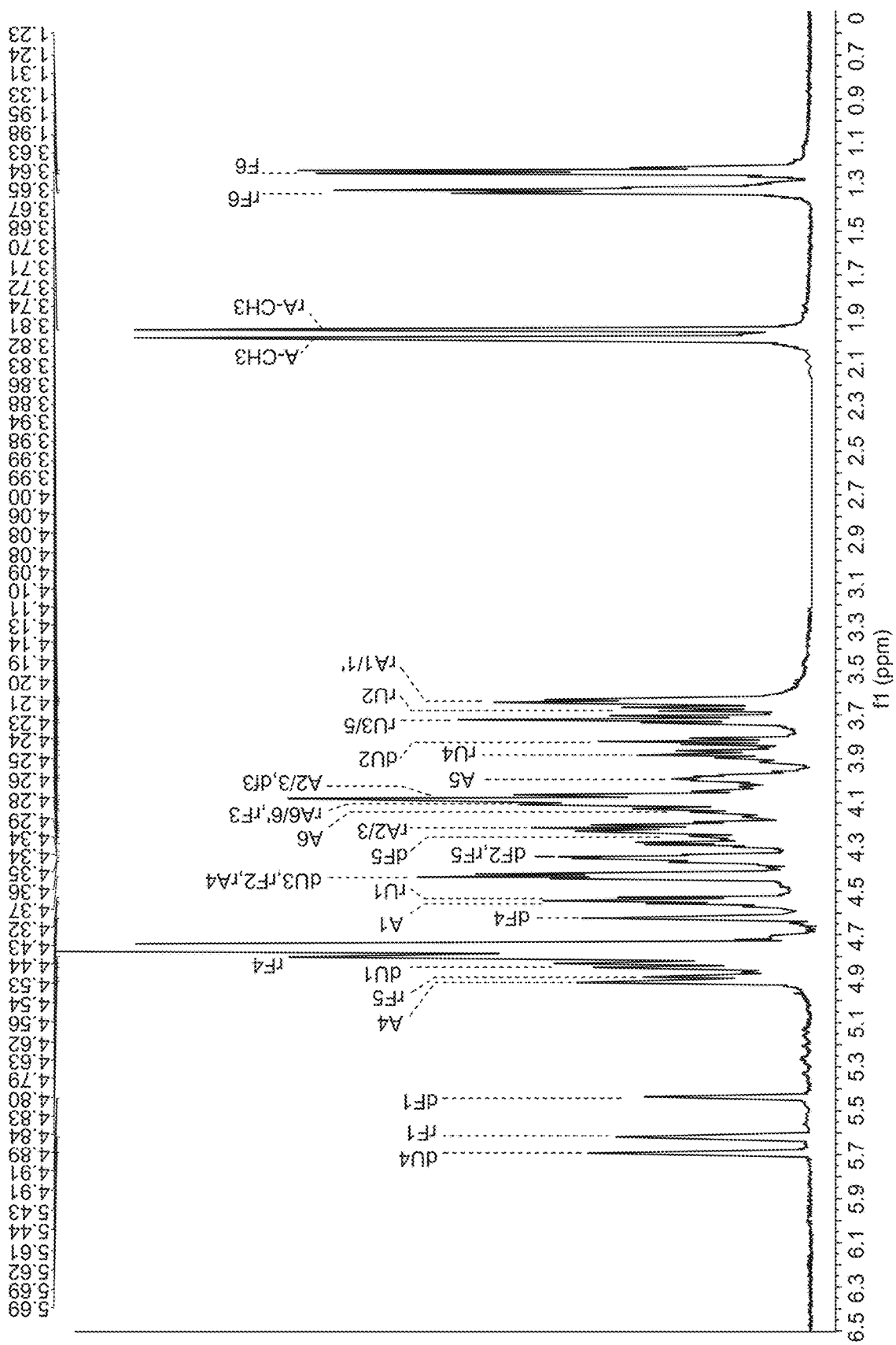
FIG. 2. $^1$H NMR spectrum and assignments for Compound A1
Figure 3:
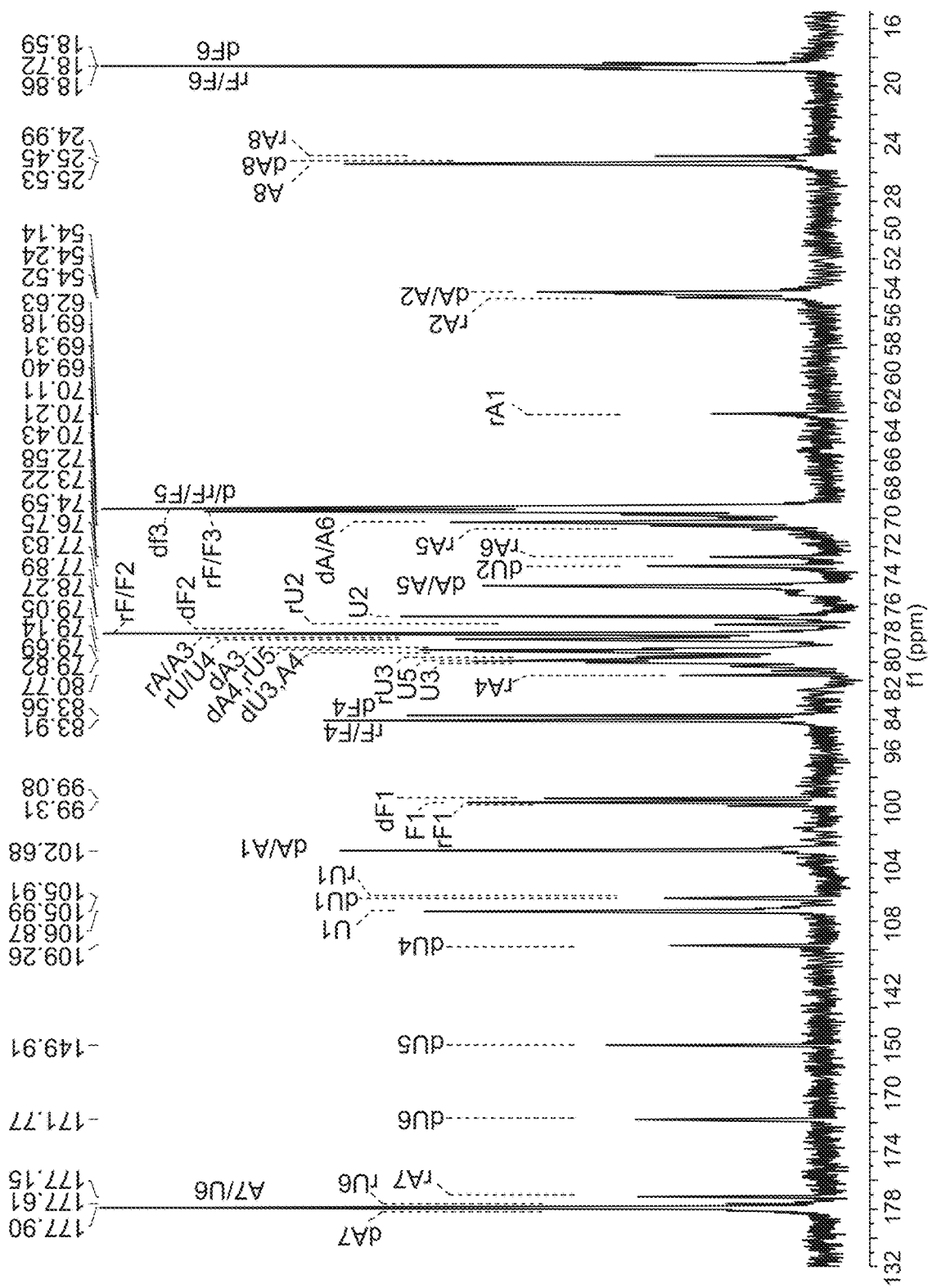
FIG. 3. $^{13}$C NMR spectrum and assignments for Compound A2
Figure 4:
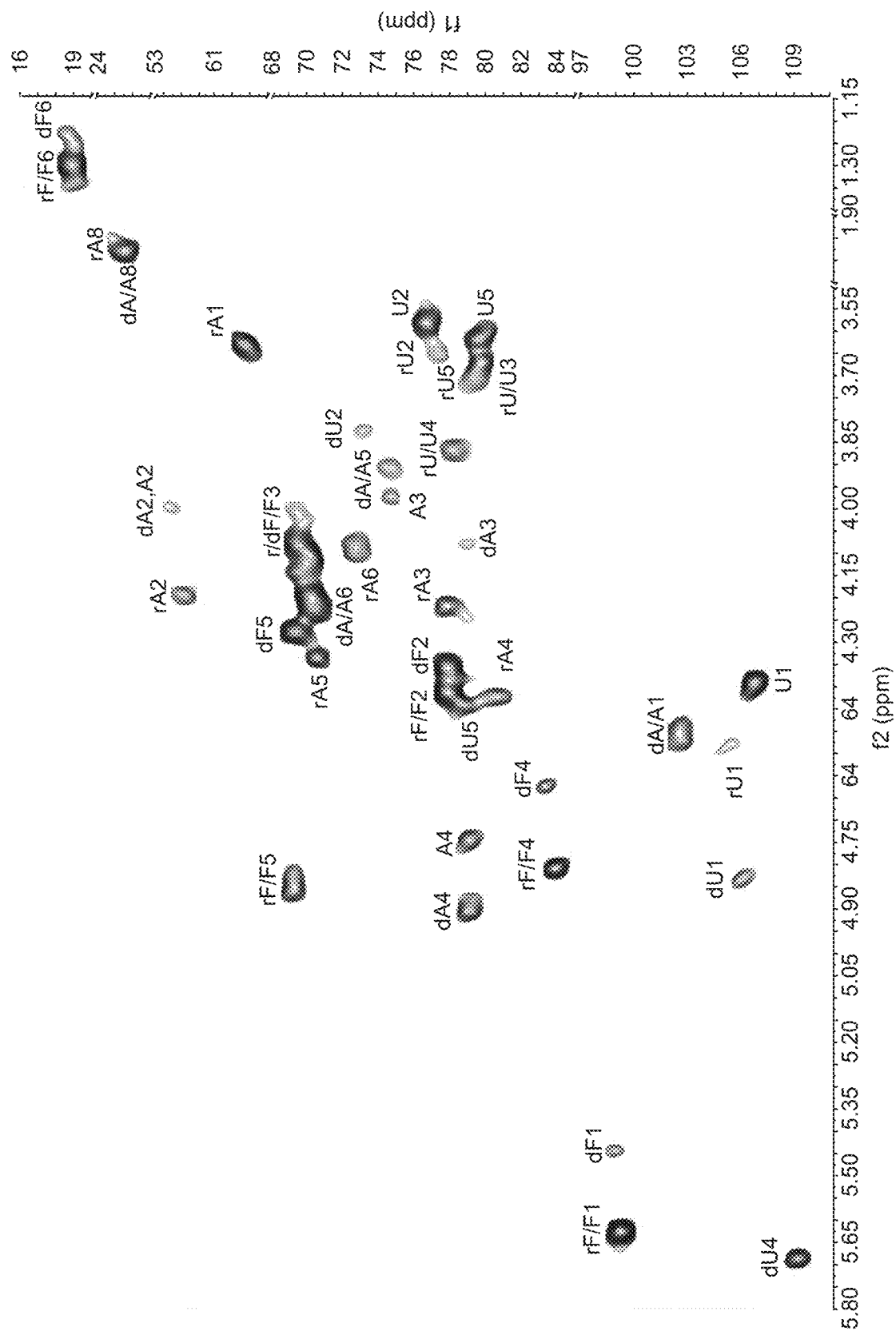
FIG. 4. $^{13}$C-$^1$H HSQC spectrum and assignments for Compound A3
Figure 5:
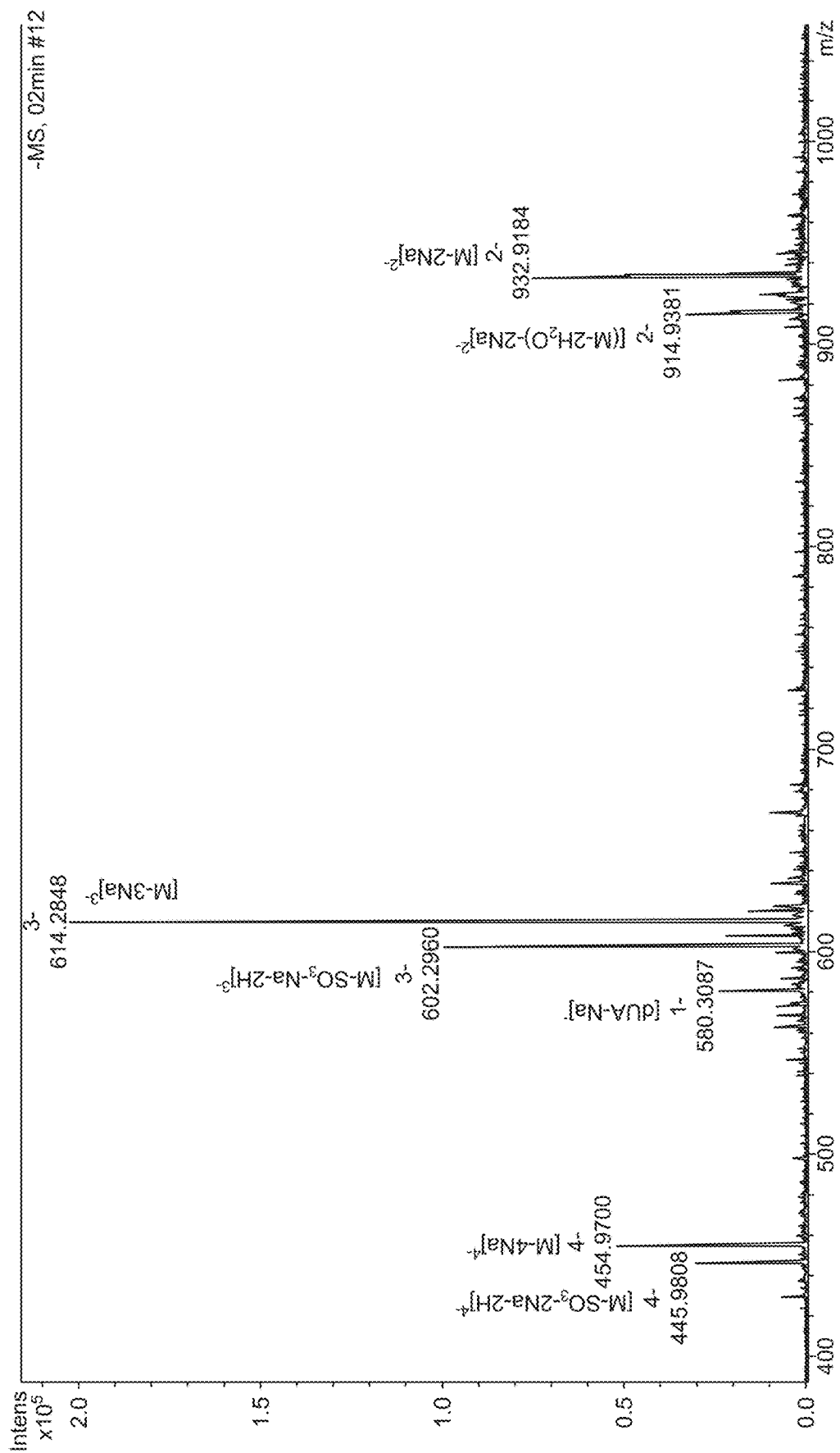
FIG. 5. Q-TOF MS spectrum and assignments for Compound A1

(2) Structural analysis of Compounds A1~A5: The $^1$H NMR spectrum and assignments for oligosaccharide compound A1 are shown in FIG. 2; the $^{13}$C NMR spectrum and assignments for Compound A2 are shown in FIG. 3; the $^{13}$C-$^1$H HSQC spectrum and assignments for Compound A3 are shown in FIG. 4; the Q-TOF MS spectrum and assignments for Compound A1 are shown in FIG. 5; the $^1$H/$^{13}$C NMR signal assignments for Compounds A1~A2 are shown in Tables 1 and 2, respectively.

According to $^1$H-/$^{13}$C-, 2D-NMR and Q-TOF MS analysis, the chemical structure of Compounds A1~A5 is L-Fuc$_{2S4S}$-(α1,3)-ΔUA-(α1,3)-{D-GaNAc$_{4S6S}$-(β1,4)-[L-Fuc$_{2S4S}$-(α1,3)]-D-GlcA-(β1,3)}$_{n+1}$-D-GalNAc$_{4S6S}$-ol, wherein n=1, 2, 3, 4 and 5, that is, Compounds A1~A5 are hexasaccharide, nonasaccharide, dodecasaccharide, pentadecasaccharide and octadecasaccharide, respectively, having the chemical structural formula of:

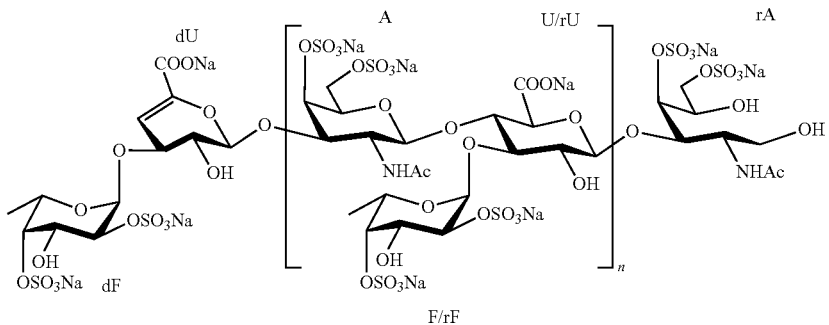

In A1, n=1, in A2, n=2; in A3, n=3; in A4, n=4; in A5, n=5.

TABLE 1

$^1$H/$^{13}$C NMR signal assignments and coupling constant of Compound A1 (ppm, Hz)

| | rA | U | F | A | dU | dF |
|---|---|---|---|---|---|---|
| H-1 | 3.636 | 4.536 | 5.615 | 4.550 | 4.838 | 5.432 |
| | $J_{1,2}$ = 6.72 | $J_{1,2}$ = 8.22 | $J_{1,2}$ = 3.72 | $J_{1,2}$ = 8.28 | $J_{1,2}$ = 7.98 | $J_{1,2}$ = 3.60 |
| H-2 | 4.199 | 3.666 | 4.426 | 4.079 | 3.820 | 4.355 |
| | $J_{2,3}$ = 7.80 | $J_{2,3}$ = 8.61 | $J_{2,3}$ = 9.72 | $J_{2,3}$ = 9.60 | $J_{2,3}$ = 8.34 | $J_{2,3}$ = 10.44 |
| H-3 | 4.220 | 3.721 | 4.095 | 4.088 | 4.438 | 4.055 |
| | — | $J_{3,4}$ = 8.94 | $J_{3,4}$ = 4.02 | — | $J_{3,4}$ = 2.46 | $J_{3,4}$ = 2.64 |
| H-4 | 4.328 | 3.879 | 4.795 | 4.912 | 5.688 | 4.623 |
| | — | $J_{4,5}$ = 9.18 | — | — | / | — |
| H-5 | 4.343 | 3.713 | 4.892 | 3.989 | | 4.282 |
| | — | | $J_{5,6}$ = 6.36 | $J_{5,6,6'}$ = 7.08, 4.62 | | $J_{5,6}$ = 6.78 |
| H-6 | 4.090 | | 1.320 | 4.245/4.145 | | 1.231 |
| | — | | | $J_{6,6'}$ = 11.10 | | |
| Ac—CH$_3$ | 1.947 | | | 1.985 | | |
| C-1 | 62.64 | 106.03 | 99.70 | 102.73 | 106.31 | 99.19 |
| C-2 | 54.57 | 77.29 | 77.96 | 54.34 | 73.28 | 77.90 |
| C-3 | 78.08 | 80.35 | 69.47 | 79.10 | 79.33 | 69.37 |
| C-4 | 80.80 | 78.34 | 84.08 | 79.22 | 109.30 | 83.63 |
| C-5 | 70.48 | 79.22 | 69.23 | 74.80 | 149.97 | 69.25 |
| C-6 | 72.63 | 177.63 | 18.78 | 70.42 | 171.83 | 18.59 |
| (Ac) C=O | 177.19 | | | 177.97 | | |
| (Ac) CH$_3$ | 25.02 | | | 25.46 | | |

Note:
rA represents D-GalNAc-ol at the reducing terminal; dU and dF represent ΔUA and L-Fuc linked to ΔUA.

TABLE 2

| $^1H/^{13}C$ NMR signals assignments for Compound A2 (ppm, Hz) | | | | | | | | | |
|---|---|---|---|---|---|---|---|---|---|
| | rA | rU | rF | A | U | F | dA | dU | dF |
| H-1 | 3.626 | 4.520 | 5.615 | 4.512 | 4.395 | 5.628 | 4.530 | 4.832 | 5.435 |
| H-2 | 4.189 | 3.661 | 4.412 | 4.010 | 3.579 | 4.412 | 4.047 | 3.830 | 4.348 |
| H-3 | 4.211 | 3.737 | 4.093 | 3.956 | 3.688 | 4.093 | 4.073 | 4.446 | 4.060 |
| H-4 | 4.403 | 3.958 | 4.803 | 4.711 | 3.880 | 4.803 | 4.908 | 5.686 | 4.623 |
| H-5 | 4.327 | 3.706 | 4.863 | 3.919 | 3.600 | 4.863 | 3.971 | | 4.288 |
| H-6 | 4.079 | | 1.299 | 4.206/4.123 | | 1.311 | 4.230/4.122 | | 1.231 |
| Ac—CH$_3$ | 1.947 | | | 1.980 | | 1.988 | | | |
| C-1 | 62.62 | 105.92 | 99.58 | 102.71 | 106.92 | 99.38 | 102.68 | 106.02 | 99.10 |
| C-2 | 54.53 | 77.23 | 77.89 | 54.19 | 76.76 | 77.90 | 54.20 | 73.22 | 77.84 |
| C-3 | 78.06 | 80.15 | 69.41 | 78.14 | 79.93 | 69.41 | 78.88 | 79.23 | 69.32 |
| C-4 | 80.76 | 78.33 | 83.96 | 79.18 | 78.33 | 83.96 | 79.09 | 109.26 | 83.54 |
| C-5 | 70.43 | 79.10 | 69.24 | 74.69 | 79.69 | 69.20 | 74.65 | 149.95 | 69.20 |
| C-6 | 72.59 | 177.62 | 18.86 | 70.27 | 177.88 | 18.86 | 70.21 | 171.78 | 18.59 |
| (Ac) C=O | 177.15 | | | 177.88 | | | 177.94 | | |
| (Ac) CH$_3$ | 24.99 | | | 25.52 | | | 25.45 | | |

Note:
in the table, rA, rU and rF represent GalNAc-ol at the reducing terminal, D-GlcA and L-Fuc glycosyl near the reducing terminal, respectively; dU, dA and dF represent AUA, D-GalNAc linked to AUA, and L-Fuc linked to AUA, respectively.

Example 2

Preparation of Compounds B1, B2, B3, B4 and B5

L-3,4-disulfated fucosyl-($\alpha$1,3)-L-4-deoxy-threo-hex-4-enepyranuronyl-($\alpha$1,3)-{D-N-acetyl-2-deoxy-2-amino-4,6-disulfated galactosyl-($\beta$1,4)-[L-3,4-disulfated fucosyl-($\alpha$1,3)-]D-glucuronyl-($\beta$1,3)}$_n$-D-N-acetyl-2-deoxy-2-amino-4,6-disulfated galactose-[L-3,4-disulfated fucosyl-($\alpha$1,3)-]-L-gulonic acid (n=0, 1, 2, 3 and 4, pentasaccharide, octasaccharide, hendecasaccharide, tetradecasaccharide, and heptadecasaccharide)

2.1 Materials

HsFG, Natural FG (sodium salt) from *Holothuria fuscopunctata*; which was prepared according to the literature method (Zhao L Y et al., *PNAS*, 2015, 112: 8284-8289), with a purity of 98% (HPGPC method), and a weight average molecular weight (Mw) of about 50 kDa.

The used reagents such as benzethonium chloride, benzyl chloride, DMF, sodium hydroxide, sodium chloride, and ethanol were all commercially available analytical reagents.

Sephadex G10/G25, medium (50-100 µm), GE Healthcare; Bio-Gel P-2 gel, fine (45-90 µm), Bio-Rad; Bio-Gel P-10 gel, medium (90-180 µm), Bio-Rad; 1200/1260 Series HPLC Chromatograph, Agilent.

2.2 Methods (1) Quaternary ammonium salt conversion of HsFG: 3.5 g of HsFG was treated according to the method described in 1.2 (1) of Example 1, obtaining 10.3 g of HsFG quaternary ammonium salt.

(2) Carboxyl esterification of HsFG: HsFG quaternary ammonium salt was treated according to the method described in 1.2 (2) of Example 1 to obtain HsFG carboxylate, and the sample was taken for $^1$H NMR detection, and the degree of carboxyl esterification of the obtained product was calculated to be about 44%;

(3) $\beta$-elimination depolymerization and terminal peeling reaction of HsFG: To the reaction solution obtained in the step (2), a freshly prepared 16.7 mL of 0.08 M sodium ethoxide-ethanol solution was added, and stirred at room temperature for 30 min, and then 2.5 mL of 2 M NaOH solution was added, and stirred at 60° C. for 30 min.

(4) Sodium salt conversion, carboxylic ester hydrolysis and terminal reduction of depolymerized product: To the reaction solution in the step (3) was added sequentially 67 mL of saturated NaCl solution, 536 mL of absolute ethanol, centrifuged at 4000 rpm for 10 min; the obtained precipitate was dissolved in 120 mL of water, added with 1.0 mL of 6 M NaOH solution, and stirred at room temperature for 30 min; NaBH$_4$ was added to a final concentration of about 0.1 M, and stirred at room temperature for 30 min, then 6 M HCl was added dropwise to neutralize the reaction solution (pH~7.0). The reaction solution was filtered through a 0.45 µm filter, and the filtrate was ultrafiltered through a 30 kDa ultrafiltration membrane; the ultrafiltrate was concentrated and desalted by G25 gel column chromatography and lyophilized to obtain 1.53 g of depolymerized product dHsFG (yield 43.7%).

(5) Isolation and purification of Compounds B1~B5: Ig of dHsFG in the step (4) was dissolved in 10 mL of 0.2 M NaCl, loaded on a Bio-Gel P-10 gel column (Ø2 cm, 1 200 cm), eluted with 0.2 M NaCl solution at a flow rate 15 mL/h, and the eluate fractions of 2.5 mL/tube were collected. UV spectrophotometry ($\lambda$max 234 nm) was used for monitoring. HPGPC (TSK G2000 SW column) was used to detect the sample purity and composition of the eluate fractions. The unpurified fractions were continued to be purified on a Bio-Gel P-10 gel column until the HPGPC spectrum of the product exhibited a single elution peak. The purified fractions were desalted on a Sephadex G-10 or Bio-Gel P-2 column and then lyophilized.

(6) Spectral analysis: the same as the method described in 1.2 (6) of Example 1, $^1$H-/$^{13}$C- and 2D-NMR was detected using Bruker DRX 800 MHz NMR spectrometer, ESI-Q-TOF MS was analyzed using microTOF-QII ESI-MS (Bruker, Germany) mass spectrometer. The detected data were analyzed using Bruker Compass Data-Analysis 4.0 (Bruker-Daltonics, Germany) software.

2.3 Results (1) Compound B1 54 mg, B2 177 mg, B3 154 mg, B4 86 mg, B5 57 mg were obtained by the method described above, and the purity was determined to be >99% by HPGPC method.

Figure 6:
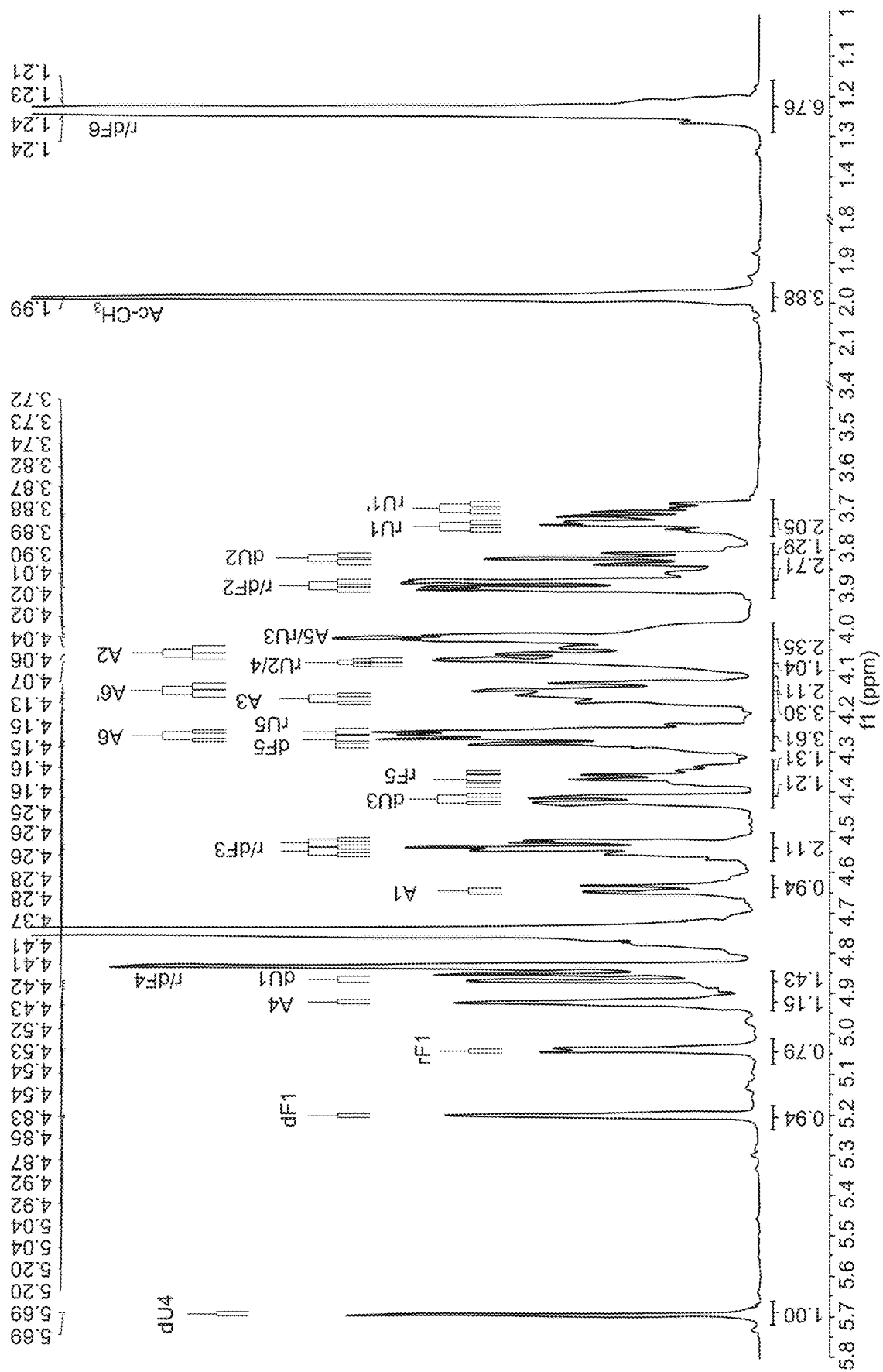
FIG. 6. $^1$H NMR spectrum and assignments for Compound B1
Figure 7:
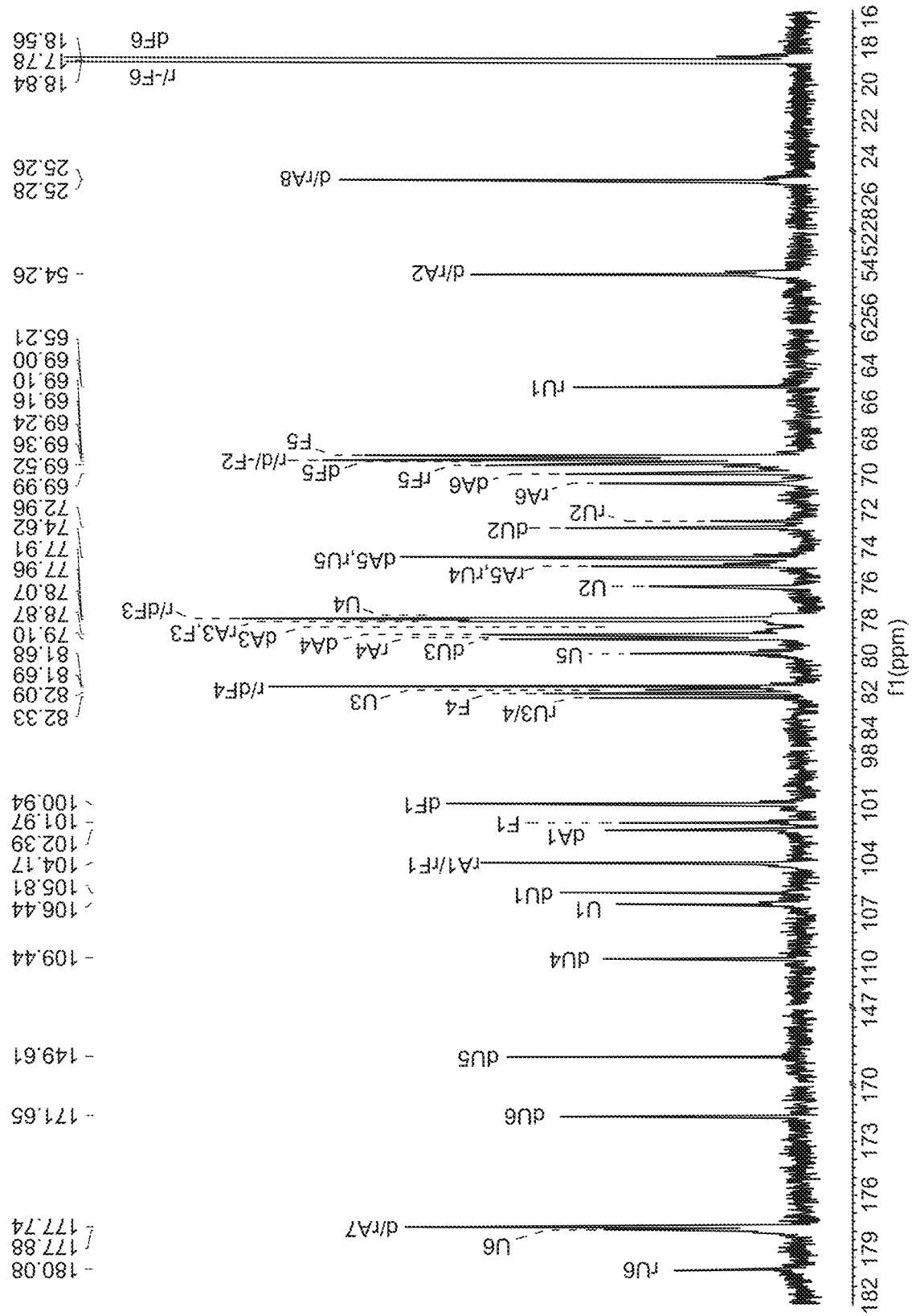
FIG. 7. $^{13}$C NMR spectrum and assignment for Compound B2
Figure 8:
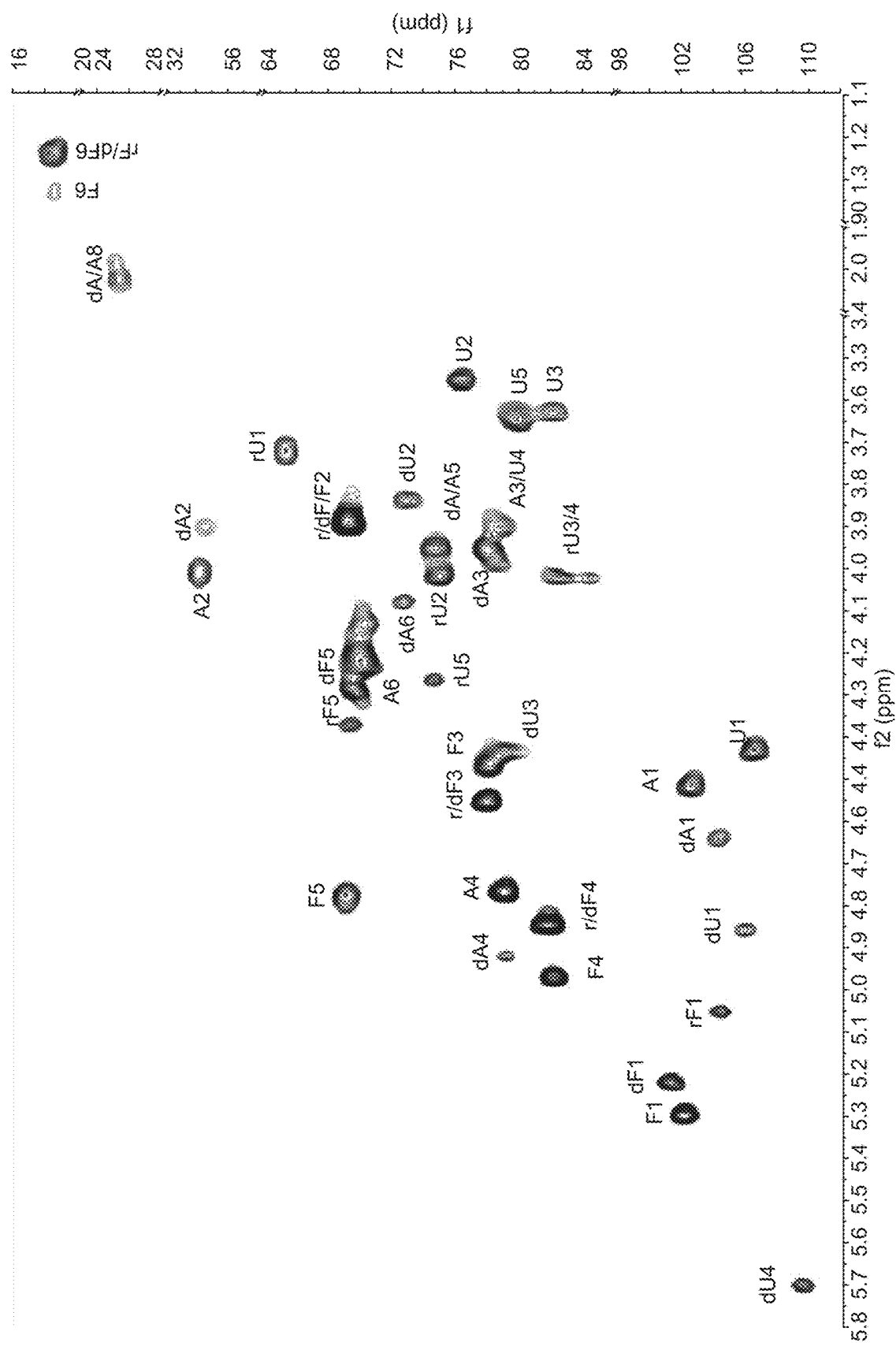
FIG. 8. $^{13}$C-$^1$H HSQC spectrum and assignments for Compound B3
Figure 9:
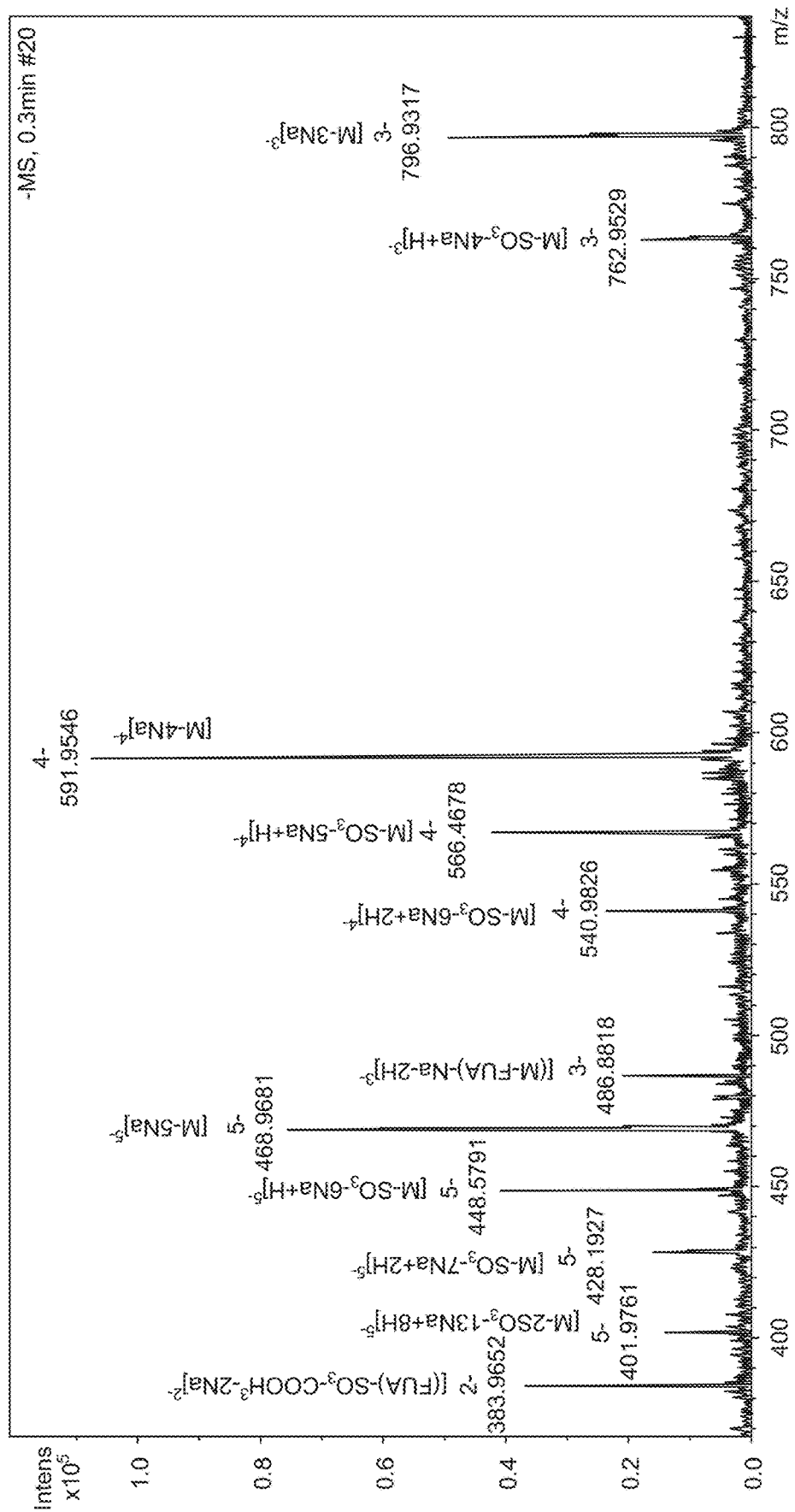
FIG. 9. Q-TOF MS spectrum and assignments for Compound B2

(2) Structure analysis of Compounds B1~B5: The $^1$H NMR spectrum of oligosaccharide Compound B1 is shown in FIG. 6; the $^{13}$C NMR spectrum and assignments for Compound B2 are shown in FIG. 7; the $^{13}C$-$^{1}H$ HSQC spectrum and assignments of Compound B3 are shown in FIG. 8; the Q-TOF MS spectrum and assignments for Compound B2 are shown in FIG. 9; the $^{1}H$/$^{13}C$ NMR signal assignments for Compounds B1~B2 are shown in Tables 3 and 4, respectively.

Combined with $^{1}H$-/$^{13}C$-/2D-NMR and Q-TOF MS analysis, the chemical structure of Compounds B1~B5 is L-Fuc$_{3S4S}$-($\alpha$1,3)-L-$\Delta$UA-($\alpha$1,3)-{D-GalNAc$_{4S6S}$-($\beta$1,4)-[L-Fuc$_{3S4S}$-($\alpha$1,3)]-D-GlcA-($\beta$1,3)}$_n$-D-GalNAc$_{4S6S}$-($\beta$1,4)-[L-Fuc$_{3S4S}$-($\alpha$1,3)]-D-GlcA-ol (wherein n=0, 1, 2, 3 and 4). That is, Compounds B1~B5 are pentasaccharide, octasaccharide, hendecasaccharide, tetradecasaccharide, and heptadecasaccharide, respectively, having the chemical structural formula of:

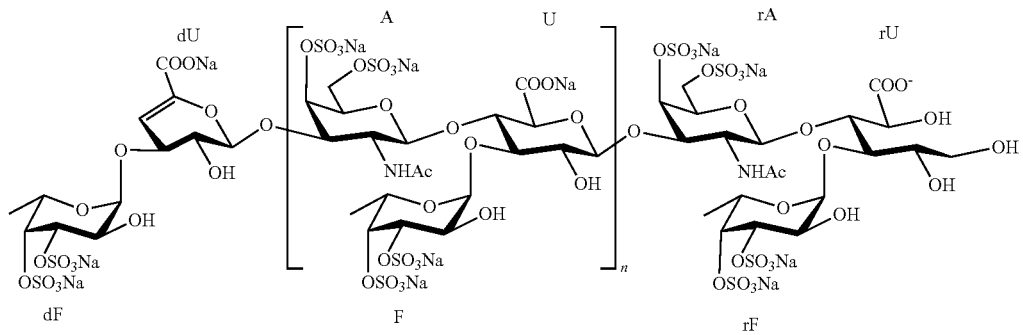

In B1, n=0; in B2, n=1; in B3, n=2; in B4, n=3; in B5, n=4.

TABLE 3

$^{1}H$/$^{13}C$ NMR signal assignments and coupling constants for Compound B1 (ppm, Hz)

| | rU | rF | rA | dU | dF |
|---|---|---|---|---|---|
| H-1 | 3.743/3.700 | 5.039 | 4.639 | 4.859 | 5.201 |
| | $J_{1,1'}$ = 11.82 | $J_{1,2}$ = 3.96 | $J_{1,2}$ = 8.52 | $J_{1,2}$ = 8.64 | $J_{1,2}$ = 3.78 |
| H-2 | 4.060 | 3.886 | 4.043 | 3.822 | 3.886 |
| | $J_{1/1',2}$ = 3.96/6.78 | $J_{2,3}$ = 10.38 | $J_{2,3}$ = 8.70 | $J_{2,3}$ = 7.56 | $J_{2,3}$ = 10.38 |
| H-3 | 4.019 | 4.546 | 4.167 | 4.418 | 4.529 |
| | — | $J_{3,4}$ = 2.76 | $J_{3,4}$ = 2.16 | $J_{3,4}$ = 2.40 | $J_{3,4}$ = 2.82 |
| H-4 | 4.071 | 4.831 | 4.918 | 5.693 | 4.831 |
| | $J_{4,5}$ = 7.44 | — | — | | — |
| H-5 | 4.256 | 4.363 | 4.019 | | 4.273 |
| | | $J_{5,6}$ = 6.84 | $J_{5,6/6'}$ = 8.24, 3.52 | | $J_{5,6}$ = 6.48 |
| H-6 | | 1.240 | 4.268/4.146 | | 1.231 |
| | | | $J_{6,6'}$ = 10.68 | | |
| (Ac)—CH$_3$ | | | 1.986 | | |
| C-1 | 65.28 | 104.26 | 104.31 | 105.82 | 101.04/175.8 |
| C-2 | 72.59 | 69.39 | 54.35 | 72.90 | 69.27 |
| C-3 | 82.44 | 77.93 | 78.56 | 79.12 | 77.96 |
| C-4 | 75.17 | 81.70 | 78.94 | 109.52 | 81.72 |
| C-5 | 75.17 | 69.55 | 74.64 | 149.51 | 69.02 |
| C-6 | 180.08 | 18.85 | 70.64 | 171.65 | 18.56 |
| (Ac)—C=O | | | 177.65 | | |
| (Ac)—CH$_3$ | | | 25.19 | | |

Note:
in the table, rU and dU represent D-GlcA-ol at the reducing terminal and $\Delta$UA at the non-reducing terminal, respectively; rF and dF represent L-Fuc glycosyl groups linked to the reducing terminal D-GlcA-ol and $\Delta$UA, respectively. A represents D-GalNAc.

TABLE 4

$^{1}H$-/$^{13}C$-NMR signal assignments for Compound B2 (ppm, Hz)

| | rU | rF | rA | U | F | A | dU | dF |
|---|---|---|---|---|---|---|---|---|
| H-1 | 3.733/3.691 | 5.033 | 4.622 | 4.426 | 5.286 | 4.530 | 4.846 | 5.204 |
| H-2 | 4.066 | 3.886 | 3.976 | 3.546 | 3.871 | 4.090 | 3.830 | 3.886 |
| H-3 | 4.012 | 4.545 | 3.981 | 3.632 | 4.458 | 4.087 | 4.426 | 4.530 |
| H-4 | 4.012 | 4.837 | 4.755 | 3.954 | 4.973 | 4.912 | 5.686 | 4.831 |

TABLE 4-continued

| $^1$H-/$^{13}$C-NMR signal assignments for Compound B2 (ppm, Hz) | | | | | | | | |
|---|---|---|---|---|---|---|---|---|
|  | rU | rF | rA | U | F | A | dU | dF |
| H-5 | 4.248 | 4.370 | 4.022 | 3.641 | 4.799 | 4.019 |  | 4.275 |
| H-6 |  | 1.241 | 4.211/4.129 |  | 1.343 | 4.321/4.222 |  | 1.231 |
| Ac—CH$_3$ |  |  | 1.992 |  |  | 1.997 |  |  |
| C-1 | 65.21 | 104.17 | 104.17 | 106.4 | 101.97 | 102.39 | 105.8 | 100.9 |
| C-2 | 72.59 | 69.24 | 54.26 | 76.24 | 69.16 | 54.26 | 72.96 | 69.10 |
| C-3 | 82.33 | 77.91 | 78.07 | 81.88 | 78.07 | 78.55 | 79.10 | 77.96 |
| C-4 | 75.03 | 81.68 | 78.87 | 77.91 | 82.09 | 78.98 | 109.4 | 81.69 |
| C-5 | 74.62 | 69.52 | 75.03 | 79.86 | 69.00 | 74.62 | 149.6 | 69.36 |
| C-6 | 180.08 | 18.84 | 70.52 | 177.88 | 18.78 | 69.99 | 171.6 | 18.56 |
| (Ac) —C═O |  |  | 177.74 |  |  | 177.74 |  |  |
| (Ac) —CH$_3$ |  |  | 25.28 |  |  | 25.26 |  |  |

Note:
in the table, rA represent GalNAc near the reducing terminal, and rU and dU represent D-GlcA-ol at the reducing terminal and AUA at the non-reducing terminal, respectively; rF and dF represent L-Fuc glycosyl linked to D-GlcA-ol at the reducing terminal and AUA, respectively.

Example 3

Preparation of Compounds B6, B7, B8

L-3,4-disulfated fucosyl-(α1,3)-L-4-deoxy-threo-hex-4-enopyanosyluronyl-(α1,3)-{D-N-acetyl-2-deoxy-2-amino-4,6-disulfated galactosyl-(β1,4)-[L-3,4-disulfated fucosyl-(α1,3)-]D-glucuronyl-(β1,3)}$_n$-D-N-acetyl-2-deoxy-2-amino-4,6-disulfated galactosyl-(β1,4)-[L-3,4-disulfated fucosyl-(α1,3)-]-D-glucuronic acid (n═0, 1 and 2)

3.1 Materials:

HsFG, FG sodium salt derived from *Holothuria fuscopunctata*, derived from the same as described in 2.1 of Example 2.

The reagents used such as benzethonium chloride, benzyl chloride, DMF, sodium hydroxide, sodium chloride and ethanol were all commercially available analytical reagents.

3.2 Methods:

(1) Quaternary ammonium salt conversion of HsFG: 9.55 g of HsFG quaternary ammonium salt was prepared from 3.5 g of HsFG by the method as described in 2.2(1) of Example 2.

(2) Carboxyl esterification of HsFG: carboxyl esterified HsFG was obtained by the method described in 2.2 (2) of Example 2, and the degree of carboxyl esterification was determined to be about 44% by $^1$H NMR;

(3) β-elimination depolymerization of HsFG: To the reaction solution obtained in the step (2), a freshly prepared 16.0 mL of 0.08 M sodium ethoxide-ethanol solution was added, and stirred at room temperature for 30 min.

(4) Sodium salt conversion and carboxylic ester hydrolysis of the depolymerized product: 67 mL of saturated sodium chloride solution and 536 mL of absolute ethanol were added to the reaction solution obtained in the step (3), centrifuged at 4000 rpm×10 min; the obtained precipitate was dissolved in water (125 mL), 1.05 mL of 6 M NaOH solution was added, stirred at room temperature for 30 min, and then neutralized by dropwise addition of 6 M HCl (pH~7.0). The reaction solution was filtered through a 0.45 μm filter, and the filtrate was ultrafiltered through a 30 kDa ultrafiltration membrane package. The ultrafiltrate was desalted by G25 gel column chromatography and lyophilized to obtain 1.623 g of depolymerized product dHsFG' (yield 46.4%).

(5) Isolation and purification of Compounds B6~B8: 1 g of depolymerized product dHsFG' was dissolved in 10 mL of 0.2 M NaCl, loaded on a Bio-Gel P-10 gel column (Ø2 cm, 1 200 cm), and eluted with 0.2 M NaCl solution at a flow rate of 15 mL/h. The eluate fractions of 2.5 mL/tube were collected. Ultraviolet spectrophotometry (λmax 234 nm) was used for monitoring and the same eluate fractions were combined. HPGPC (TSK G2000 SW column) was used to detect the purity and composition of chromatographic samples. The unpurified samples were further purified by Bio-Gel P-10 column chromatography. The purified oligosaccharides were desalted on a Sephadex G-10 or Bio-Gel P-2 gel column and then lyophilized.

(6) Spectral analysis: By the same method described in 1.2 (6) of Example 1, $^1$H-/$^{13}$C- and 2D-NMR were detected using Bruker DRX 800 MHz NMR spectrometer, Q-TOF MS was analyzed using microTOF-QII ESI-MS (Bruker, Germany) mass spectrometer. The detected data were analyzed using Bruker Compass Data-Analysis 4.0 (Bruker-Daltonics, Germany) software.

3.3 Results (1) 47 mg of Compound B6, 55 mg of B7, 35 mg of B8 were obtained according to the treatment procedure described in 3.2. The purity was detected to be >99% by HPGPC method (area normalization method).

Figure 10:
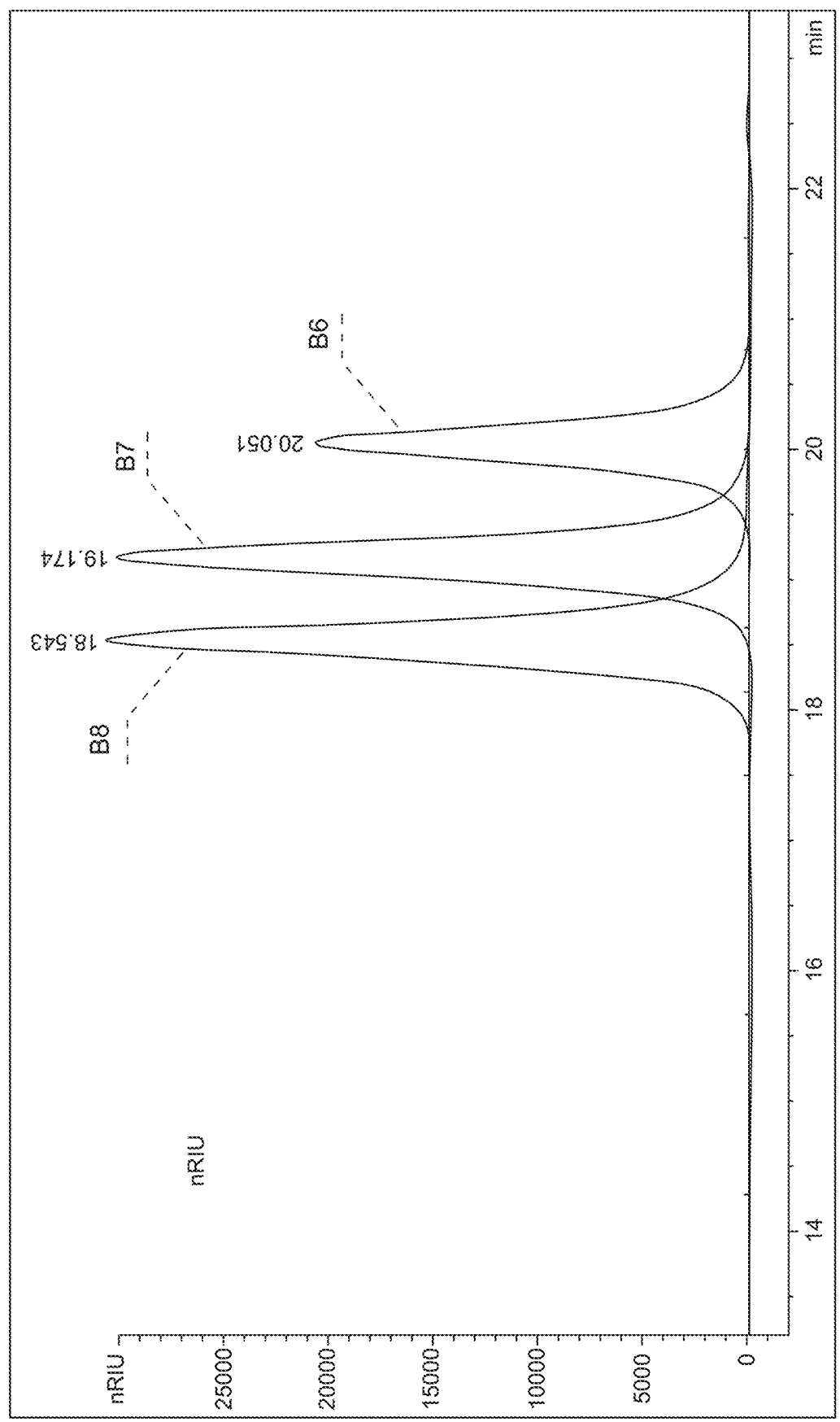
FIG. 10. HPGPC profiles of Compound B6-B8

(2) Structural analysis of Compounds B6~B8: The HPGPC profiles of Compounds B6~B8 are shown in FIG. 10. Combined with $^1$H-/$^{13}$C-/2D-NMR and Q-TOF MS analysis, Compounds B6, B7 and B8 are L-Fuc$_{3S4S}$-(α1,3)-L-ΔUA-(α1,3)-{D-GaNAc$_{4S6S}$-(β1,4)-[L-Fuc$_{3S4S}$-(α1,3)]-D-GlcA-(β1,4)}$_n$-D-GalNAc$_{4S6S}$-(β1,4)-[L-Fuc$_{3S4S}$-(α1,3)]-D-GlcA (wherein n═0, 1 and 2, namely pentasaccharide, octasaccharide and hendecasaccharide), having the chemical structural formula of:

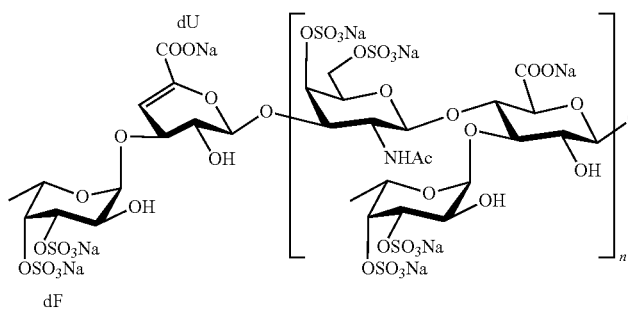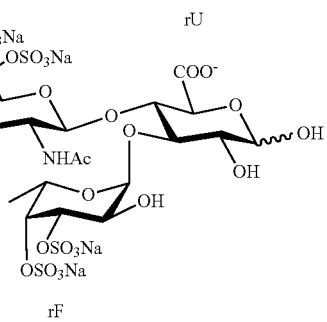

In B6, n=0; in B7, n=1; in B8, n=2.

Example 4

Preparation of Compounds A6, A7 and A8

L-Fuc$_{2S4S}$-($\alpha$1,3)-[6-Me-$\Delta$UA-($\alpha$1,3)]-{D-Gal-NAc$_{4S6S}$-($\beta$1,4)-[L-Fuc$_{2S4S}$-($\alpha$1,3)-]-D-6-Me-GlcA-($\beta$1,4)}2-D-GalNAc$_{4S6S}$-ol, and L-Fuc$_{2S4S}$-($\alpha$1,3)-L-$\Delta$UA-($\alpha$1,3)-{D-GaNS$_{4S6S}$-($\beta$1,4)-[L-Fuc$_{2S4S}$-($\alpha$1,3)-]-D-GlcA-($\beta$1,3)}2-D-GalNS$_{4S6S}$-ol and L-Fuc$_{2S4S}$-($\alpha$1,3)-[6-Me-$\Delta$UA-($\alpha$1,3)]-{D-GalNAc$_{4S6S}$-($\beta$1,4)-[L-Fuc$_{2S4S}$-($\alpha$1,3)-]-D-6-Methyl-GlcA-($\beta$1,3)}$_2$-D-1-Me-GalNAc$_{4S6S}$-ol

4.1 Materials

Compound A2, its preparation method and chemical structure were the same as described in Example 1.

Hydrazine sulfate, hydrazine hydrate, Et$_3$N·SO$_3$ ([Et$_3$N—SO$_3$H]Cl, N,N-diethyl-N-sulfoethanammonium chloride) were all commercially available analytical reagents.

4.2 Methods and Results (1) Preparation of Compound A6: 10 mg of Compound A2 was dissolved in 0.5 mL of water, converted into H+ type by a Dowex 50X8 hydrogen-type cation exchange resin column, and the eluate was neutralized with tetrabutylammonium hydroxide and lyophilized to obtain 19 mg of A2 tetrabutylammonium salt. The obtained A2 tetrabutylammonium salt was dissolved in 1 mL of dimethyl sulfoxide (DMSO), 15 µL of 2 M trimethylsilyldiazomethane (TMSD) was added and reacted for 60 min at room temperature, 15 µL of acetic acid was added to remove the remaining TMSD, 4 mL of absolute ethanol was added at 4° C., and centrifuged at 4000 rpm×30 min, and the obtained precipitate was dissolved in 1 mL of water, and converted into sodium-type by a Dowex/r50w×8 50-100 (Na+ type) exchange resin. The obtained product was desalted on a Sephadex G-10 column and lyophilized to obtain 8.35 mg of A6. $^1$H—/$^{13}$C— and 2D-NMR were detected by the method described in 1.2 (6) of Example 1, and the structure of Compound A6 (the methyl ester group signal on $\Delta$UA was located at 3.70 ppm) was confirmed to be L-Fuc$_{2S4S}$-($\alpha$1,3)-[6-Methyl-$\Delta$UA-($\alpha$1,3)]-{D-Ga-NAc$_{4S6S}$-($\beta$1,4)-[L-Fuc$_{2S4S}$-($\alpha$1,3)-]-D-6-Methyl-GlcA-($\beta$1,4)}$_2$-D-GalNAc$_{4S6S}$-ol, having the structural formula of:

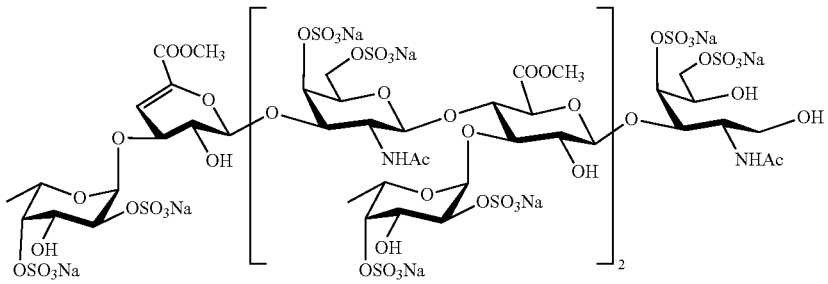

(2) Preparation of compound A7: 10 mg of Compound A2 was added with 2.5 mg of hydrazine sulfate and 0.25 mL of hydrazine hydrate, and stirred under nitrogen atmosphere at 105° C. for 15 h; 0.5 mL of 16% NaCl solution and 3 mL of absolute ethanol were added to the reaction solution, and centrifuged at 4000 rpm×20 min. The resulting precipitate was dissolved in 10 mL of water and dialyzed with a 500-1000 Da dialysis bag. The retentate was lyophilized to obtain 8 mg of deacetylated product. The NMR spectrum was detected by the method described in 1.2 (6) of Example 1, and the chemical structure of the deacetylated product (the Ac methyl signal at 2.0 ppm disappeared and the H signal at the 2-position of GalNH$_2$ appeared at 3.0 ppm) was confirmed to be:

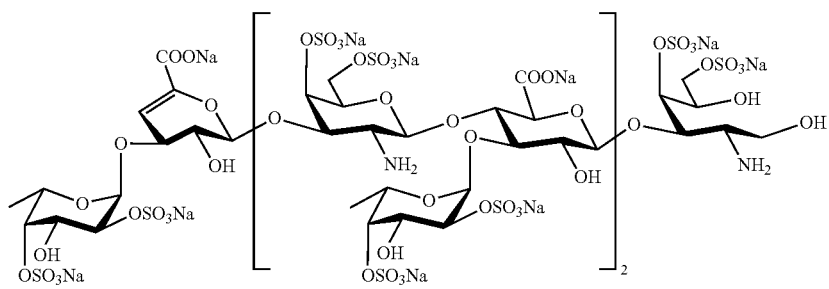

The A2 deacetylated product was dissolved in 1 mL of water, 36 mg of $Na_2CO_3$ was added and heated to 55° C., and 15 mg of $Et_3N \cdot SO_3$ was added at 0, 5 and 10 h after the start of the reaction, respectively. The reaction mixture was stirred at 55° C. for 15h. Then 1 mL of 16% NaCl solution and 8 mL of absolute ethanol were added to the reaction solution, and centrifuged at 4000 rpm×20 min; the precipitate was collected and dissolved in 10 mL of water, and then dialyzed with a 500-1000 Da dialysis bag. The dialysis retentate was lyophilized to obtain 6.8 mg of N-sulfated product A7.

$^1H$—/$^{13}C$— and 2D-NMR were detected according to method as described in 1.2(6) of Example 1, and the chemical structure of Compound A7 was confirmed to be L-$Fuc_{2S4S}$-($\alpha$1,3)-L-$\Delta$UA-($\alpha$1,3)-{D-$GalNS_{4S6S}$-($\beta$1,4)-[L-$Fuc_{2S4S}$-($\alpha$1,3)-]-D-GlcA-($\beta$1,3)}$_2$-D-Gal-$NS_{4S6S}$-ol. The structural formula is:

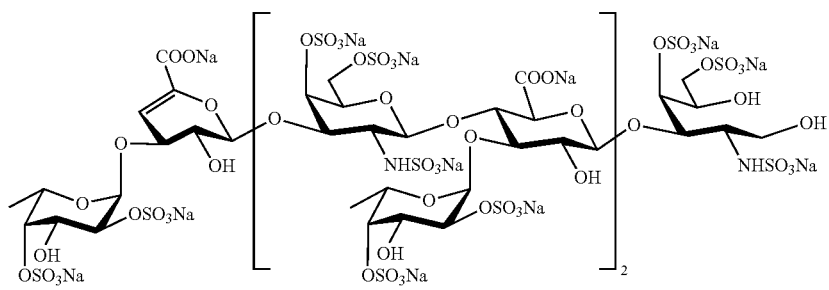

(3) Preparation of Compound A8: 20 mg of Compound A2 was added with Dowex 50X8 hydrogen type cation exchange resin as a catalyst, and then 5 mL of methanol solution was added, and heated to reflux under a nitrogen atmosphere overnight. The resin was removed by filtration, and the filtrate was evaporated to remove the solvent to obtain C1-hydroxyalkylated product of A2. The product was converted into H+ type by a Dowex 50X8 cation exchange resin column, and the eluate was neutralized with tetrabutylammonium hydroxide and lyophilized to obtain 37 mg of tetrabutylammonium salt of the C1 hydroxyalkylated product of A2. The obtained product was dissolved in 2 mL of DMSO, added with 30 μL of 2 M TMSD, and reacted for 60 min at room temperature. Then 30 μL of acetic acid was added to remove the remaining TMSD, and 2 mL of 16% NaCl solution and 8 mL of absolute ethanol were added at 4° C., centrifuged at rpm×30 min, the obtained precipitate was dissolved in 2 mL of water and converted into sodium type by a Dowex/r50w×8 50-100 (Na+ type) exchange resin column. The obtained product was desalted on a Sephadex G-10 column and lyophilized to obtain 13.5 mg of A8.

$^1H$—/$^{13}C$— and 2D-NMR were detected by the method as described in 1.2 (6) of Example 1, and the structure of compound A8 (the methyl signal of $\Delta$UA methyl ester was at 3.70 ppm, and the methyl signal at the reducing terminal was at 3.23 ppm) was confirmed to be L-$Fuc_{2S4S}$-($\alpha$1,3)-[6-Methyl-$\Delta$UA-($\alpha$1,3)]-{D-$GaNAc_{4S6S}$-($\beta$1,4)-[L-$Fuc_{2S4S}$-($\alpha$1,3)-]-D-6-Methyl-GlcA-($\beta$1,3)}$_2$-D-1-Methyl-Gal-$NAc_{4S6S}$-ol, having the structural formula of:

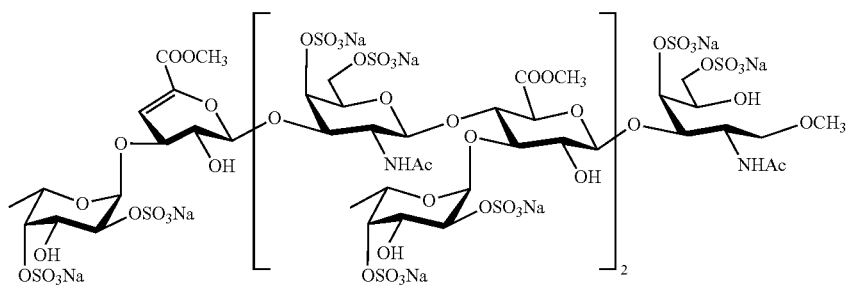

Similarly, according to the method of the present example, an alcohol corresponding to a C2-C6 linear or branched alkane or an alkene may be selected to prepare the corresponding hydroxyalkylated product A8'.

Example 5

Preparation of Compounds B9, B10 and B11

L-Fuc$_{2S4S}$-(α1,3)-L-ΔUA-(α1,3)-D-Gal-NAc$_{4S6S}$-(β1,4)-[L-Fuc$_{2S4S}$-(α1,3)]-D-GcA-(β1,3)-D-GaNAc$_{4S6S}$-(β1,4)-[L-Fuc$_{2S4S}$-(α1,3)]-D-β1-Bn-GlcA, L-Fuc$_{2S4S}$-(α1,3)-L-6-Me-ΔUA-(α1,3)-D-GaNAc$_{4S6S}$-(β1,4)-[L-Fuc$_{2S4S}$-(α1,3)]-D-6-Me-ΔUA-GlcA-(β1,3)-D-GaNAc$_{4S6S}$-(β1,4)-[L-Fuc$_{2S4S}$-(α1,3)]-D-β1-Bnz-6-Me-GlcA and L-Fuc$_{2S4S}$-(α1,3)-L-ΔUA-(α1,3)-{D-GaNAc$_{4S6S}$-(β1,4)-[L-Fuc$_{2S4S}$-(α1,3)]-D-GlcA-(β1,3)}$_2$-D-GalNAc$_{4S6S}$-(β1,4)-[L-Fuc$_{2S4S}$-(α1,3)]-D-1-deoxy-1-amino-GlcA-ol-N-4-benzoic ethyl ester 5.1 Materials Using SvFG as a starting material, hendecasaccharide (B3') was prepared according to the method described in Example 2, and octasaccharide (B7') was prepared according to the method described in Example 3.

Ethyl 4-aminobenzoate, tetrabutylammonium hydroxide, dichloromethane, pyridine, acetic anhydride, benzyl alcohol, boron trifluoride, ether, and so on were all commercially available analytical reagents.

5.2 Methods and results (1) Preparation of Compound B9: 40 mg of Compound B7' was dissolved in 4 mL of water, converted into H+ type by a Dowex 50X8 hydrogen type cation exchange resin column, and the eluate was neutralized with tetrabutylammonium hydroxide and lyophilized to obtain 80 mg of B7' tetrabutylammonium salt. The obtained B7' tetrabutylammonium salt was added with 8 mL of pyridine and 8 mL of acetic anhydride, stirred at 100° C. for 30 min, and blowing-dried with nitrogen at room temperature. The residue was dissolved in 4 mL of dichloromethane, added with 128 μL of benzyl alcohol, and then added dropwise with 20 μL of boron trifluoride etherate (BF$_3$OEt$_2$) at 0° C., and heated under reflux for 36 h. The reaction was terminated by adding water. After shaking and standing, the CH$_2$Cl$_2$ layer was taken and evaporated to dryness to remove CH$_2$Cl$_2$. The residue was added with 4 mL of 0.02 M sodium methoxide-methanol solution at room temperature, stirred for 10 min to remove acetyl; evaporated to dryness to remove methanol, converted into H+ type by a Dowex 50X8 hydrogen-type cation exchange resin column. The eluate was neutralized with sodium hydroxide, and isolated and purified by Bio-gel P6, and the sugar-containing samples were combined, concentrated and desalted on a Sephadex G-10 column and lyophilized to obtain 24 mg of Compound B9.

$^1$H—$^{13}$C— and 2D-NMR were detected by the same method as described in 1.2 (6) of Example 1, and the structure of Compound B9 (the benzyl-CH$_2$ signal was at 4.6 ppm and the benzene ring signal was at 7.3 ppm) was confirmed to be L-Fuc$_{2S4S}$-(α1,3)-L-ΔUA-(α1,3)-D-GaNAc$_{4S6S}$-(D1,4)-[L-Fuc$_{2S4S}$-(α1,3)]-D-GlcA-(β1,3)-D-GalNAc$_{4S6S}$-(β1,4)-[L-Fuc$_{2S4S}$-(α1,3)]-D-1-Benzyl-GlcA-ol, having the structural formula of:

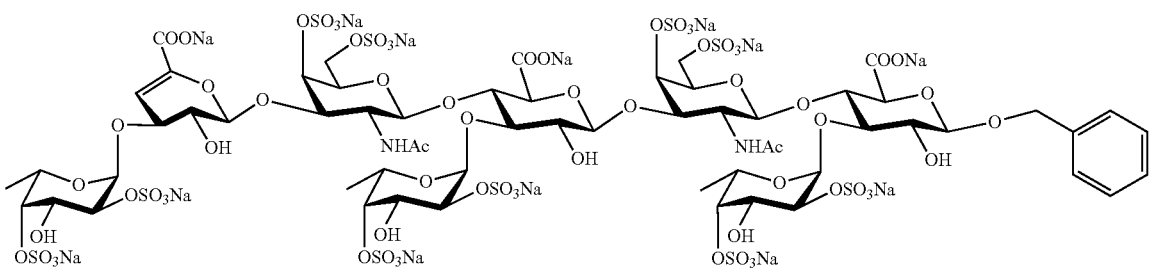

(2) Preparation of Compound B10: 10 mg of Compound B9 was dissolved in 0.5 mL of water, converted into H+ type by a Dowex 50X 8 hydrogen type cation exchange resin column, and the eluate was neutralized with tetrabutylammonium hydroxide and lyophilized to obtain 19 mg of B9 tetrabutylammonium salt. The obtained B9 tetrabutylammonium salt was dissolved in 1 mL of dimethyl sulfoxide (DMSO), added with 15 μL of 2 M trimethylsilyldiazomethane (TMSD), and reacted at room temperature for 60 min, then added with 15 μL of acetic acid to remove the remaining TMSD. 4 mL of absolute ethanol was added at 4° C., centrifuged at 4000 rpm×30 min, and the obtained precipitate was dissolved in 1 mL of water and converted into sodium type by Dowex/r50wx8 50-100

(Na+ type) exchange resin. The obtained product was purified with Bio-Gel P-6, desalted on a Sephadex G-10 column and lyophilized to obtain 8.35 mg of B10. $^1$H—$^{13}$C— and 2D-NMR were detected by the method as described in 1.2 (6) of Example 1, and the structure of compound B10 (methyl signal of carboxyl ester was at 3.7 ppm, —CH$_2$ signal of benzyl was at 4.6 ppm and the benzene ring signal was at 7.3 ppm) was confirmed to be L-Fuc$_{2S4S}$-($\alpha$1,3)-L-6-Methyl-$\Delta$UA-($\alpha$1,3)-D-GaNAc$_{4S6S}$-($\beta$1,4)-[L-Fuc$_{2S4S}$-($\alpha$1,3)]-D-6-Methyl-$\Delta$UA-GlcA-($\beta$1,3)-D-GalNAc$_{4S6S}$-($\beta$1,4)-[L-Fuc$_{2S4S}$-($\alpha$1,3)]-D-O-1-Benzyl-6-Methyl-GlcA, having the structural formula of:

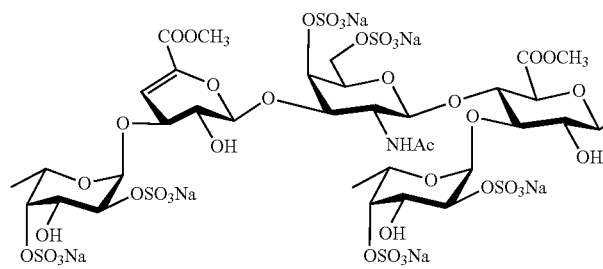
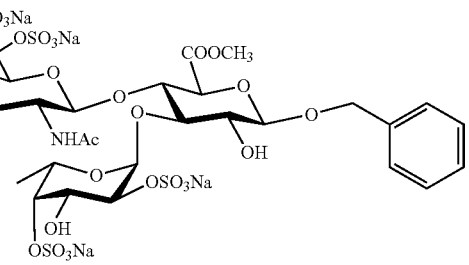

(3) Preparation of compound B11 330 mg of ethyl 4-aminobenzoate was dissolved in 80 μL of a mixture solution of glacial acetic acid and methanol (1:9), and 70 mg of sodium cyanoborohydride was added and dissolved. 20 mg of Compound B3' was dissolved in 2 mL of water, reacted with the mixed solution at 60° C. for 4 h in a constant temperature water bath, extracted with 2 mL of chloroform, and the aqueous phase was purified by Bio-gel P10 column chromatography, desalted by a Sephadex G-10 column and lyophilized to obtain about 14 mg of compound B11.

$^1$H—$^{13}$C— and 2D-NMR were detected by the method as described in 1.2 (6) of Example 1, and the structure of compound B11 (the —CH$_3$ and —CH$_2$ signals of carbethoxy were located at 1.3 ppm and 4.3 ppm, respectively, and the benzene ring signals were divided into two groups at 6.78 ppm and 7.68 ppm, respectively) was confirmed to be L-Fuc$_{2S4S}$-($\alpha$1,3)-L-$\Delta$UA-($\alpha$1,3)-{D-GalNAc$_{4S6S}$-($\beta$1,4)-[L-Fuc$_{2S4S}$-($\alpha$1,3)]-D-GlcA-($\beta$1,3)}2-D-GalNAc$_{4S6S}$-($\beta$1,4)-[L-Fuc$_{2S4S}$-($\alpha$1,3)]-D-1-deoxy-1-amino-GlcA-ol-N-4-benzoic ethyl ester, having the structural formula of:

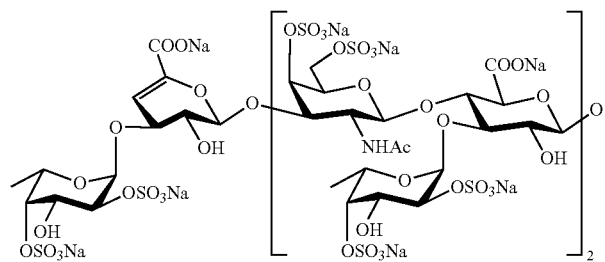
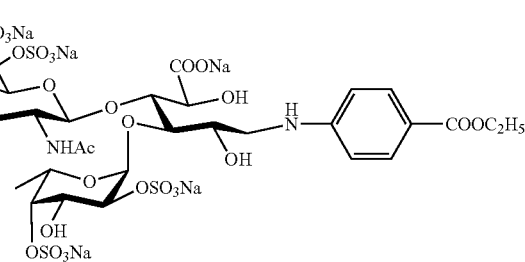

Similarly, when benzyl alcohol is replaced by a corresponding C8-C12 aromatic alcohol (for example, p-methylbenzyl alcohol, p-pentylbenzyl alcohol), a series of derivatives B9' having the corresponding C8-C12 aromatic hydrocarbon group were obtained according to the preparation method of B9 in this Example; when ethyl 4-aminobenzoate is replaced by 4-amino-aromatic (C8-C12) carboxylate (propyl 4-aminobenzoate, pentyl 4-aminobenzoate), a series of derivatives B11' having the corresponding C8-C12 aromatic hydrocarbon group were obtained according to the preparation method of B11 in this Example.

Example 6

Preparation of Oligosaccharide Mixture C1

6.1 Materials

SvFG, obtained as described in Example 1.

The reagents used such as benzethonium chloride, benzyl chloride, DMF, sodium hydroxide, sodium borohydride, sodium chloride, and ethanol are all commercially available analytical reagents. Sephadex G-50 (medium, 50-100 μm), GE Healthcare product.

6.2 Methods (1) Quaternary ammonium salt conversion of SvFG: 70 g of SvFG was dissolved in 1 L of water; and 175 g of benzethonium chloride was dissolved in 2.8 L of water. The SvFG solution was titrated with a benzethonium chloride solution with stirring. After the completion of the titration, the mixture was centrifuged, and the precipitate was washed three times with deionized water and dried under vacuum to obtain 210 g of SvFG quaternary ammonium salt.

(2) Carboxyl esterification of SvFG: The SvFG quaternary ammonium salt obtained in the step (1) was dissolved in 1.020 L of DMF, added with 29 mL of benzyl chloride, and stirred at 35° C. for 24 h, and then the reaction solution was allowed to stand and cool down to room temperature (25° C.). Sample was taken for detecting $^1$H NMR spectrum and the degree of carboxyl esterification of FG was calculated to be about 46%;

(3) β-elimination depolymerization of SvFG in the presence of a reducing agent: To the reaction solution of the step (2), a freshly prepared 333 mL of 0.08 M sodium ethoxide-ethanol solution containing 0.4 M NaBH$_4$ was added, and stirred at room temperature for 30 min.

(4) Post-treatment: To the reaction solution obtained in the step (3), 1.333 L of a saturated sodium chloride solution and 10.7 L of absolute ethanol were added, and centrifuged at 4000 rpm×10 min, and the obtained precipitate was dissolved in 5 L of water, added with 40 mL of 6 M NaOH solution, and reacted for 30 min at room temperature. Then 6 M HCl was dropwise added to neutralize the reaction solution (pH~7.0). The obtained product was ultrafiltered through a 0.1 m² 10 kDa and 3 kDa ultrafiltration membrane pack (Millipore) to remove macromolecular and small molecular impurities, to obtain 35 g of oligosaccharide mixture C1.

(5) Spectral analysis: $^1$H-/$^{13}$C-/2D NMR spectra were detected according to the method described in 1.2 (6) of Example 1.

6.3 Results (1) 35 g of oligosaccharide mixture C1 was obtained according to the described method, with a yield of 50%;

(2) HPGPC analysis showed that C1 contained hexasaccharide, nonasaccharide, dodecasaccharide, pentadecasaccharide, octadecasaccharide and heneicosasaccharide, which were 14.2%, 23.1%, 4.1%, 16.0%, 8.9%, and 5.1%, respectively.

Figure 11:
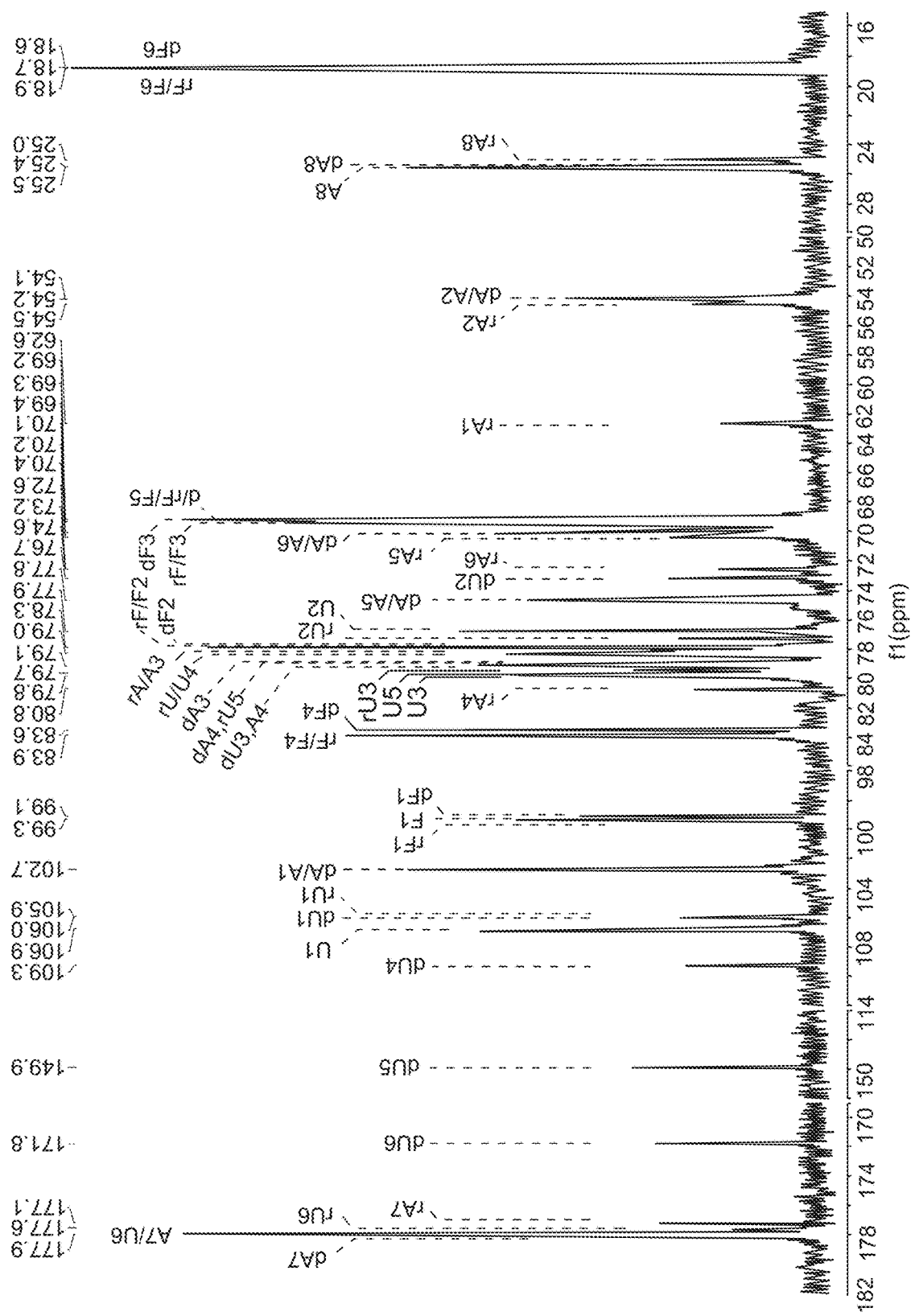
FIG. 11. $^{13}$C NMR spectrum and assignments for Mixture C1

(3) The $^{13}$C NMR spectrum and assignments for the oligosaccharide mixture C1 is shown in FIG. 11. In the $^1$H NMR of the oligosaccharide mixture C1, three strong signal peaks were observed in the range of 5.4~5.7 ppm, wherein the signal peak at 5.77 ppm was H-4 position signal at the non-reducing terminal ΔUA of the oligosaccharide mixture C1. The signals at 5.6 ppm and 5.43 ppm were a terminal hydrogen signal of L-Fuc$_{2S4S}$ in the sugar chain near the reducing terminal and a terminal hydrogen signal of L-Fuc$_{2S4S}$ attached to the non-reducing terminal ΔUA, respectively.

By the signal analysis of the reducing terminal, in particular the carbon signal analysis of the C1 position (—CH$_2$) of -D-GalNAc$_{4S6S}$-ol and -D-GlcA-ol, the content of the oligosaccharide compound having -D-GalNAc$_{4S6S}$-ol at the reducing terminal structure was greater than 95%.

In combination with the $^{13}$C-NMR and 2D-NMR analysis, C1 is composed of homologous oligosaccharide compounds, having the structure of L-Fuc$_{2S4S}$-(α1,3)-L-ΔUA-(α1,3)-{D-GalNAc$_{4S6S}$-(β1,4)-[L-Fuc$_{2S4S}$-(α1,3)]-D-GlcA-(β1,3)}$_n$-D-GalNAc$_{4S6S}$-ol (n is a natural number), wherein the total content of the compounds of n=1~7 is about 95%.

Example 7

Preparation of Oligosaccharide Mixtures D1 and D2

7.1 Materials

HsFG, derived as described in Example 2.

The reagents used such as benzethonium chloride, benzyl chloride, DMF, DMSO, TMSD, sodium hydroxide, sodium borohydride, sodium chloride, and ethanol were all commercially available analytical reagents. Ultrafiltration membrane (0.5 m²) with molecular weight cutoff of 30 kDa, 10 kDa, 3 kDa, Merk Millipore.

7.2 Methods (1) HsFG quaternary ammonium salt conversion: 330 g of HsFG was dissolved in 4.9 L of water; 825 g of benzethonium chloride was dissolved in another 13.2 L of water, the resulting solution was added to the HsFG solution under stirring, centrifuged at 4000 rpm for 10 min. The precipitate was washed three times with 9 L of deionized water and vacuum dried to obtain 804 g of HsFG quaternary ammonium salt.

(2) Carboxyl esterification of HsFG: The HsFG quaternary ammonium salt obtained in the step (1) was placed in a 30 L reactor, dissolved in 3.9 L of DMF. 97 mL of benzyl chloride was added at 35° C., stirred for 24 h, and then the reaction solution was allowed to stand and cool down to room temperature (25° C.). Sample was taken for $^1$H NMR detection and the degree of carboxyl esterification was calculated to be about 46%;

(3) β-elimination depolymerization and terminal peeling reaction of HsFG: a freshly prepared 1.3 L of 0.08 M sodium ethoxide-ethanol solution was added to the reaction solution of step (2), stirred at room temperature for 30 min, and then 2.5 mL of 2 M NaOH solution was added to the reaction solution and stirred at 60° C. for 90 min.

(4) Post-treatment: 5.36 L of saturated sodium chloride solution and 57 L of absolute ethanol were added to the reaction solution of the step (3), centrifuged at 4000 rpm×10 min. The resulting precipitate was dissolved in 14.5 L of water, added with 122 mL of 6 M NaOH, stirred at room temperature for 30 min, and then added with 54.3 g of NaBH$_4$, stirred at room temperature for another 30 min; and dropwise added with 6 M HCl to neutralize the reaction solution (pH~7.0). The obtained reaction solution was filtered through a 0.45 μm membrance filter, and the filtrate was sequentially ultrafiltered with 0.5 m² of 30 kDa (to obtain filtrate), 10 kDa (to obtain filtrate), and 3 kDa (to obtain retentate) ultrafiltration membrane package (Millipore product) and lyophilized, thereby obtaining an oligosaccharide mixture D1 (98.7 g). [Note: After the detection, the undepolymerized macromolecular compositions contained in the retentate obtained from ultrafiltration through a 30 kDa ultrafiltration membrane contains fucan and hexosamine-containing polysaccharides].

(5) D1 carboxymethylation: 20 g of oligosaccharide mixture D1 was dissolved in 300 mL of water, 800 mL of 6.25% benzethonium chloride solution was added with stirring, allowed to stand and then centrifuged at 4000 rpm×10 min. The precipitate was washed three times with 300 mL of deionized water and vacuum dried to obtain 58 g of D1 quaternary ammonium salt. The obtained D1 quaternary ammonium salt was dissolved in 5.8 L of DMSO, added with 87 mL of 2 M TMSD, stirred for 60 min at room temperature, and then added with 87 mL of acetic acid to remove the remaining TMSD; 5.9 L of saturated sodium chloride solution and 63 L of 95% ethanol was sequentially added under stirring, centrifuged at 4000 rpm×30 min. The resulting precipitate was dissolved in 2 L of deionized water, desalted by ultrafiltration through a 3 kDa ultrafiltration membrane, and the retentate was lyophilized to obtain D2 (16.3 g).

(6) Spectral analysis: $^1$H-/$^{13}$C- and 2D-NMR were detected according to the method described in 1.2 (6) of Example 1.

7.3 Results (1) Yield and Chemical Composition Analysis of Oligosaccharide Mixture D1

98.7 g of oligosaccharide mixture D1 was obtained according to the method, with a yield of about 30%.

Figure 12:
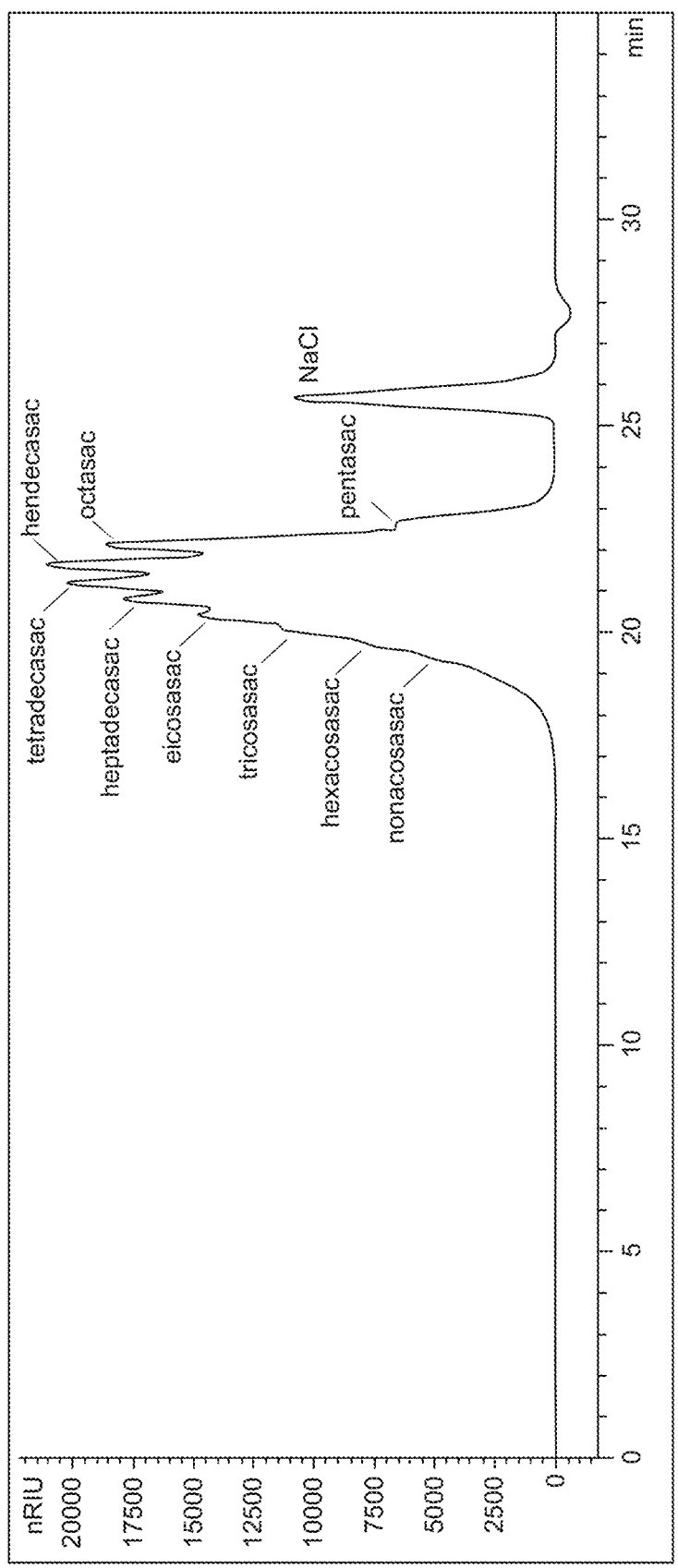
FIG. 12. HPLC profile of Mixture D1

HPGPC analysis (FIG. 12) showed that D1 contained pentasaccharide, octasaccharide, hendecasaccharide, tetradecasaccharide, heptadecasaccharide, eicosasaccharide, which were 4.3%, 17.1%, 18.0%, 16.3%, 14.1%, and 11.1%, respectively. The total content of pentasaccharide ~nonacosasaccharide was about 96%.

Figure 13:
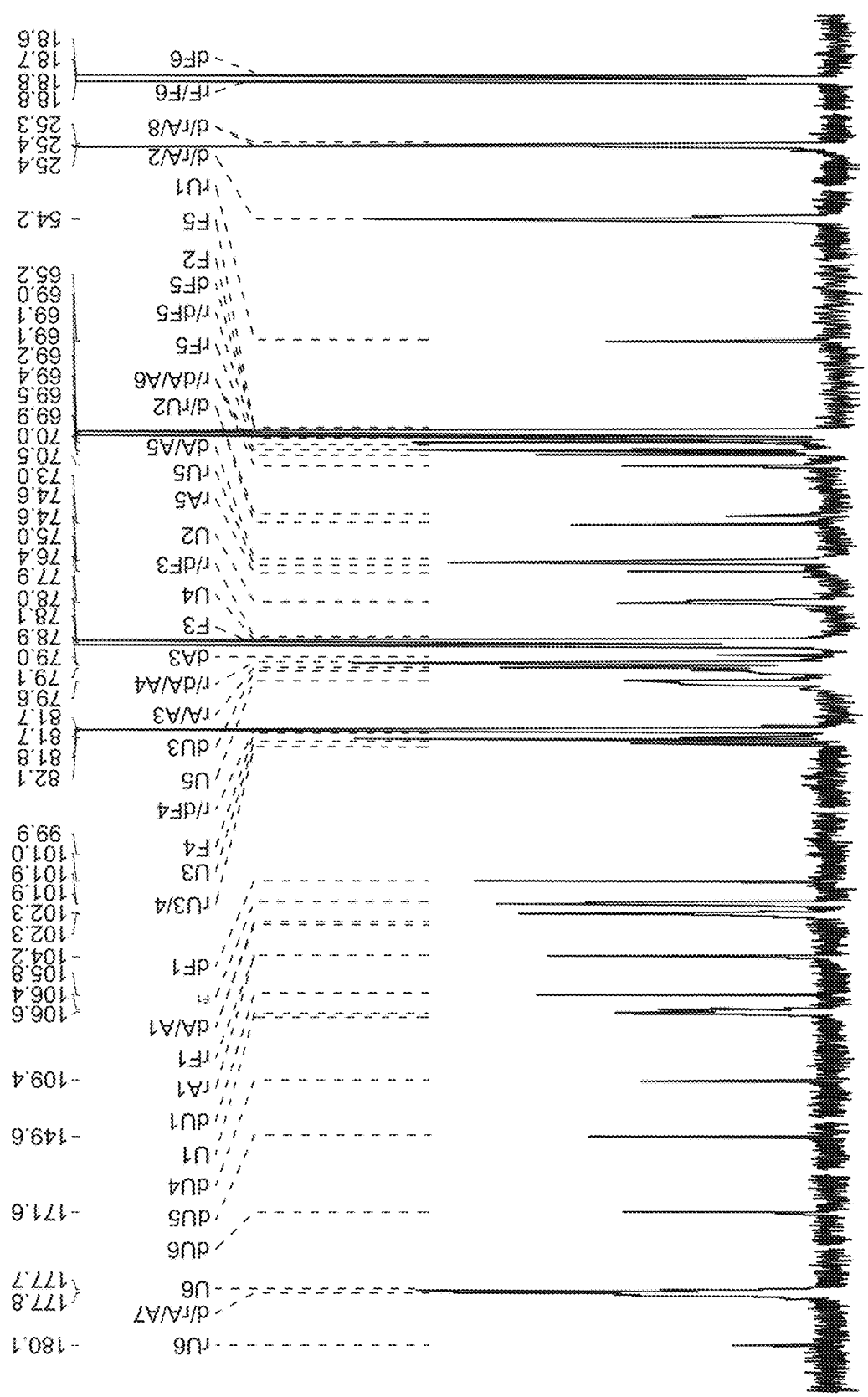
FIG. 13. $^{13}$C NMR spectrum and assignments for Mixture D1

The $^{13}$C-NMR spectrum of the oligosaccharide mixture D1 is shown in FIG. 13. In the $^1$H-NMR of D1, there was a strong signal at 5.685 ppm, which was from 4-position hydrogen of ΔUA. There were three strong signal peaks at 5.0~5.6 ppm (5.283, 5.201 and 5.030 ppm), which were the α-anomeric proton signals of L-Fuc$_{3S4S}$ linked to D-GlcA, ΔUA and D-GlcA-ol, respectively. By analyzing the terminal hydrocarbon signal of the reducing terminal glycosyl group, the content of the oligosaccharide compound having -D-GlcA-ol at the reducing terminal glycosyl group in D1 was more than 95%.

Combined with $^{13}$C- and 2D-NMR analysis, it can be seen that the mixture D1 was a mixture of homologous oligosaccharide compounds having a structure of L-Fuc$_{3S4S}$-(α1,3)-L-AU-(α1,3)-{D-GalNAc$_{4S6S}$-(β1,4)-[L-Fuc$_{3S4S}$-(α1,3)]-D-GlcA-(β1,3)}~-D-GalNAc$_{4S6S}$-(β1,4)-[L-Fuc$_{3S4S}$-(α1,3)]-D-GlcA-ol (n is a natural number).

(2) Analysis of Yield and Chemical Composition of Oligosaccharide Mixture D2

16.3 g of oligosaccharide mixture D2 was obtained according to the method, with a yield of about 80%;

HPGPC analysis showed that it contained pentasaccharide, octasaccharide, hendecasaccharide, tetradecasaccharide, heptadecasaccharide, eicosasaccharide, which were 3.34%, 16.71%, 17.03%, 17.25%, 13.78%, and 12.25%, respectively.

Compared to the $^1$H NMR spectrum of D1, new methyl (ester) group signals linked to hexuronic acid (-ol) appeared in the $^1$H NMR of D2, which were at 3.7 ppm and 3.2 ppm, respectively. In combination with $^1$H—/$^{13}$C— and 2D-NMR analysis, it can be seen that the mixture D2 is a mixture of homologous oligosaccharide compounds having a structure of L-Fuc$_{3S4S}$-(α1,3)-L-6-Me-ΔUA-(α1,3)-{D-GaNAc$_{4S6S}$-(β1,4)-[L-Fuc$_{3S4S}$-(α1,3)]-D-6-Me-GlcA-(β1,4)}~-D-GalNAc$_{4S6S}$-(α1,3)-[L-Fuc$_{3S4S}$-(α1,3)]-D-6-Me-GlcA-ol (n is a natural number). Wherein, the sum of the contents of the compounds of n=1-9 is about 96%.

Example 8

Analysis of Anticoagulation and Coagulation Factor Inhibitory Activity 8.1 Materials Samples: oligosaccharide compounds A1~A8, B1~B11, oligosaccharide mixtures C1, D1, and D2, prepared according to the method described in Examples 1~7.

Control: Enoxaparin Sodium Injection (LMWH, Mw 3500~5500 Da, Sanofi-Aventis product);

Reagents: coagulation-controlled plasma (047B-D024A), activated partial thromboplastin time (APTT), prothrombin time (PT) assay kits, all of which were TECO GmbH company (Germany) products; Factor VIII test kit, Heparin Cofactor II (HCII), AT-dependent anti-factor IIa detection kit, AT-dependent anti-factor Xa detection kit, thrombin (factor IIa), thrombin substrate CS01 (38), KK substrate CS31 (02) were HYPHEN BioMed company (France) products; Factor VIII (FVIII), Bayer Healthcare LLC (Germany) product; ADP, Chronolog company (USA) product; sodium citrate, chloral hydrate, natural saline, were all commercial reagents.

Instruments: XS105 electronic balance, FE20 pH meter, METTLER TOLEDO products; HH-4 constant temperature water bath, Gongyi Yuhua company product, China; VOR76X-6 vortex oscillator, Hainan Qilin Bell product; Spectrafuge-24 D907386 centrifuge, Labnet product; MC-4000 blood coagulation instrument, TICO GmbH company (Germany) product; Microplate Reder ELx 808 microplate reader, Bio-Tek company product; Chronolog-700 platelet aggregation instrument, Chrono-log company (USA) product.

8.2 Methods (1) Preparation of sample solution: Oligosaccharide compounds A1~A8, B1~B11 and oligosaccharide mixtures C1, D1, D2 were all dissolved in Tris-HCl buffer and diluted to the desired series of solubility.

(2) Anticoagulant activity assay: 90 μL of human-controlled plasma was added to the sample or 10 μL of the control solution, and then the clotting time (APTT and PT) was detected by the MC-4000 coagulometer according to the method described in the APTT and PT kit instructions.

(3) Coagulation factor inhibitory activity analysis:

Xase inhibitory activity assay: Detection was performed according to kit instructions and literature methods by combining the Factor VIII and Factor VIII detection kits. Specifically, to each well of a 96-well plate, 30 μL of test solution, control solution, or Tris-HCl buffer (negative control) was added, and 30 μl of FVIII (2 IU/ml), 30 μl of R$_2$ (60 nM FIXa, containing FIIa, PC/PS, Ca$^{2+}$) were sequentially added, mixed by shaking the plate, incubated at 37° C. for 2 min; and then 30 μL of R1 (50 nM FX, containing direct thrombin inhibitor) was added, mixed by shaking the plate, incubated at 37° C. for 1 min; and then 30 μL of R$_3$ (FXa chromogenic substrate SXa-11, about 8.4 mM) was added. The absorbance at 405 nm (OD$_{405}$) was detected with a microplate reader, continuously measuring for 7.5 min at a interval of 30 s. The Xase activity and IC$_{50}$ value of Xase inhibition of the test sample were calculated based on the OD$_{405}$ change value.

AT-dependent Xa inhibitory activity assay: Heparin Anti-FIIa kit was used for detection. To a 96-well plate, 30 μL of sample, control solution or Tris-HCl buffer (negative control) was added, then 30 μL of 1 IU/mL AT solution was added, mixed well and incubated at 37° C. for 1 min; and than 30 μL of 8 μg/mL FXa solution was added, mixed well and incubated at 37° C. for 1 min, then 30 μL of pre-warmed 1.25 mM Xa chromogenic substrate SXa-11 was added. OD$_{405}$ was detected by a microplate reader.

AT-dependent IIa inhibitory activity assay: Heparin Anti-FIIa kit was used for detection. To a 96-well plate, 30 μL of sample, control solution or Tris-HCl buffer (negative control) was added, and then 30 μL of 1 IU/mL AT solution was added, mixed well by shaking the plate and incubated at 37° C. for 2 min; 30 μL of 24 IU/mL FIIa solution was added, mixed well by shaking the plate and incubated for 2 min at 37° C., and then 30 μL of pre-warmed 1.25 mM FIIa specific chromogenic substrate CS-01 (38) was added, mixed well by shaking the plate. The OD$_{405}$ was detected by a microplate reader and the IC$_{50}$ value of FIIa inhibition of each sample was calculated.

HC-II-dependent IIa inhibitory activity assay: 30 μL of sample, control solution or Tris-HCl buffer (negative control) was added, 30 μL of 1 μM HCII solution was added, and incubated at 37° C. for 2 min; and then 30 μL of 20 NIH/mL FIIa was added, and incubated at 37° C. for 1 min; and finally 30 μL of pre-warmed 4.5 mM FIIa chromogenic substrate CS-01 (38) was added. OD$_{405}$ was detected by a microplate reader and the IC$_{50}$ value of FIIa inhibition of each sample was calculated.

Data processing: The average value of OD$_{405}$ detected by the duplicated well was used as the detection value of the test sample and the reference of each concentration, and the slope of the linear fit between the detected value to the time value (the change rate of the absorbance value $OD_{405}$/min) indicated enzymatic activity of coagulation factor. Taking the clotting factor activity of the negative control well as 100%, coagulation factor activity (percentage) in the presence of the test sample was calculated. The coagulation factor activity in the presence of the test sample was plotted against the concentration of the test sample, and fitted according to the following formula, to calculate the $IC_{50}$ value:

$$B=(IC_{50})^n/\{(IC_{50})^n+[I]^n\}$$

in the formula, B is the coagulation factor activity (percentage) in the presence of the test sample, [I] is the concentration of the test sample, $IC_{50}$ is the half inhibitory concentration (concentration of the test sample required to inhibit 50% of the activity), and n is the Hill coefficient.

(4) Effect on surface activation and platelet activity:

FXII activation activity assay: To a 96-well plate was added 30 μL of series concentration sample and reference solution, respectively, and then 30 μL of human standard plasma that was diluted 4 times with a 0.02 M Tris-HCl (pH 7.4) buffer containing 0.15 M NaCl was added, and incubated at 37° C. for 2 min, and then 30 μL of 6 mM kallikrein chromogenic substrate CS-31 (02) was added, and the $OD_{405}$ value was detected by a microplate reader.

Platelet activation activity test: Anticoagulated blood was collected from healthy volunteers to prepare platelet-rich plasma (PRP) and platelet-poor plasma (PPP). Chronolog-700 platelet aggregation instrument and turbidimetry were used to detect platelet-induced aggregation activity of serial concentration solutions of the test sample, which were prepared by dissolving in natural saline.

8.3 Results

Anticoagulation and coagulation factor inhibitory activity: The results are shown in Table 5. The oligosaccharide compounds and the mixture thereof according to the present invention have significant prolonged APTT activity, without affecting PT and TT, indicating that they can have significant anticoagulant activity against intrinsic coagulation pathway, and have no significant effect on extrinsic coagulation. The oligosaccharide compounds and the mixture thereof according to the present invention have significant inhibitory activity on factor Xase; in the presence or absence of antithrombin (AT), they have no significant effect on coagulation factors such as coagulation factors IIa, Xa, XIIa, but may have a certain intensity of heparin cofactor II (HC-II)-dependent IIa inhibitory activity.

An alcohol corresponding to a C2-C6 linear or branched alkane or alkene was selected to prepare the corresponding hydroxyalkylated product A8' according to Example 4. Studies on the activity of these series of derivatives show that they have similar activity to A8, that is, they have prolonged APTT activity (with the drug concentration for doubling the APTT clotting time being 7.0-10 μg/mL), without affecting PT and TT; have significant selective inhibitory activity against factor Xase ($IC_{50}$, 50-100 ng/mL), have no significant effect on coagulation factors such as factor IIa, Xa, XIIa, and have a certain intensity of heparin cofactor II (HC-II)-dependent IIa inhibitory activity.

According to the preparation method of Example B9, a series of derivatives B9' having a corresponding C8-C12 aromatic hydrocarbon group were obtained, and according to the preparation method of Example B11, a series of derivatives B11' having a corresponding C8-C12 aromatic hydrocarbon group were obtained. They have similar activities to B9 and B11, respectively; have drug concentration of doubling APTT clotting time of 6.0-9 μg/mL, without affecting PT and TT; have significant selective inhibitory activity against factor Xase ($IC_{50}$, 40-110 ng/mL), and have a certain intensity of heparin cofactor II (HC-II)-dependent IIa inhibitory activity.

TABLE 5

Anticoagulant and coagulation factor inhibitory activity of oligosaccharide compounds and oligosaccharide mixtures

| | Drug concentration required for multiplication of coagulation time (μg/mL) | | | Drug concentration required to inhibit 50% of coagulation factor activity ($IC_{50}$, ng/mL) | | | |
|---|---|---|---|---|---|---|---|
| | APTT | PT | TT | Xase | Xa (AT) | IIa (AT) | IIa (HC-II) |
| A1 | 60.1 | # | # | ## | ## | ## | 450 |
| A2 | 7.2 | # | # | 60.5 | ## | ## | 323 |
| A3 | 6.8 | # | # | 39.8 | ## | ## | 258 |
| A4 | 5.3 | # | # | 28.2 | ## | ## | 231 |
| A5 | 3.9 | # | # | 23.6 | ## | ## | 320 |
| A6 | 7.5 | # | # | 68.4 | ## | ## | 385 |
| A7 | 6.9 | # | # | 58.9 | ## | ## | 298 |
| A8 | 8.2 | # | # | 70.6 | ## | ## | 335 |
| B1 | 53.9 | # | # | 850 | ## | ## | 705 |
| B2 | 7.5 | # | # | 64.2 | ## | ## | 753 |
| B3 | 6.1 | # | # | 31.1 | ## | ## | 402 |
| B4 | 4.5 | # | # | 20.6 | ## | ## | 408 |
| B5 | 4.0 | # | # | 19.8 | ## | ## | 365 |
| B6 | 50.2 | # | # | 1670 | ## | ## | 817 |
| B7 | 7.3 | # | # | 58.3 | ## | ## | 432 |
| B8 | 5.8 | # | # | 29.6 | ## | ## | 412 |
| B9 | 7.6 | # | # | 59.6 | ## | ## | 706 |
| B10 | 7.9 | # | # | 61.5 | ## | ## | 721 |
| B11 | 6.3 | # | # | 30.3 | ## | ## | 375 |
| C1 | 4.0 | # | # | 22.3 | ## | ## | 404 |
| D1 | 4.3 | # | # | 21.2 | ## | ## | 230 |
| D2 | 5.1 | # | # | 23.6 | ## | ## | 278 |
| LMWH | 7.8 | 64 | 4.0 | 120.0 | 16 | 36 | 431 |

Note:
, >128 μg/mL;
, >5000 ng/mL (2) Effect on Surface Activation and Platelet Activity:

XII activation activity analysis: Within the concentration range of not more than 100 μg/ml, all the oligosaccharide compounds and oligosaccharide mixtures have no significant XII activation activity;

Platelet activation activity assay: Within the concentration range of not more than 50 μg/ml, all oligosaccharide compounds and oligosaccharide mixtures have no significant platelet activation activity.

Example 9

Effect on Antithrombotic Activity and Bleeding 9.1 Materials

The preparation of A2 was as shown in Example 1, and the preparation of D1 was as shown in Example 7.

Control: Low molecular weight heparin (LMWH), Sanofi-Aventis (France) product, batch number 4SH69.

Reagents: chloral hydrate (hydrated trichloroacetaldehyde), Sinopharm Chemical Reagent Co., Ltd.; natural saline, Kunming Nanjiang Pharmaceutical Co., Ltd.

Experimental animals: SD rats, weighing 250~350 g, male, provided by Hunan Slack Jingda Experimental Animal Co., Ltd., license number SCXK (Xiang) 2011-0003; New Zealand rabbits provided by Kunming Medical University. SCXK (Dian) 2011-0004. used to make rabbit brain powder infusion.

9.2 Methods 9.2.1 Anti-Venous Thrombosis Experiment

Grouping and Administration: Rats were randomly divided into 8 groups with 8 animals in each group. The experimental groups and the dose of the animals in each group were (1) natural saline (NS) control group; (2) LMWH 4.0 mg/kg group; (3) A2 2.5 mg/kg group; (4) A2 group 5.0 mg/kg; (5) A2 10 mg/kg group; (6) D1 2.5 mg/kg group; (7) D1 5.0 mg/kg group; (8) D1 10 mg/kg group. The rats in each group were administered subcutaneously (sc.) into the back, and the administration volume was 1 mL/kg. The modeling experiment was performed 1 hour after administration.

Preparation of Rabbit Brain Powder Infusion:

A New Zealand rabbit was sacrificed, and the rabbit brain was taken out immediately. Rabbit brain powder infusion was prepared according to the literature method (*Thromb Haemost*, 2010, 103(5): 994-1004), and stored at −20° C. for use.

Induction of Inferior Vena Cava Thrombosis by Rabbit Brain Powder Infusion:

The rats were anesthetized by intraperitoneally injecting with 10% chloral hydrate (300 mg/kg), the abdominal wall was cut longitudinally along the midline of the abdomen, the viscera was removed, and the inferior vena cava and its branches were isolated. A ligature was passed through the lower margin of the left renal vein of the inferior vena cava, to ligate the inferior vena cava branches below the left renal vein. The femoral vein was injected with 2% rabbit brain powder infusion (1 mL/kg). After 20 seconds, the lower margin of the left renal vein was ligated. After the operation, the viscera was placed back into the abdominal cavity and covered with medical gauze (infiltrated with natural saline). After 20 minutes, the blood vessel was clamped at 2 cm below the ligature, and the blood vessel was longitudinally dissected to take out the thrombus. The length of the thrombus was measured, and the wet weight of the thrombus was weighed and then dry weight was weighed after drying at 50° C. for 24 h.

Data Processing and Statistics:

The SPSS software was used to organize and analyze the data, and the measurement data were expressed as mean±standard deviation (x±s). Data normality in different groups was tested using One-Sample KS test, variance homogeneity was tested using Levene test. If the data conformed to the normal distribution, and the variance was uniform, the significance was judged by One-Way ANOVA, otherwise, the significance was judged by Two-Independent-Samples Test.

9.2.2 Bleeding Tendency Detection

Grouping and administration: Mice were randomly divided into 10 groups with 8 animals in each group. The experimental groups and the dose of the animals in each group were (1) natural saline (NS) control group; (2) LMWH 4.0 mg/kg group; (2) LMWH 20 mg/kg group; (3) LMWH 100 mg/Kg group; (4) A2 5 mg/kg group; (5) A2 25 mg/kg group; (6) A2 125 mg/kg group; (7) D1 5 mg/kg group; (8) D1 25 mg/Kg group; (10) D1 125 mg/kg group. The rats in each group were administered subcutaneously (sc.) into the back, and the dose volume was 10 mL/kg.

Test Methods:

After 60 min of subcutaneous administration in each experimental group, the mice were placed in a mouse holder, and the tail tip was cut by 5 mm by tail-clipping method, and the mouse tail was immersed in 40 mL of purified water (37° C.) in the beaker. Timing was started from the first drop of blood from the cut mouse tail, and stirring was continued. At 60 min, the beaker was placed for 60 min and then the absorbance of the solution (OD540) was detected by a UV spectrophotometer.

In addition, whole blood of healthy mice was taken, and the whole blood of different volumes of mice was added to 40 mL of purified water, stirred uniformly and allowed to stand for 60 min. The absorbance ($OD_{540}$) of the solution was detected by the same method and the volume-absorbance curve was plotted and used as the standard curve for calculating the amount of bleeding. The amount of bleeding in each experimental group was calculated by the standard curve.

Data Processing and Statistics:

The SPSS software was used to organize and analyze the data, and the detected data was expressed as mean±standard deviation (x±s). Data normality in different groups was tested using One-Sample KS test, variance homogeneity was tested using Levene test. If the data conformed to the normal distribution, and the variance was uniform, the significance was judged by One-Way ANOVA, otherwise, the significance was judged by Two-Independent-Samples Test.

Figure 14:
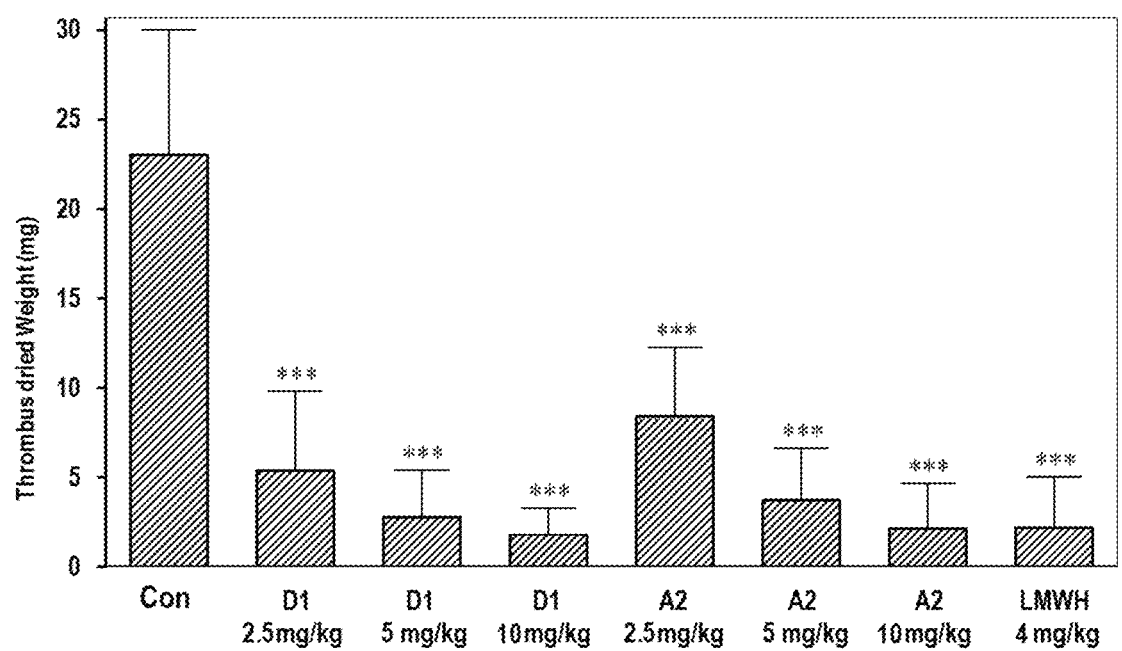

9.3 Results (1) Antithrombotic activity: As shown in FIG. 14, the results show that both A2 and D1 have significant antithrombotic activity at the experimental dose, and the inhibition rate of thrombosis may reach above 70% at the dose of 5 mg/kg~10 mg/kg.

Figure 15:
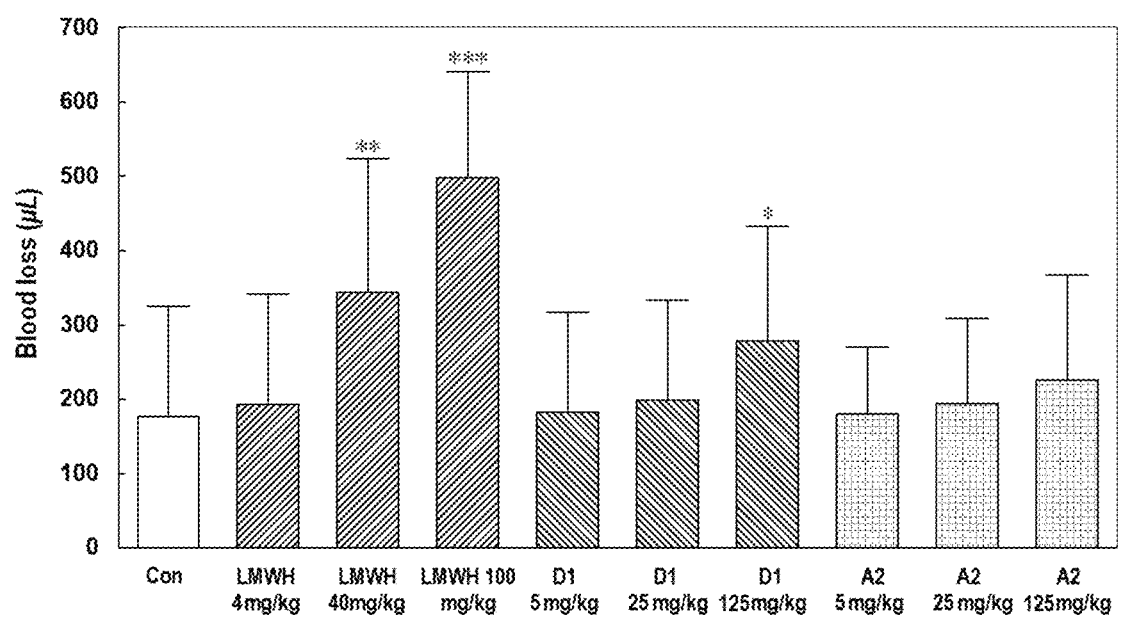
FIG. 15. Effect of A2 and D1 on the amount of bleeding loss in mice

(2) Bleeding tendency influence: As shown in FIG. 15, under high dose administration of equal multiple of the equivalent antithrombotic dose, the amount of bleeding in A2 and D1 administration groups is significantly lower than that in LMWH administration group.

Example 10

Preparation of A3 Pharmaceutical Composition as Lyophilized Powder for Injection 10.1 Materials Compound A3, purified dodecasaccharide compound prepared according to the method described in Example 1.

NaCl, commercially available, pharmaceutical grade; Sterile water for injection; 2 mL medium borosilicate tube glass bottle for injection, Millipore Pellicon 2 ultrafiltration system (Merk Millipore); VirTis Ultra 35 EL lyophilizer.

10.2 Formulation

| Raw material (Excipient) | Dosage |
|---|---|
| A3 | 20 g |
| NaCl | 4 g |
| H₂O | 500 mL |
| Totally prepared into | 1000 vials |

10.3 Preparation Process (1) Process procedure: Twice the prescribed amount of A3 (40 g) and NaCl (8 g) were weighed and dissolved in 1.0 L of water for injection. After dissolved completely under stirring, it was treated by a Millipore ultrafiltration device having an ultrafiltration membrane package with a molecular weight cut-off of 10 kDa to remove the pyrogen. In a sterile environment, after 0.22 μm membrane filtration and sterilization, the solution was filled in a 2 mL vial of 0.5 mL per vial while monitoring the filling process, partially stoppered, and placed in the drying box of the pilot lyophilizer (VirTis, US), lyophilized according to the programmed lyophilization process, stoppered, withdrawn from the lyophilizer, capped, and inspected.

(2) Lyophilization process:

Pre-cooling: The samples were placed in the lyophilizer; the temperature of shelves was dropped to −25° C., maintaining for 1 h, then dropped to −45° C., maintaining for 3 h; the temperature of cold trap was dropped to −50° C., and the vacuum degree was pumped to 40 Pa.

Sublimation: The temperature was increased uniformly to −30° C. within 1 h, maintaining for 2 h; increased uniformly to −20° C. within 2 h, maintaining for 6 h; the vacuum degree was maintained at 40~30 Pa.

Drying: The temperature was increased to −5° C. within 2 h, maintaining for 2 h, and the vacuum was maintained at 30~20 Pa; the temperature was increased to 10° C. within 0.5 h, maintaining for 3 h, and the vacuum degree was maintained at 30-20 Pa; the temperature was increased to 40° C. within 0.5 h, maintaining for 4 h, and the vacuum degree was pumped to the lowest.

10.4 Results

According to the preparation process, 1,960 vials of qualified products of A3 lyophilized preparation were obtained, and the qualified rate of the finished product was about 98%. After testing, the lyophilized cake had regular appearance; the sterility, pyrogen and insoluble particulate testing were all qualified; the moisture testing results showed that the water content was less than about 3%, and the loading testing results showed that the loading was within 95~115% of the planned loading.

Example 11

Preparation of D1 Pharmaceutical Composition as Lyophilized Powder for Injection 11.1 Materials Oligosaccharide mixture D1, prepared according to the method described in Example 7.

NaCl, commercially available, pharmaceutical grade; sterile water for injection; 2 mL medium borosilicate tube glass bottle for injection, Millipore Pellicon 2 ultrafiltration system (Merk Millipore); Lyophilizer (LYO-20 m$^2$), Shanghai Tofflon Sci & Tech Co., Ltd.

11.2 Formulation

| Raw material (Excipient) | Dosage |
|---|---|
| D1 | 50 g |
| NaCl | 9 g |
| H$_2$O | 1.0 L |
| Totally prepared into | 1000 vials |

11.3 Preparation Process (1) Process procedure: 20 times the prescribed amount of D1 (1000 g) and NaCl (180 g) were weighed and dissolved in 20 L of water for injection. After dissolved completely under stirring, it was treated by a Millipore ultrafiltration device having an ultrafiltration membrane package with a molecular weight cut-off of 10 kDa to remove the pyrogen. In a sterile environment, after 0.22 μm membrane filtration and sterilization, the solution was filled in a 2 mL vial of 0.5 mL per vial while monitoring the filling process, partially stoppered, and placed in the drying box of a production lyophilizer (VirTis, US), lyophilized according to the programmed lyophilization process, stoppered, withdrawn from the lyophilizer, capped, and inspected to be qualified, to obtain the final products.

(2) Lyophilization process:

Pre-cooling: The samples were placed in the lyophilizer; the temperature of shelves was dropped to −25° C., maintaining for 1 h, then dropped to −45° C., maintaining for 3 h; the temperature of cold trap was dropped to −50° C., and the vacuum degree was pumped to 40 Pa.

Sublimation: The temperature was increased uniformly to −30° C. within 1 h, maintaining for 2 h; increased uniformly to −20° C. within 2 h, maintaining for 6 h; the vacuum degree was maintained at 40~30 Pa.

Drying: The temperature was increased to −5° C. within 2 h, maintaining for 2 h, and the vacuum degree was maintained at 30-20 Pa; the temperature was increased to 10° C. within 0.5 h, maintaining for 3 h, and the vacuum degree was maintained at 30-20 Pa; the temperature was increased to 40° C. within 0.5 h, maintaining for 4 h, and the vacuum degree was pumped to the lowest.

11.4 Results:

According to the preparation process, 17,600 vials of qualified samples of D1 lyophilized preparation were obtained, and the qualified rate of the finished product was about 88%.

Appearance/characteristic: This product was a white loose mass.

Loading testing: The gravimetric testing was in compliance with the regulations.

Sterility testing: An appropriate amount of this product was taken and tested according to law (1101, Volume IV, Chinese Pharmacopoeia Edition 2015). The test results showed that the batch of samples met the quality requirements of injection.

Pyrogen testing: The product was prepared into a solution containing 3.5 mg of D1 per 1 mL, and tested according to the law (1142, Volume IV, Chinese Pharmacopoeia Edition 2015), the results showed that this batch of samples met the quality requirements of pyrogen testing for injection.

What is claimed is:

1. An oligosaccharide compound or a pharmaceutically acceptable salt thereof, characterized in that, the oligosaccharide compound has antithrombotic activity, and has a general structure represented by Formula (I):

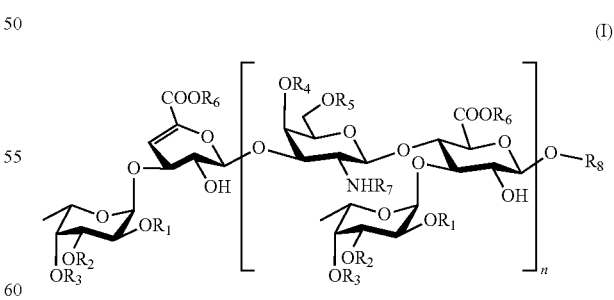

(I)

in the formula, n is a number from 0 to 8;

$R_1$, $R_2$, $R_3$, $R_4$, and $R_5$ are independently H or —SO$_3$H; or $R_6$ is independently —H, a substituted or unsubstituted C1-C6 hydrocarbon group or a C7-C12 aryl group;

$R_7$ is —H, —SO$_3$H, C2-C5 acyl;
$R_8$ is Formula (III):

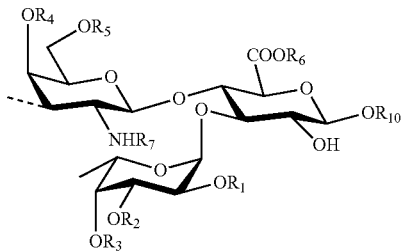

in Formula (III),
$R_1$, $R_2$, $R_3$, $R_4$, $R_5$, $R_6$ and $R_7$ are defined as above; and
$R_{10}$ is independently —H, a substituted or unsubstituted C1-C6 hydrocarbon group or a C7-C12 aryl group.

2. The oligosaccharide compound or a pharmaceutically acceptable salt thereof according to claim 1, wherein in Formula (I) $R_1$=H and $R_2$-$R_5$=SO$_3$H.

3. The oligosaccharide compound or a pharmaceutically acceptable salt thereof according to claim 1, wherein in Formula (I) $R_1$ and $R_2$=H and $R_3$-$R_5$=SO$_3$H.

4. The oligosaccharide compound or a pharmaceutically acceptable salt thereof according to claim 1, wherein in Formula (I) $R_1$ and $R_3$-$R_5$=SO$_3$H and $R_2$=H.

5. The oligosaccharide compound or a pharmaceutically acceptable salt thereof according to claim 1, characterized in that, in the general structure represented by Formula (I), n is 1, 2, 3 or 4.

6. The oligosaccharide compound or a pharmaceutically acceptable salt thereof according to claim 1, characterized in that, the pharmaceutically acceptable salt is an alkali metal salt, an alkaline earth metal salt or an organic ammonium salt.

7. The oligosaccharide compound or a pharmaceutically acceptable salt thereof according to claim 1, characterized in that, the pharmaceutically acceptable salt is a sodium salt, a potassium salt or a calcium salt.

* * * * *